US011760708B2

(12) United States Patent
Petitjean et al.

(10) Patent No.: US 11,760,708 B2
(45) Date of Patent: Sep. 19, 2023

(54) COMPOSITIONS AND METHODS FOR REDUCING ENONES TO SATURATED ALCOHOLS OR KETONES

(71) Applicant: YALE UNIVERSITY, New Haven, CT (US)

(72) Inventors: Laurene Petitjean, New Haven, CT (US); Paul Thomas Anastas, Guilford, CT (US); Tamara Marie DeWinter, San Francisco, CA (US); Philip Coish, North Haven, CT (US); Hanno Christian Erythropel, New Haven, CT (US); Predrag Petrovic, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 17/109,719

(22) Filed: Dec. 2, 2020

(65) Prior Publication Data

US 2021/0163384 A1   Jun. 3, 2021

Related U.S. Application Data

(60) Provisional application No. 62/942,673, filed on Dec. 2, 2019.

(51) Int. Cl.
*C07C 45/62* (2006.01)
*C07C 29/145* (2006.01)
*B01J 23/72* (2006.01)
*B01J 21/04* (2006.01)
*B01J 21/10* (2006.01)
*C07C 49/04* (2006.01)

(52) U.S. Cl.
CPC ............. *C07C 29/145* (2013.01); *B01J 21/04* (2013.01); *B01J 21/10* (2013.01); *B01J 23/72* (2013.01); *C07C 45/62* (2013.01); *C07C 49/04* (2013.01)

(58) Field of Classification Search
None
See application file for complete search history.

(56) References Cited

PUBLICATIONS

Petitjean, L. et al. "Heterogeneous copper-catalyzed direct reduction of C-glycosidic enones to saturated alcohols in water" Green Chem., 2019, 21, 238; published online Jan. 4, 2019 (Year: 2019).*
Ramos, R. et al. "Catalytic conversion of furfural-acetone condensation products into bioderived C8 linear alcohols over NiCu/Al-SBA-15" Catalysis Communications 114 (2018) 42-45 (Year: 2018).*
Debecker, et al., "Exploring, Tuning, and Exploiting the Basicity of Hydrotalcites for Applications in Heterogeneous Catalysis", Chem. Eur. J. 15, 2009, 3920-3935.
Deutsch, et al., "CuH-Catalyzed Reactions", Chem. Rev. 108, 2008, 2916-2927.
Lipshutz, "Copper(I)-mediated 1,2- and 1,4-Reductions", Modern Organocopper Chemistry, edited by N. Krause, Wiley-VCH Verlag GmbH, Weinheim, Germany, 2002, 167-187.
Lipshutz, "Copper-Catalyzed Asymmetric Synthesis", Wiley-VCH Verlag GmbH & Co. KGaA, Weinheim, Germany Editors A. Alexakis, N. Krause and S. Woodward,, 179-201.
Matsumoto, et al., "One-Pot Sequential 1,4- and 1,2-Reductions of α,β-Unsaturated δ-Lactones to the Corresponding δ-Lactols with CuCl and NaBH4 in Methanol", Synlett 25, 2014, 1764-1768.
Petitjean, et al., "Highly selective hydrogenation and Hydrogenolysis using a Copper-doped Porous Metal Oxide Catalyst", Green Chem. 18, 2016, 150-156.

* cited by examiner

*Primary Examiner* — Medhanit W Bahta
(74) *Attorney, Agent, or Firm* — Saul Ewing LLP; Kathryn Doyle; Domingos J. Silva

(57) ABSTRACT

The invention relates to novel, scalable synthetic routes that allow for direct reduction of enones to the corresponding saturated alcohols. The invention relates, in certain aspects, to synthetic routes that allow for the reduction of enones to the corresponding ketones. Such reactions take place under mild conditions, are compatible with a wide range of functional groups, and expand the repertoire of existing green chemistry methodology. In certain embodiments, the reactions are run in aqueous solvent.

9 Claims, 6 Drawing Sheets

COMPOSITIONS AND METHODS FOR REDUCING ENONES TO SATURATED ALCOHOLS OR KETONES

CROSS-REFERENCE TO RELATED APPLICATIONS

The present application claims the benefit of priority under 35 U.S.C. § 119(e) to U.S. Provisional patent Application No. 62/942,673, filed Dec. 2, 2019, the contents of which are incorporated herein by reference their entirety.

STATEMENT REGARDING FEDERALLY SPONSORED RESEARCH OR DEVELOPMENT

This invention was made with government support under DA036151 awarded by National Institutes of Health and under 1339637 awarded by National Science Foundation. The government has certain rights in the invention.

BACKGROUND OF THE INVENTION

C-glycosides have attracted considerable interest as mimics of conventional bioactive 0-glycosides. C-glycosides can be synthesized via condensation of pentane-2,4-dione with unprotected carbohydrates in alkaline aqueous media. The method is in accordance with green chemistry principles and provides access to bio-based, renewable building blocks. The substitution of the 0-glycosidic bond for a carbon-carbon linkage makes these molecules more resistant to acid and enzymatic degradation, thus rendering these compounds of great interest for applications such as anti-tumor agents, antidiabetics, antibiotics, anti-aging molecules, surfactants, and anti-inflammatory compounds. For example, reduction of the Lubineau C-glycoside 1 provided PRO-XYLANE™, a cosmetic ingredient, that stimulates sulfated glycosaminoglycans (GAGs) synthesis, and was launched on the market in 2006 as an active ingredient in skin anti-aging products (Cavezza, et al., 2009, Bioorg. Med. Chem. Lett. 19:845-849).

Aldol reactions and condensations are particularly important for the generation of novel C—C bonds, and will become even more relevant as chemists further embrace sustainability measures, since these reactions can adhere to many green chemistry concepts. Moreover, biomass-derived, renewable molecules are generally more oxidized and oxygenated than petroleum-based molecules. Thus, reactions that take advantage of the higher degree of oxygen groups, such as aldol reactions, will become even more important as the chemical industry shifts its focus towards sustainability. In fact, aldol reactions have already been extensively utilized on carbohydrate compounds and optimized for the syntheses of enone C-glycosides. For example, cyclic and linear C-glycosides can be synthesized using aldol condensation reactions. Recently, a greener and more efficient aldol methodology was developed to synthesize C-glycosidic enones from the Lubineau ketone using L-proline and magnesium oxide or hydrotalcite as a solid base catalyst. The method was used to generate a library of enone analogues, which demonstrated the utility and robustness of the novel methodology (de Winter, et al., 2018, ACS Sustainable Chemistry & Engineering, DOI: 10.1021/acssuschemeng.8b02535; de Winter, et al., 2018, ACS Sus. Chem. & Eng. 6:7810-7817).

Enones, however, can be bioactive due to their electrophilicity, especially at the β-carbon, enabling Michael acceptor reactivity. Michael acceptors are known toxicophores and can elicit interactions with various nucleophiles in cells without prior metabolic activation. For inherent safe design of molecular products, without unintended consequences, the development of selective, economical, and efficient chemical reductions of enones becomes important. Many methods for enone reductions have been developed, but most rely on the use of noble metal catalysts. Primarily, full reductions of enones are still performed in two sequential reactions: the double bond is first reduced (typically using ruthenium (Ru), palladium (Pd), or platinum (Pt), plus hydrogen ($H_2$)) and then, after isolation of the intermediate ketone, the carbonyl is reduced using sodium borohydride ($NaBH_4$).

Thus, there is a need in the art for a practical, economical, and sustainable direct reduction of enones to the corresponding saturated alcohols. Such reduction reaction should allow for scalable synthetic routes for bioactive and/or industrially important compounds. The present invention addresses this need.

BRIEF SUMMARY OF THE INVENTION

The present invention provides a method of reducing an α,β-unsaturated ketone to its corresponding saturated alcohol. In certain embodiments, the method comprises contacting the α,β-unsaturated ketone, a solvent, a copper-doped porous metal oxide, and an inorganic hydride, thus forming a reaction mixture.

In certain embodiments, the solvent comprises methanol or water. In certain embodiments, the reaction mixture is kept at a temperature ranging from 0° C. to about 100° C. In certain embodiments, the inorganic hydride is selected from the group consisting of sodium borohydride and lithium borohydride. In certain embodiments, the metal oxide comprises copper(II), magnesium(II), and aluminum (III). In certain embodiments, the reaction mixture does not comprise hydrogen gas. In certain embodiments, the reaction mixture further comprises hydrogen gas. In certain embodiments, the reaction is run for about 1 hour to about 24 hours. In certain embodiments, the concentration of the α,β-unsaturated ketone in the reaction mixture is about 0.01-0.1 M. In certain embodiments, the reaction mixture is passed through a flow through reactor. In certain embodiments, the reaction mixture is formed within a flow through reactor.

In certain embodiments, the ratio of [copper(II)+magnesium(II)] to aluminum(III) is about 1.5:1 to about 6:1. In certain embodiments, the ratio of copper(II) to magnesium (II) is about 1:9 to about 4:6.

In certain embodiments, the pressure of hydrogen gas used ranges from about 1 to 10 MPa.

In certain embodiments, the amount of inorganic hydride used corresponds to about 2 to about 100 hydride equivalents in terms of the α,β-unsaturated ketone. In certain embodiments, the amount of the metal oxide used corresponds to about 5 to about 500 mol % in terms of the α,β-unsaturated ketone.

In certain embodiments, the reaction mixture is quenched by acidification. In certain embodiments, the quenched reaction mixture is purified by a separation method that separates solid material from the product-containing solution. In certain embodiments, the solid material is extracted at least once with an alcohol. In certain embodiments, the at least one alcohol extract is combined with the product-containing solution. In certain embodiments, the saturated alcohol is isolated from the product-containing solution.

In certain embodiments, the 3-position of the α,β-unsaturated ketone is substituted with an optionally substituted aliphatic or optionally substituted aromatic group. In certain embodiments, the 1-position of the α,β-unsaturated ketone is substitute with an optionally substituted (glycosyl)methyl group.

The present invention further provides a method of reducing an α,β-unsaturated ketone to its corresponding saturated ketone. In certain embodiments, the method comprises contacting the α,β-unsaturated ketone, a solvent, a copper-doped porous metal oxide, and hydrogen gas to form a reaction mixture.

In certain embodiments, the reaction mixture further comprises a Lewis acid. In certain embodiments, the solvent comprises methanol or water. In certain embodiments, the reaction mixture is kept at a temperature ranging from 0° C. to about 100° C. In certain embodiments, the metal oxide comprises copper(II), magnesium(II), and aluminum (III). In certain embodiments, the pressure of hydrogen gas used ranges from about 1 to 10 MPa. In certain embodiments, the reaction is run for about 1 hour to about 24 hours. In certain embodiments, the concentration of the α,β-unsaturated ketone in the reaction mixture is about 0.01-0.1 M. In certain embodiments, the metal oxide used corresponds to about 1 to about 100 mol % in terms of the α,β-unsaturated ketone. In certain embodiments, the reaction mixture is passed through a flow through reactor. In certain embodiments, the reaction mixture is formed within a flow through reactor.

In certain embodiments, the ratio of [copper(II)+magnesium(II)] to aluminum(III) is about 1.5:1 to about 6:1. In certain embodiments, the ratio of copper(II) to magnesium (II) is about 1:9 to about 4:6.

In certain embodiments, the reaction mixture is quenched by acidification. In certain embodiments, the quenched reaction mixture is purified by a separation method that separates solid material from the product-containing solution. In certain embodiments, the solid material is extracted at least once with an alcohol. In certain embodiments, the at least one alcohol extract is combined with the product-containing solution. In certain embodiments, the saturated ketone is isolated from the product-containing solution.

In certain embodiments, the 3-position of the α,β-unsaturated ketone is substituted with an optionally substituted aliphatic or an optionally substituted aromatic. In certain embodiments, the 1-position of the α,β-unsaturated ketone is substituted with an optionally substituted (glycosyl)methyl group.

In certain embodiments, the α,β-unsaturated ketone is an optionally substituted 2-propen-1-one and its corresponding saturated alcohol is an optionally substituted propan-1-ol. In certain embodiments, the α,β-unsaturated ketone is an optionally substituted 2-propen-1-one and its corresponding saturated ketone is an optionally substituted propan-1-one.

BRIEF DESCRIPTION OF THE FIGURES

For the purpose of illustrating the invention, depicted in the drawings are certain embodiments of the invention. However, the invention is not limited to the precise arrangements and instrumentalities of the embodiments depicted in the drawings.

DETAILED DESCRIPTION OF THE INVENTION

The invention relates, in certain aspects, to synthetic routes that allow for direct reduction of enones to the corresponding saturated alcohols. Such reactions are compatible with a wide range of functional groups, and expand the repertoire of existing green chemistry methodology. In certain embodiments, the reactions are run in aqueous solvent. In certain embodiments, a reaction mixture contemplated within the invention is passed through a flow through reactor. In other embodiments, a reaction mixture contemplated within the invention is formed within a flow-through reactor. In certain embodiments, the catalyst is immobilized and/or coated on a solid support. In other embodiments, the immobilized and/or coated-on catalyst and the reaction mixture are contacted in a packed bed reactor. In yet other embodiments, the catalyst is immobilized and/or coated on a reactor surface. In yet other embodiments, the reaction mixture is contacted with the catalyst immobilized and/or coated on a reactor surface.

Metal-hydrides, such as copper hydride, can be used for the 1,2- and 1,4-chemo- and enantio-selective reductions of enones (Lipshutz, 2002, in Modern Organocopper Chemistry, ed. N. Krause, Wiley-VCH Verlag GmbH, Weinheim, Germany, ch. 5, pp. 167-187; Deutsch, et al., 2008, Chem. Rev. 108:2916-2927; Lipshutz, 2014, in Copper-Catalyzed Asymmetric Synthesis, eds. A. Alexakis, N. Krause and S. Woodward, Wiley-VCH Verlag GmbH & Co. KGaA, Weinheim, Germany, ch. 7, pp. 179-201). Further, a heterogeneous copper-doped porous metal oxide (Cu-PMO) catalyst can be employed in selective hydrogenations of alkenes, as well as hydrogenolysis and hydrogenation of aryl ketones (Petitjean, et al., 2016, Green Chem. 18:150-156). Porous metal oxides (PMOs) are derived from hydrotalcite-like precursors of formula $M^{2+}{}_6M^{3+}{}_2CO_3(OH)_{16} \cdot 4H_2O$, which often possess high surface area, and are highly tunable by altering $M^{2+}:M^{3+}$ ratio, and by including other metal dopants (Debecker, et al., 2009, Chem. Eur. J. 15:3920-3935). Cu-PMO is synthesized by co-precipitation of $Cu^{2+}$, $Mg^{2+}$ and $Al^{3+}$ nitrate salts in basic aqueous media, with $M^{2+}:M^{3+}$ kept at 3:1 and Cu composing 20 mol % of $M^{2+}$. After calcination in air, Cu-PMO is obtained as an amorphous solid with metal ratios $Cu_{0.57}Mg_{2.27}Al_{1.00}$. Cu-PMO has the advantages of being entirely composed of earth-abundant elements, inexpensive, and long-lasting on the shelf. The heterogeneous nature of Cu-PMO lessens the cost of product isolation and enables easy recyclability, thus reducing environmental and financial costs.

Figure 1A:
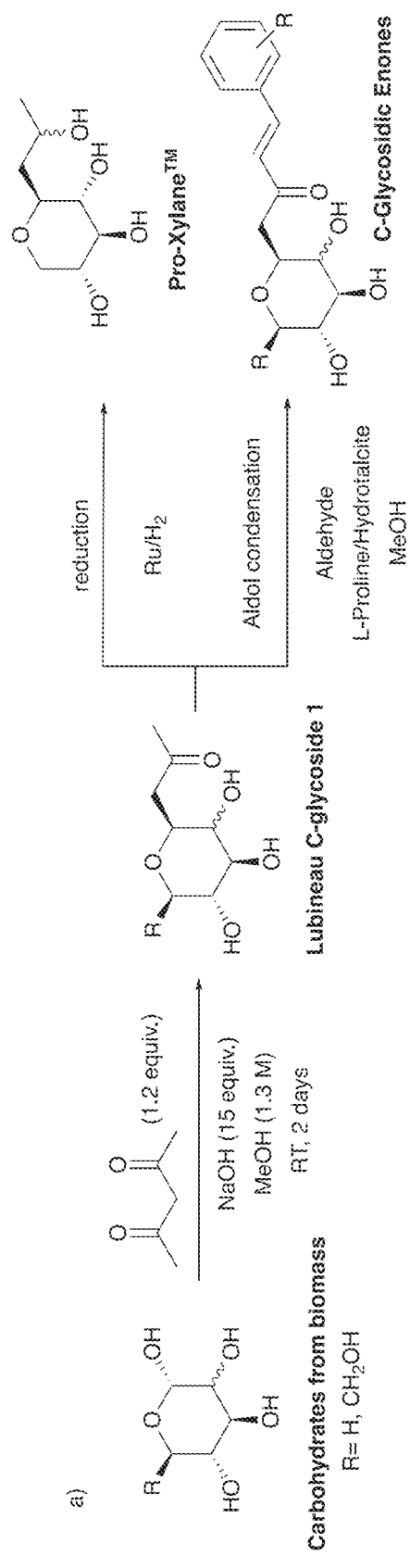
FIG. 1A illustrated previous work enabling syntheses of C-glycosides (Rodrigues, et al., 2000, Chem. Commun. 0:2049-2050; Cavezza & Dalko, WO2010063948A2, 2010; Ramakrishna, et al., 2014, ACS Med. Chem. Lett. 5:878-883).
Figure 1B:
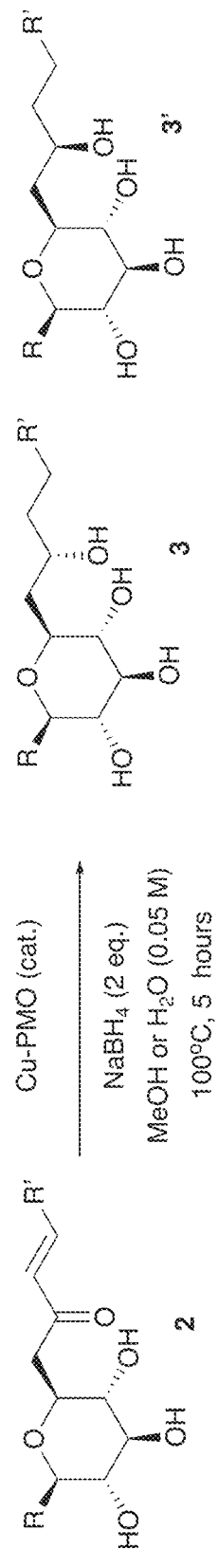
FIG. 1B illustrates an illustrative full Cu-PMO catalyzed reduction of glycoside enones according to certain embodiments of the invention.

The present disclosure relates in part to the investigation and successful development of the Cu-PMO catalyzed reduction of aromatic and aliphatic C-glycosidic enones to the corresponding fully saturated alcohols (FIG. 1B). The present methodology combines several principles of green chemistry: the use of renewable C-glycosidic substrates, of water as a benign solvent, the minimization of derivatives by performing the reduction on non-protected glycosides, the use of catalysis, especially with the earth-abundant elements, and the lack of extensive purifications, which lowers the amount of generated waste. Further, the present methodology allows access to safer molecules with an easy-to-implement reduction of potentially toxic, reactive enone moieties.

Enones were prepared following the general procedure shown in FIGS. 1A-1B. For example, enone 2a (FIG. 1A, R=H) was prepared from Lubineau C-Glycoside 1 (R=H) and benzaldehyde, following a protocol that employs L-proline and a solid base catalyst (de Winter, et al., 2018, ACS Sus. Chem. & Eng. 6:7810-7817).

The invention relates, in certain aspects, to synthetic routes that allow for the reduction of enones to the corresponding ketones. The use of Cu-PMO (11 mol %) and 4 MPa of hydrogen at 100° C., for 18 hours in methanol (0.01 M), provided very selective and quantitative conversion of the starting C-glycosidic enone to the corresponding ketone 5a (See Example 1, Part K, under "5. C-Glycosidic ketones 5a and 5d"). Similar reactivity was observed when methanol was replaced with water, while keeping all other conditions the same. This result represents a selective, conjugate reduction of an enone in water with a heterogeneous catalyst made of earth-abundant elements. In certain non-limiting embodiments, the reduction does not require an added base for catalyst stability or for turnover rate enhancement, or a ligand for hydride stabilization.

Figure 2:
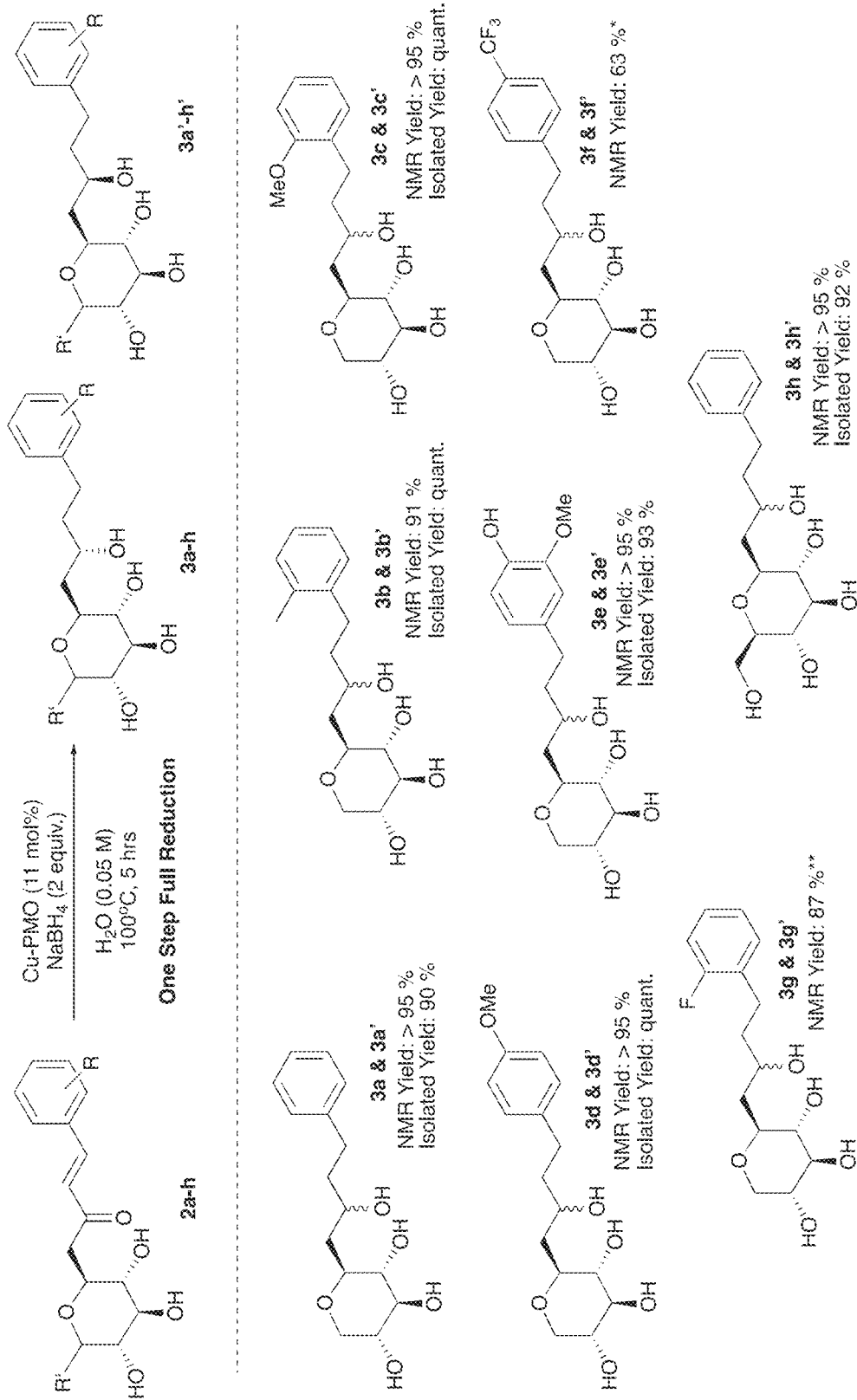
FIG. 2 illustrates non-limiting examples of the copper-catalyzed full reduction of C-glycosidic aromatic enones. All NMR yields are calculated from NMR spectroscopy of the crude reaction mixture using an internal standard. Isolated yields were calculated after weighing and NMR verification of the absence of boron salts. All reactions showed full conversion of the starting material using NMR quantitation. *The reaction also furnished 36% unsaturated alcohol 4f. **The reaction also furnished 15% of unsaturated alcohol 4g.

The invention relates, in certain aspects, to synthetic routes that allow for the reduction of enones to the corresponding saturated alcohols. In a non-limiting example, the methodology provides quantitative and clean conversion of enone 2a (R=H) to the desired product 3a (FIG. 2). Stirring of enone 2a with Cu-PMO (11 mol %) and $NaBH_4$ (2 equivalents) at 100° C., for 5 hours, in $H_2O$ (0.05 M) provided the desired product 3a in quantitative yield (FIG. 2). In another non-limiting example, stirring of enone 2a with Cu-PMO (11 mol %) and $NaBH_4$ (2 equivalents) at 100° C. under hydrogen pressure (4 MPa), for 1-2 hours, in methanol (0.05 M) provided the desired product 3a in quantitative yield. In yet another non-limiting example, stirring of enone 2a with Cu-PMO (11 mol %) and $NaBH_4$ (2 equivalents) at 100° C. under hydrogen pressure (4 MPa), for 2 hours, in water (0.05 M) provided the desired product 3a in quantitative yield. Yet other embodiments are reported in Table 1.

The desired products were easily isolated without the need for further purification after a simple work-up procedure. The crude reaction mixtures were acidified with Amberlite IR-120H$^+$ resin, followed by removal of the catalyst and resin by filtration, and washing the filtered residue with methanol. Concentration of the filtrate by rotatory evaporation and drying under high vacuum provided the desired product (as a diastereomeric mixture) in high yield. The absence of boron salts was confirmed by $^1H$ and $^{11}B$ NMR analysis. If boron salts were present, the mixture was re-dissolved in methanol and evaporated in vacuo, and the process was repeated until the absence of boron salts was confirmed by NMR. The Smith and Goodman's methodology was used for assigning diastereomers using computational modelling of NMR chemical proton and carbon shifts (Smith & Goodman, 2009, J. Org. Chem. 74:4597-4607).

TABLE 1

One step Cu-catalyzed full reduction of C-Glycosidic enones*

| Entry | Cat. (mol %) | Temp (° C.) | $H_2$ (MPa) | Time (h) | Add. (Eq.) | solvent (M) | NMR Conversion (%) | NMR Yield 3a (%) | NMR Yield 4a (%) | NMR Yield 58 (%) |
|---|---|---|---|---|---|---|---|---|---|---|
| 1 | CuPMO (11) | 100 | 4 | 18 | $NaBH_4$ (2) | MeOH (0.01) | 100 | >95 | 0 | 0 |
| 2 | CuPMO (11) | 100 | 4 | 18 | $NaBH_4$ (2) | MeOH (0.05) | 100 | >95 | 0 | 0 |
| 3 | CuPMO (11) | 100 | 4 | 4 | $NaBH_4$ (2) | MeOH (0.05) | 100 | >95 | 0 | 0 |
| 4 | CuPMO (11) | 100 | 4 | 2 | $NaBH_4$ (2) | MeOH (0.05) | 100 | >95 | 0 | 0 |
| 5 | CuPMO (11) | 100 | 4 | 1 | $NaBH_4$ (2) | MeOH (0,05) | 100 | 92 | 0 | 0 |
| 6 | CuPMO (11) | 100 | 4 | 2 | $NaBH_4$ (2) | $H_2O$ (0.05) | 100 | >95 | 0 | 0 |
| 7 | CuPMO (11) | 100 | — | 5 | $NaBH_4$ (2) | $H_2O$ (0.05) | 100 | >95 | 0 | 0 |

*DMF or CHCl3 were used as internal standards for NMR quantitations

Figure 3:
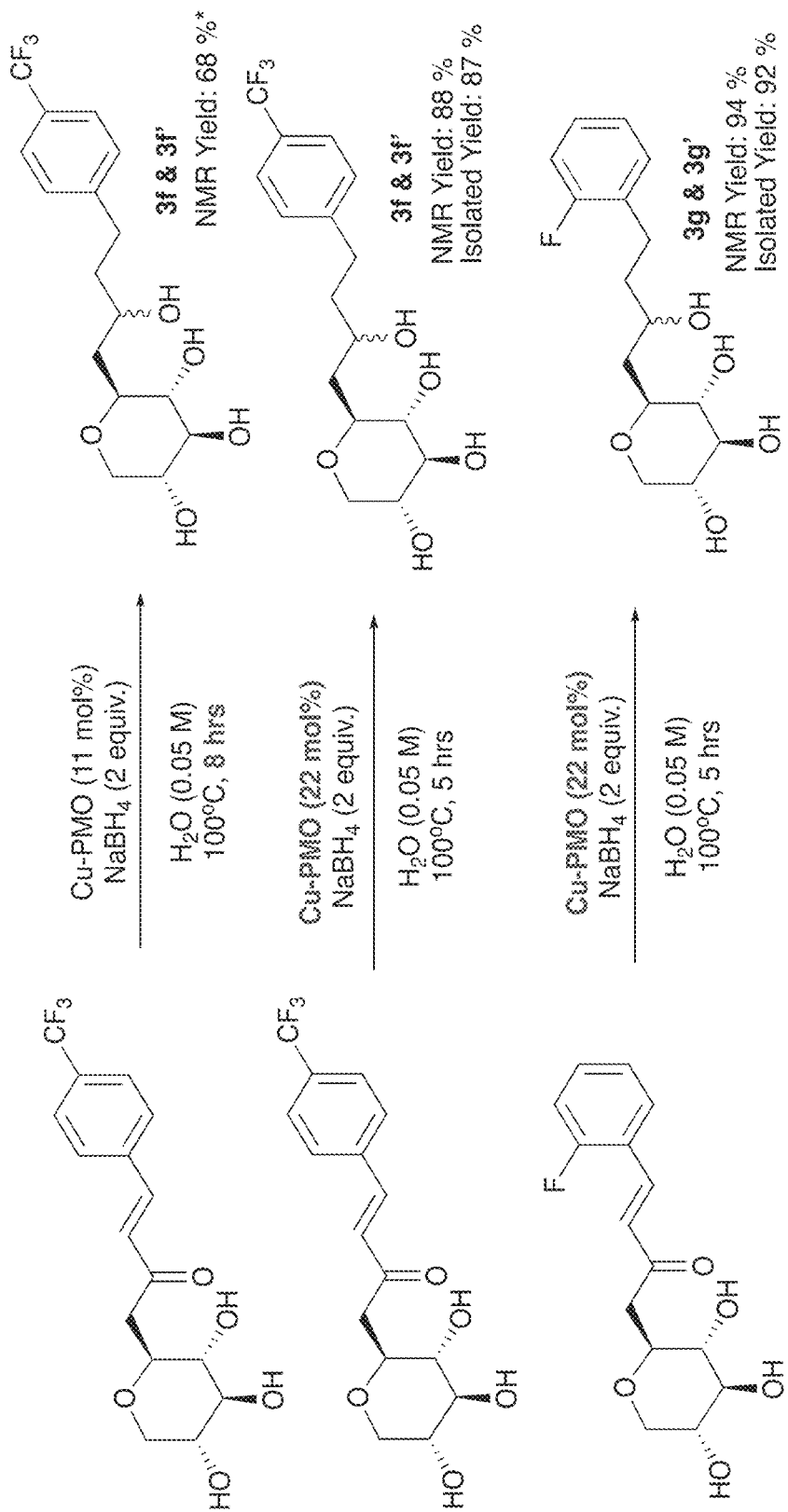
FIG. 3 illustrates the copper-catalyzed full reduction of the C-glycosidic aromatic enones 2f and 2g to the corresponding, saturated alcohols. All reactions showed full conversion of starting materials using NMR quantitation. Isolated yields were calculated using the masses of product mixtures after NMR verification of the absence of boron salts. All reactions showed full conversion of the starting material using NMR quantitation. *The reaction also furnished 36% unsaturated alcohol 4f.

The scope of the method was evaluated using various aryl substituted C-glycosidic enones (FIG. 2). The L-proline and solid base catalyst protocol was used to prepare the enone substrates by condensing xylose- or glucose-derived Lubineau ketones with substituted benzaldehydes. Trifluoromethyl-substituted 3f/3f' and fluoro-substituted 3g/3g' were obtained in moderate (63%) and high (87%) yields, respectively, along with the unsaturated (allylic) alcohols 4f and 4g (FIG. 2). A two-fold increase in the catalyst loading resulted in full and selective conversion of the trifluoromethyl-substituted and fluoro-substrates to the fully reduced alcohols 3f/3f' and 3g/3g', respectively (FIG. 3).

Figure 4:
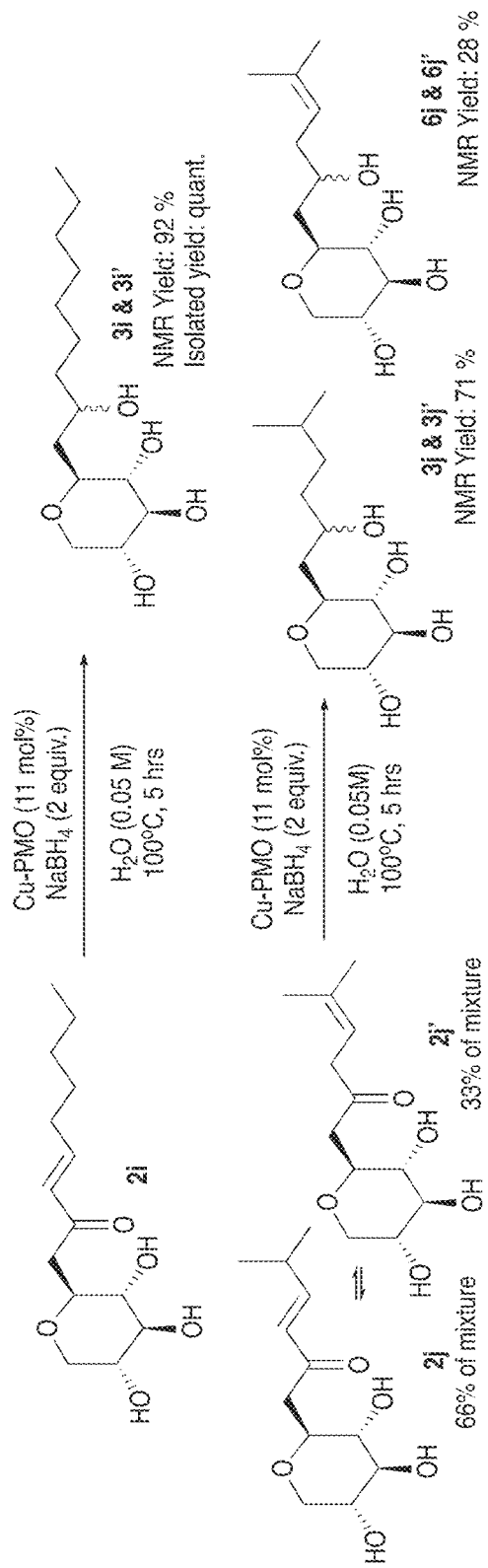
FIG. 4 illustrates non-limiting examples of the copper-catalyzed full reduction of C-glycosidic aliphatic enones. All yields are calculated from NMR spectroscopy of the crude reaction mixture using $CHCl_3$ as an internal standard. All reactions showed full conversion of the starting material using NMR quantitation.

The reaction conditions are amenable to the reduction of aliphatic C-glycosidic enones (FIG. 4). The aliphatic enones were fully and selectively reduced to the corresponding aliphatic alcohols 3i/3i' and 3j/3j' in high yields. Compound 2j is prone to UV-induced deconjugation, and is obtained from aldol condensation as a mixture with deconjugated isomer 2j' in a 2:1 ratio of 2j:2j' (FIG. 4). The present methodology furnishes desired product 3j/3j' in 70% yield whereas the alcohol 6j/6j' is obtained in 30% yield.

Heterogeneous catalysts provide the advantage of facile recyclability, necessitating, in our case, solely a filtration for catalyst recovery after reaction. In certain embodiments, Cu-PMO can be recycled further without loss of activity or selectivity. In addition to the recycling of the catalyst, Amberlite IR-120 H$^+$ can be regenerated and re-used after treatment with a mineral acid.

In certain embodiments, any of the reaction mixture contemplated herein is free of organic solvents.

The applicability of the method was tested on multigram scale. Reduction of 2e (8.1 g) provided 5.1 g of pure product 3e/3e' (73% isolated yield) after short path filtration of the crude over silica. The optimized reaction conditions were robust without alterations to large, industrially relevant scales.

In summary, the present report relates to the successful development and optimization of a novel method for the reduction of α,β-unsaturated enones to the corresponding fully saturated alcohols. The method employs a heterogeneous copper catalyst in water and requires only resin-treatment for isolation of C-glycosidic alcohols as pure, diastereomeric mixtures. Furthermore, the process of the invention is a green alternative to the two-step, precious noble metal and stoichiometric methodologies typically utilized to achieve full enone reduction.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It should be contemplated that the invention includes each and every one of the synthetic schemes described and/or depicted herein.

Methods

The invention provides a method of reducing an α,β-unsaturated ketone (optionally substituted 2-propen-1-one) to the corresponding saturated alcohol (optionally substituted propan-1-ol).

In certain embodiments, the method comprises contacting the α,β-unsaturated ketone, a solvent, a copper-doped porous metal oxide, and an inorganic hydride, thus forming a reaction mixture. In other embodiments, the solvent comprises methanol. In yet other embodiments, the solvent comprises water. In yet other embodiments, the reaction mixture is free of organic solvents. In yet other embodiments, the reaction mixture is kept at a temperature ranging from 0° C. to about 100° C.

In certain embodiments, the inorganic hydride is selected from the group consisting of sodium borohydride and lithium borohydride.

In certain embodiments, the metal oxide comprises copper(II), magnesium(II), and aluminum (III). In yet other embodiments, the ratio of [copper(II)+magnesium(II)] to aluminum(III) is about 1.5:1 to about 6:1. In yet other embodiments, the ratio of [copper(II)+magnesium(II)] to aluminum(III) is about 3:1. In yet other embodiments, the ratio of copper(II) to magnesium (II) is about 1:9 to about 4:6. In yet other embodiments, the ratio of copper(II) to magnesium (II) is about 2:8.

In certain embodiments, the reaction mixture does not comprise hydrogen gas. In certain embodiments, the reaction mixture further comprises hydrogen gas. In other embodiments, the pressure of hydrogen gas used ranges from about 1 to 10 MPa.

In certain embodiments, the reaction is run for about 1 hour to about 24 hours.

In certain embodiments, the amount of inorganic hydride used corresponds to about 2 to about 100 hydride equivalents in terms of the α,β-unsaturated ketone. In certain embodiments, the amount of inorganic hydride used corresponds to about 2 to about 40 equivalents in terms of the α,β-unsaturated ketone.

In certain embodiments, the concentration of the α,β-unsaturated ketone in the reaction mixture is about 0.01-0.1 M.

In certain embodiments, the amount of metal oxides used corresponds to about 5 to about 100 mol % in terms of the α,β-unsaturated ketone.

In certain embodiments, the reaction mixture is free of organic solvents. In other embodiments, the reaction mixture comprises at least one organic solvent.

In certain embodiments, the reaction mixture is quenched by acidification. In other embodiments, the acidification comprises adding an acidic resin to the reaction mixture. In yet other embodiments, the resin comprises a weakly acidic or strongly acidic resin. In yet other embodiments, the quenched reaction mixture is purified by a separation method that separates solid material from the product-containing solution. In yet other embodiments, the separation method comprises decantation, filtration, and/or centrifugation. In yet other embodiments, the solid material is extracted at least once with an alcohol. In yet other embodiments, the alcohol comprises methanol or ethanol. In yet other embodiments, the at least one alcohol extract is combined with the product-containing solution. In yet other embodiments, the saturated alcohol is isolated from the product-containing solution. In yet other embodiments, the isolation of the saturated alcohol comprises extraction, evaporation, or concentration under vacuum. In yet other embodiments, any boron species is at least partially removed from the product mixture by treatment with borate-specific chelating resin before addition of an alcohol.

In certain embodiments, the desired product is isolated by any chromatographic method known in the art.

In certain embodiments, the substitution at the 3-position of the ketone is an optionally substituted aliphatic or optionally substituted aromatic group. In certain embodiments, the substitution at the 1-position of the ketone is an optionally substituted (glycosyl)methyl group.

The invention also provides a method of reducing an α,β-unsaturated ketone (optionally substituted 2-propen-1-one) to the corresponding saturated ketone (optionally substituted propan-1-one).

In certain embodiments, the method comprises contacting the α,β-unsaturated ketone compound, a solvent, a copper-doped porous metal oxide, and hydrogen gas to form a reaction mixture.

In certain embodiments, the reaction mixture further comprises a Lewis acid. In other embodiments, the Lewis acid is at least one salt selected from the group consisting of lithium, sodium, potassium, and rubidium.

In certain embodiments, the solvent comprises methanol. In other embodiments, the solvent comprises water. In yet other embodiments, the reaction mixture is free of organic solvents.

In certain embodiments, the reaction mixture is kept at a temperature ranging from 0° C. to about 100° C.

In certain embodiments, the metal oxide comprises copper(II), magnesium(II), and aluminum (III). In yet other embodiments, the ratio of [copper(II)+magnesium(II)] to aluminum(III) is about 1.5:1 to about 6:1. In yet other embodiments, the ratio of [copper(II)+magnesium(II)] to aluminum(III) is about 3:1. In yet other embodiments, the ratio of copper(II) to magnesium (II) is about 1:9 to about 4:6. In yet other embodiments, the ratio of copper(II) to magnesium (II) is about 2:8.

In certain embodiments, the pressure of hydrogen gas used ranges from about 1 to 10 MPa.

In certain embodiments, the reaction is run for about 1 hour to about 24 hours.

In certain embodiments, the concentration of the α,β-unsaturated ketone in the reaction mixture is about 0.01-0.1 M.

In certain embodiments, the amount of the metal oxide used corresponds to about 1 to about 100 mol % in terms of the α,β-unsaturated ketone.

In certain embodiments, the reaction mixture is quenched by acidification. In other embodiments, the acidification comprises adding an acidic resin to the reaction mixture. In yet other embodiments, the resin comprises a weakly acidic or strongly acidic resin. In yet other embodiments, the quenched reaction mixture is purified by a separation method that separates solid material from the product-containing solution. In yet other embodiments, the separation method comprises decantation, filtration, and/or centrifugation. In yet other embodiments, the solid material is extracted at least once with an alcohol. In yet other embodiments, the alcohol comprises methanol or ethanol. In yet other embodiments, the at least one alcohol extract is combined with the product-containing solution. In yet other embodiments, the saturated ketone is isolated from the product-containing solution. In yet other embodiments, the isolation of the saturated ketone comprises extraction, evaporation, or concentration under vacuum.

In certain embodiments, the substitution at the 3-position of the ketone is optionally substituted aliphatic or optionally substituted aromatic. In certain embodiments, the substitution at the 1-position of the ketone is an optionally substituted (glycosyl)methyl group.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts.

Suitable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is $(C_1-C_3)$alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1-C_{10}$ means one to ten carbon atoms) and includes straight, branched chain, or cyclic substituent groups. Examples include methyl, ethyl, propyl, isopropyl, butyl, isobutyl, tent-butyl, pentyl, neopentyl, hexyl, and cyclopropylmethyl. A specific embodiment is $(C_1-C_6)$alkyl, such as, but not limited to, ethyl, methyl, isopropyl, isobutyl, n-pentyl, n-hexyl and cyclopropylmethyl.

As used herein, the term "cycloalkyl" by itself or as part of another substituent refers to, unless otherwise stated, a cyclic chain hydrocarbon having the number of carbon atoms designated (i.e., $C_3-C_6$ refers to a cyclic group comprising a ring group consisting of three to six carbon atoms) and includes straight, branched chain or cyclic substituent groups. Examples of $(C_3-C_6)$cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, the language "salt" refers to a salt of the administered compound prepared from acids and/or bases, including inorganic acids, inorganic bases, organic acids, inorganic bases, solvates (including hydrates) and clathrates thereof.

As used herein, the term "substituted" refers to that an atom or group of atoms has replaced hydrogen as the substituent attached to another group.

As used herein, the term "substituted alkyl" or "substituted cycloalkyl" refers to alkyl or cycloalkyl, as defined elsewhere herein, substituted by one, two or three substituents independently selected from the group consisting of halogen, —OH, alkoxy, tetrahydro-2-H-pyranyl, —NH$_2$, —NH($C_1$-$C_6$ alkyl), —N($C_1$-$C_6$ alkyl)$_2$, 1-methyl-imidazol-2-yl, pyridin-2-yl, pyridin-3-yl, pyridin-4-yl, —C(=O)OH, —C(=O)O($C_1$-$C_6$)alkyl, trifluoromethyl, —C(=O)NH$_2$, —C(=O)NH($C_1$-$C_6$)alkyl, —C(=O)N(($C_1$-$C_6$)alkyl)$_2$, —SO$_2$NH$_2$, —SO$_2$NH($C_1$-$C_6$ alkyl), —SO$_2$N($C_1$-$C_6$ alkyl)$_2$, —C(=NH)NH$_2$, and —NO$_2$, in certain embodiments containing one or two substituents independently selected from halogen, —OH, alkoxy, —NH$_2$, trifluoromethyl, —N(CH$_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic.

Unless otherwise noted, when two substituents are taken together to form a ring having a specified number of ring atoms (e.g., $R^2$ and $R^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These

Examples are provided for the purpose of illustration only, and the invention is not limited to these Examples, but rather encompasses all variations that are evident as a result of the teachings provided herein.

It should be noted in certain protocols the term/unit "Vol" or "volume" or "volumes" is used to denote a relative amount of solvent volume to be used, and does not limit the scope of the invention in any manner.

General Experimental

Chemicals and solvents were purchased from Sigma-Aldrich, Alfa-Aesar, JT Baker or TCI and used as received. Compound 1a (Octulose) was obtained as a solution in $H_2O$, and concentrated in vacuo before use.

All hydrogenation reactions under $H_2$ atmosphere were set-up in a 100 mL stainless-steel Parr reactor equipped with a mechanical stirrer. The reactions were pressurized under Hydrogen Atmosphere (Airgas, Ultra High Purity). The loaded reactor was placed on a bench-top Parr stand equipped with a Parr 4843 reactor controller.

Proton nuclear magnetic resonance ($^1$H NMR) spectra were acquired using Agilent DD2 400 MHz, Agilent DD2 500 MHz, Agilent DD2 600 MHz or Varian Inova 500 MHz spectrometers. Chemical shifts ($\delta$) are reported in parts per million (ppm) and are calibrated to the residual solvent peak. Coupling constants (J) are reported in Hz. Multiplicities are reported using the following abbreviations: s=singlet; d=doublet; t=triplet; m=multiplet (range of multiplet is given). Carbon nuclear magnetic resonance CC NMR) spectra were acquired using Agilent DD2 600 MHz or Agilent DD2 400 MHz spectrometer. Chemical shifts ($\delta$) are reported in parts per million (ppm) and are calibrated to the residual solvent peak.

X-Ray Powder Diffraction (XRPD) measurements were performed on a Bruker D8-focus X-Ray diffractometer equipped with a Cu line-focus sealed tube, a divergent beam geometer and a NaI scintillation detector. Measurements were made with a 40 kV, 40 mA beam in the range 2θ from 3° to 80° locked couple scan type, a step size of 0.05° and a scan speed of 1 second/step.

Analytical thin layer chromatography was performed on pre-coated 250 μm layer thickness silica gel 60 $F_{254}$ Plates (EMD Chemicals Inc.). Visualization was performed by ultraviolet light and/or by staining with potassium permanganate or ceric ammonium molybdate (CAM) solutions. Purifications by column chromatography were performed using SilicaFlash F60 silica gel (40-63 μm, 230-400 mesh, Silicycle).

Elemental analyses were performed using inductively coupled plasma optical emission spectroscopy (ICP-OES) on a Perkin Elmer Optima 3000 equipped with a Scott nebulizer. The Sc standard was measured at 361.384 nm, Cu at 324.754 nm, Mg at 279.079 nm and Al at 308.215 nm. Samples were prepared for ICP-OES by dissolving a known solid amount in 2 mL of 6 M nitric acid and diluting to 50 mL with DI $H_2O$.

Elemental components were quantified by comparison with purchased calibration standards. High resolution mass spectra (HRMS) were recorded using an Agilent 6550A QTOF by electrospray ionization time of flight experiments.

Example 1

A. Synthesis of the Cu-PMO Catalyst

Figure 5:
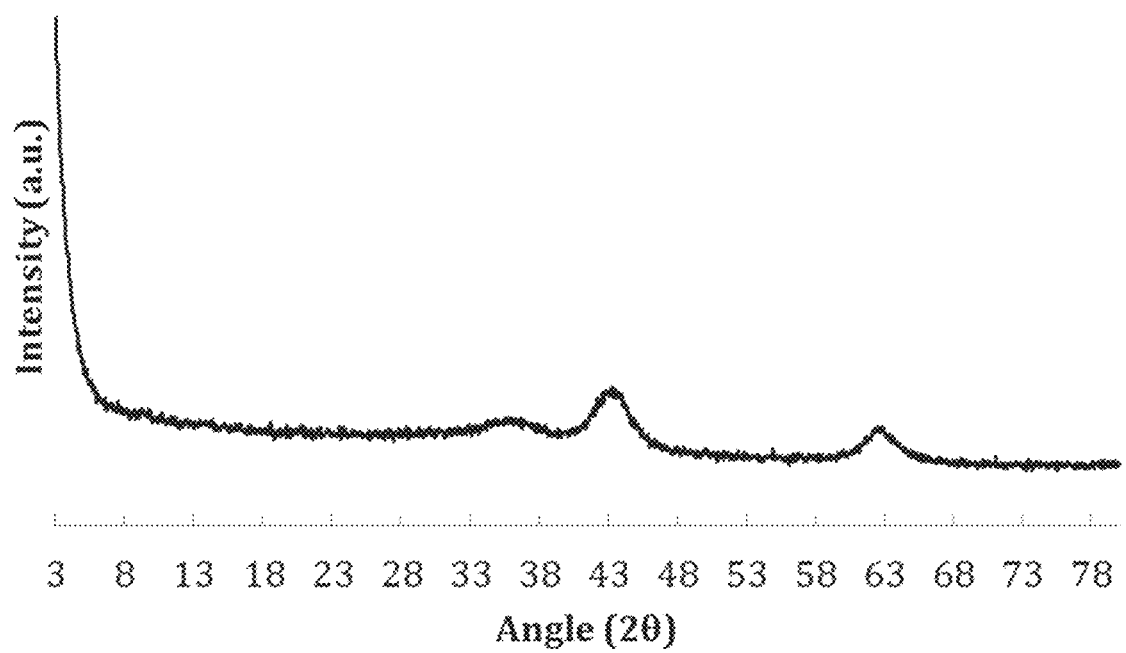
FIG. 5 illustrates a XPRD spectrum of Cu-PMO catalyst.

A solution of $Al(NO_3)_3 \cdot 9H_2O$ (18.8 g, 0.05 mol, 1 equiv.), $Mg(NO_3)_2 \cdot 6H_2O$ (30.76 g, 0.12 mol, 2.4 equiv.) and $Cu(NO_3)_2 \cdot 2.5H_2O$ (7.0 g, 0.03 mol, 0.6 equiv.) in 300 mL distilled (DI) water was added dropwise over four hours to a stirring solution of $Na_2CO_3 \cdot H_2O$ (6.2 g, 0.05 mol, 1 equiv.) in 375 mL distilled water. The pH was kept constant at pH ~10 by adding aliquots of 1 M NaOH aqueous solution. Upon completion of the addition, the mixture was allowed to stir vigorously at room temperature for three days. The blue precipitate was collected by vacuum filtration and washed with 1.5 L distilled water. The filter cake was then suspended in a solution of $Na_2CO_3$ solution (62 g, 0.5 mol, 10 equiv.) in DI $H_2O$ (250 mL, 2M) and allowed to stir at room temperature overnight. Upon completion, the precipitate was collected by vacuum filtration and washed with DI $H_2O$ (2.5 L). The filter was left to dry overnight in a 105° C.

oven to obtain copper-doped hydrotalcite. The solid was ground by mortar and pestle and subjected to calcination at 460° C. in air for 24 h to obtain Cu-PMO (9.21 g) as a green powder. The Cu-PMO was analyzed by XRPD (FIG. 5), showing the expected loss of hydrotalcite features. Elemental analysis of Cu-PMO was performed by ICP-OES (Table 2) and confirms incorporation of the metals in the expected ratio.

TABLE 2

Metal Ion Composition of Cu-PMO determined by ICP-OES

| | Cu | Mg | Al |
|---|---|---|---|
| Concentration (mg/L) | 26.09 | 39.37 | 19.36 |
| Mass in solution (mg) | 1.305 | 1.969 | 0.968 |
| Amount in solution (mmol) | 0.0205 | 0.0806 | 0.0359 |
| Normalized Ratio of Metals | 0.57 | 2.25 | 1.00 |

B. Synthesis of the Hydrotalcite (HTC) Catalyst

Figure 6:
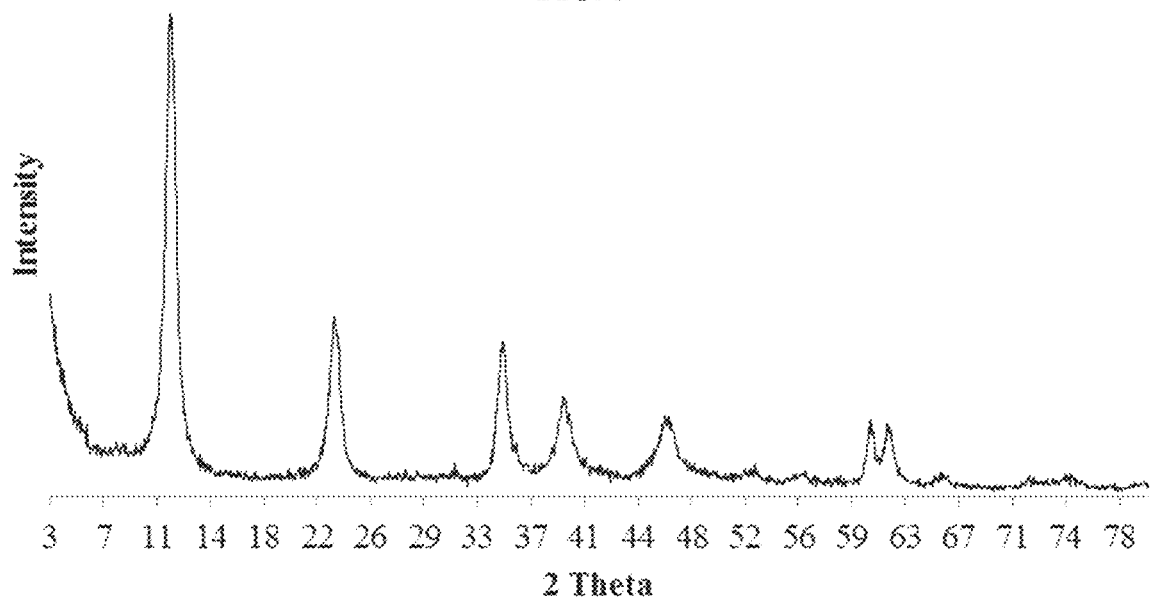
FIG. 6 illustrates a XRPD spectrum of the HTC catalyst.

A solution of Al(NO$_3$)$_3$.9H$_2$O (18.8 g, 0.05 mol, 1 equiv.) and Mg(NO$_3$)$_2$.6H$_2$O (38.46 g, 0.15 mol, 3 equiv.) in 300 mL distilled (DI) water was added dropwise over four hours to a stirring solution of Na$_2$CO$_3$.H$_2$O (6.2 g, 0.05 mol, 1 equiv.) in 375 mL distilled water. The pH was kept constant at pH ~10 by adding aliquots of 1 M NaOH aqueous solution. Upon completion of the addition, the mixture is allowed to stir vigorously at 40° C. for three days. The white precipitate is collected by vacuum filtration and washed with 1.5 L distilled water. The filter cake is then suspended in a solution of Na$_2$CO$_3$ solution (62 g, 0.5 mol, 10 equiv.) in DI H$_2$O (250 mL, 2M) and allowed to stir at 40° C. overnight. Upon completion, the precipitate is collected by vacuum filtration and washed with DI H$_2$O (2.5 L). The filter is left to dry overnight in a 105° C. oven to obtain hydrotalcite (HTC). The HTC was analyzed by XRPD (FIG. 6) and is identical to literature reports (Villadsen, et al., 2017, ChemBioChem 18:574-612).

C. Synthesis of Lubineau's Ketone 1b

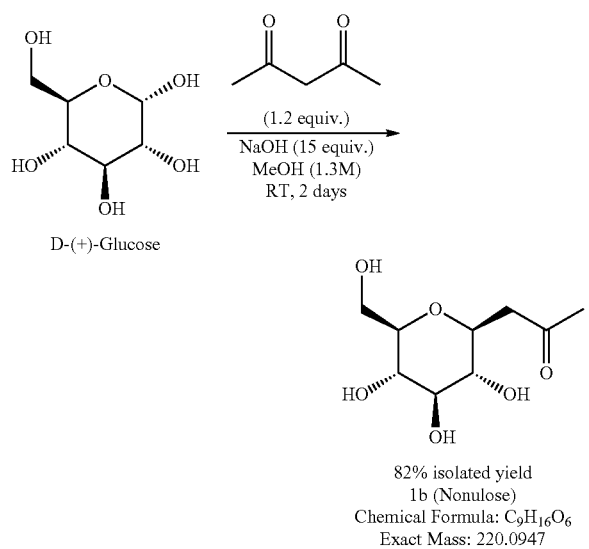

Synthesis of Nonulose 1b was performed according to a modified procedure by Cavezza et al. (Lalitha, et al., 2015, Carbohydr. Res. 402:158-171). D-(+)-Glucose (10 g, 55.51 mmol, 1 equiv.) and 2,4-pentanedione (6.8 mL, 6.65 g, 66.53 mmol, 1.2 equiv.) were added to a 100 mL round bottom flask equipped with a Teflon coated stir bar. MeOH (20.7 mL) was added by syringe. A solution of NaOH (3.33 g, 83.25 mmol, 15 equiv.) in MeOH (22 mL) and H$_2$O (10 mL) was prepared. After full dissolution of NaOH, the solution was added to the round bottom flask by pouring. The mixture was allowed to stir at room temperature for two days. Upon completion, the flask was placed in an ice bath and the basic mixture was quenched by dropwise addition of concentrated HCl (6.8 mL). The resulting crude mixture was evaporated in vacuo to obtain the crude product. Column chromatography (silica gel, EtOAc:MeOH:H$_2$O, 30:8:2) furnished pure product 1b as a brown oil in 82% yield (11.284 g, 45.46 mmol).

R$_f$=0.14 (silica gel, 8:1 DCM:MeOH); $^1$H NMR (400 MHz, CD$_3$OD) δ 3.77 (dd, J=12.0, 2.1 Hz, 1H), 3.61 (ddd, J=20.2, 10.6, 5.7 Hz, 2H), 3.37-3.17 (m, 3H), 3.05 (t, J=9.1 Hz, 1H), 2.86 (dd, J=16.0, 3.0 Hz, 1H), 2.57 (dd, J=16.0, 9.1 Hz, 1H), 2.18 (s, 3H). $^{13}$C NMR (101 MHz, CD$_3$OD) δ 208.83, 80.24, 78.19, 75.84, 73.69, 70.30, 61.38, 45.76, 29.19. Analytical data is identical to that reported in Gonzalez, et al., 1986, Carbohydr. Res. 158:53-66.

D. General Procedure a for Synthesis of C-Glycosidic Substrates 2a-g

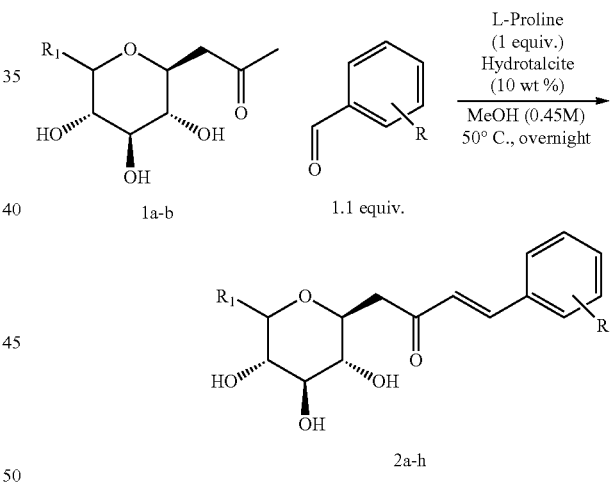

The procedure developed by de Winter et al. was replicated with alterations to afford targeted substrates (Auge & Lubin-Germain, 2014, Carbohydr. Chem. 40:11-30). The hygroscopicity of the starting material varied the true amount weighed out. Hence, an internal standard (biphenyl) was utilized to quantify amount of starting material added by $^1$H NMR, which is used to correct product yields. It follows that this variation in starting material content affects the relative amounts of reagents and reactants. C-glycoside ketone 1a-b (1 equiv.) was added to a round bottom flask equipped with a Teflon coated stir bar. MeOH (0.45 M) and biphenyl (0.05 equivalents, internal standard) were added by syringe and the mixture was stirred until complete dissolution of the starting material. An aliquot was removed and analyzed by $^1$H NMR to determine the amount of C-glycoside 1a-b added. L-Proline (1 equiv.), benzylic aldehyde (1.1 equiv.) and MgO (10 wt % of C-glycoside) were added to the stirring mixture. The reaction was allowed to proceed at 50° C. with stirring until completion as observed by TLC analysis. The mixture was filtered over filter paper, then mixed with silica gel and concentrated in vacuo. Crude product was purified over a short-path silica plug, after dry loading, by first flushing the internal standard (biphenyl) and excess aldehyde with a small amount of ethyl acetate, then collecting product with acetone as liquid phase.

E. General Procedure B for Synthesis of C-Glycosidic Substrates 2i-j

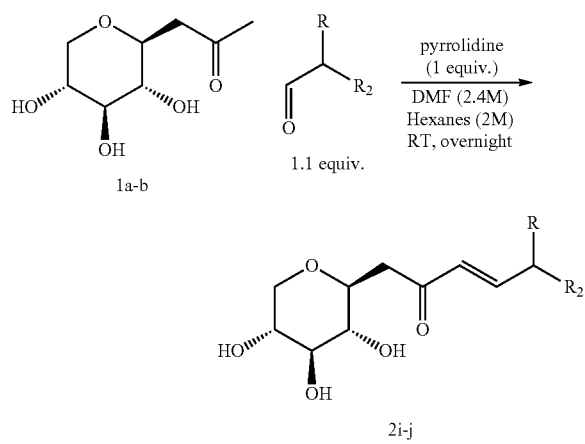

The procedure developed by Foley et al. was replicated with minor alterations to afford aliphatic C-glycosidic enones (Rodrigues, et al., 2000, Chem. Commun. 0:2049-2050). C-glycoside ketone 1a (1 equiv.) and biphenyl (0.05 equiv., internal standard) were added to a round bottom flask equipped with a Teflon coated stir bar. DMF (2.4 M) was added by syringe and the mixture was stirred until complete dissolution of the starting material. An aliquot was removed for $^1$H NMR analysis of starting material amount. Then, hexanes (2 M), pyrrolidine (1 equiv.) and aliphatic aldehyde (1 equiv.) were added to the stirring mixture. The reaction was allowed to proceed at room temperature with stirring until completion as observed by TLC analysis. The mixture was treated with Amberlite IR-120 H+ resin, filtered, and concentrated in vacuo. Crude product was purified by column chromatography (silica gel, 450:50 DCM:MeOH).

F. Optimized General Procedure C for Full Catalytic Hydrogenation of C-Glycosidic Enones 2a-j

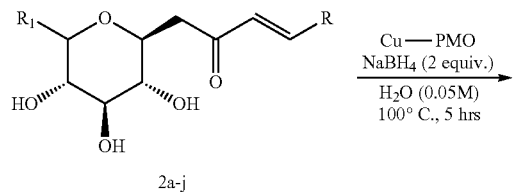

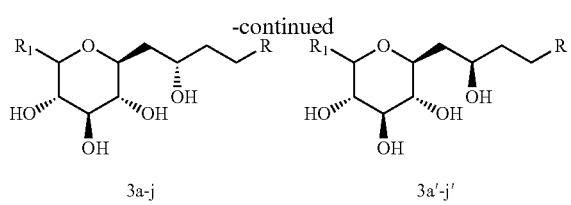

C-glycosidic enone 2a-j (0.5 mmol, 1 equiv.) was added to a 25 mL round-bottom flask equipped with a Teflon coated stir bar. $H_2O$ (10 mL, 0.05 M) was added by syringe. Cu-PMO (see below section 1i. for amounts) and $NaBH_4$ (37.8 mg, 1.0 mmol, 2 equiv.) were added to the mixture in single portions. The mixture was allowed to stir at reflux (100° C.) for 5 hours. Upon completion, the mixture was cooled and treated with Amberlite IR-120 H+ resin. The heterogeneous mixture was filtered over cellulose filter paper and the retentate was washed with methanol (~20 mL). The combined organic fractions were concentrated in vacuo. $CHCl_3$ (0.04 mL, 59.69 mg, 0.5 mmol, 1 equiv., internal standard) were added to the residue, and the mixture was completely dissolved in deuterated methanol for $^1$H and $^{11}$B NMR analysis. If boron salts were present, the mixture was re-dissolved in methanol and evaporated in vacuo, and the process was repeated until the absence of boron salts was confirmed by NMR. Once the NMR yield was obtained and the absence of boron salts was confirmed by NMR, the mixture was evaporated in vacuo and placed under high vacuum before weighing (if complete conversion to desired product). When desired, produced diastereomers were separated by column chromatography (silica gel, 450:50 DCM:MeOH).

G. Procedures and Amounts for Enone Full Reduction (c.f. Table 1)

Optimization of the reduction of enone under $H_2$ pressure was performed according to the following representative procedure D: C-Glycosidic enone 2a (1 equiv.) was added to a 100 mL stainless-steel Parr reactor. $NaBH_4$, and Cu-PMO catalyst were added to the Parr reactor (see Table 3 for amounts). Solvent was added to the reactor by syringe. The reactor was closed once all reaction components were added and subsequently pressurized under $H_2$ pressure. The reactor was placed on a stand and connected to a temperature controller. Heating was turned on at time t=0. The reaction was allowed to stir for the targeted amount of time (see Table 3). Upon completion, the reactor was cooled to room temperature under a stream of water. Once cool, the reactor was depressurized and opened in a fumehood. Flammable gas is then released. The mixture was treated with Amberlite IR-120H+ resin and filtered over cellulose paper before concentrating in vacuo. DMF or $CHCl_3$ (1 equiv., internal standard) was added to the residue, and the mixture was completely dissolved in deuterated methanol for $^1$H NMR analysis.

Optimization of the reduction of enone without $H_2$ pressure was performed according to the following representative procedure E: C-glycosidic enone 2a (1 equiv.) was added to a 25 mL round-bottom flask equipped with a Teflon coated stir bar. Solvent was added by syringe. $NaBH_4$ and Cu-PMO catalyst were added to the mixture in single portions. The mixture was allowed to stir at the chosen temperature for a set amount of time (Table 3). Upon completion, the mixture was brought to room temperature and treated with Amberlite IR-120 H+ resin. The heterogeneous mixture was filtered over cellulose filter paper and the retentate was washed with methanol. The combined organic fractions were concentrated in vacuo. DMF or CHCl$_3$ (1 equiv., internal standard) was added to the residue, and the mixture was completely dissolved in deuterated methanol for $^1$H NMR analysis.

deuterated methanol for $^1$H and $^{11}$B NMR analysis. Once the NMR yield was obtained and the absence of boron salts was confirmed by NMR, the mixture was evaporated in vacuo and placed under high vacuum before weighing to obtain the isolated yield. The recovered catalyst was placed in a dessicator until further use.

TABLE 3

Amounts in each reaction towards the Cu-catalyzed full reduction of enones (c.f. Table 1)

| Entry from Table 1 | Compound 2a | Catalyst | Additive | Solvent | Internal Standard |
|---|---|---|---|---|---|
| 1 | 0.3 mmol, 83.5 mg | Cu-PMO 10 mg | NaBH$_4$ (0.6 mmol, 22.7 mg) | MeOH (30 mL, 0.01M) | DMF (23 μL, 1 eq.) |
| 2 | 1.5 mmol, 417.5 mg | Cu-PMO 55 mg | NaBH$_4$ (3.0 mmol, 113.5 mg) | MeOH (30 mL, 0.05M) | DMF (110 μL, 1 eq.) |
| 3 | 1.5 mmol, 417.5 mg | Cu-PMO 55 mg | NaBH$_4$ (3.0 mmol, 113.5 mg) | MeOH (30 mL, 0.05M) | DMF (110 μL, 1 eq.) |
| 4 | 1.5 mmol, 417.5 mg | Cu-PMO 55 mg | NaBH$_4$ (3.0 mmol, 113.5 mg) | MeOH (30 mL, 0.05M) | DMF (110 μL, 1 eq.) |
| 5 | 1.5 mmol, 417.5 mg | Cu-PMO 55 mg | NaBH$_4$ (3.0 mmol, 113.5 mg) | MeOH (30 mL, 0.05M) | DMF (110 μL, 1 eq.) |
| 6 | 0.725 mmol, 201.8 mg | Cu-PMO 26.5 mg | NaBH$_4$ (1.45 mmol, 55 mg) | H$_2$O (14.5 mL, 0.05M) | DMF (56 μL, 1 eq.) |
| 7 | 1.5 mmol, 417.5 mg | Cu-PMO 55 mg | NaBH$_4$ (3.0 mmol, 113.5 mg) | H$_2$O (30 mL, 0.05M) | DMF (110 μL, 1 eq.) |

H. Procedure for Large-Scale Reduction of Aromatic Enone 2e

C-glycosidic enone 2e (8.12 g, 25 mmol, 1 equiv.) and water (500 ml, 0.05 M) were charged to a 1 L double-jacketed reactor equipped with a mechanical stirrer. To this suspension were added Cu-PMO (892 mg, 11 mol %) and NaBH$_4$ (1.89 g, 50 mmol, 2 equiv.) in single portions. The reaction mixture was allowed to stir at reflux (100° C.) for 5 hours. Upon completion, the dark brown homogeneous solution was cooled and treated with Amberlite IR-120 H+ resin (~180 g). The suspension was filtered over cellulose filter paper and the retentate was washed with methanol (~1 L). The combined organic and aqueous fractions were evaporated to dryness under vacuum. The crude residue was purified by filtration over silica (eluting with EtOAc:MeOH 80:20), followed by a carbon black treatment at reflux in ethanol for one hour. After concentration in vacuo, the solid was diluted with water, filtered, and lyophilized, furnishing pure product 3e (mixture of diastereomers) as a beige powder in 72.9% isolated yield (6 g, 18.27 mmol). $^1$H and $^{13}$C NMR data are consistent with those from the smaller scale results reported in Section I.

I. Catalyst Recycling Studies

C-glycosidic enone 2e (162.2 mg, 0.5 mmol, 1 equiv.) was added to a 25 mL round-bottom flask equipped with a Teflon coated stir bar. H$_2$O (10 mL, 0.05 M) was added by syringe. Cu-PMO (Trial 1: 16.5 mg, 10 wt % and afterwards as recovered from previous run) and NaBH$_4$ (37.8 mg, 1.0 mmol, 2 equiv.) were added to the mixture in single portions. The mixture was allowed to stir at reflux (100° C.) for 5 hours. Upon completion, the mixture was cooled and treated with Amberlite IR-120 H+ resin. The heterogeneous mixture was filtered over cellulose filter paper and the retentate was washed with methanol (~20 mL). The combined organic fractions were concentrated in vacuo. CHCl$_3$ (0.04 mL, 59.69 mg, 0.5 mmol, 1 equiv., internal standard) were added to the residue, and the mixture was completely dissolved in

TABLE 4

Product yields after catalyst recycling

| | 2e Conversion[a] (%) | NMR Yield 3e/3e'[a] (%) | Isolated Yield 3e/3e' (%) |
|---|---|---|---|
| Cycle 1 | 100 | >95 | 93 |
| Cycle 2 | 100 | 94 | 97 |
| Cycle 3 | 100 | >95 | 85 |
| Cycle 4 | 100 | >95 | 92 |
| Cycle 5 | 100 | >95 | 93 |

[a]Conversion and NMR yields determined by $^1$H NMR using CHCl$_3$ as internal standards.

J. Amberlite IR-120H$^+$ Regeneration and Reuse

Amberlite IR-120 H+ can be recuperated after reaction through a simple vacuum filtration. After recuperation, Amberlite IR-120 H$^+$ can be reused after treatment to regenerate its acidity. To do so, spent Amberlite IR-120 H+ is placed in an Erlenmeyer containing a Teflon coated stir bar. The solid was covered with concentrated sulfuric acid and allowed to stir at room temperature for 30 minutes. After completion, the resin was filtered out of the solution and washed with DI water. The resin was placed in a dessicator for further drying until use.

Use of recycled resin did not alter reduction results. 2a (0.5 mmol) was reduced using our optimized conditions with Cu-PMO (11 wt %) and NaBH$_4$ (2 equiv.) in MeOH (0.05 M) at 100° C. for 5 hours. After completion, recycled Amberlite IR-120 H$^+$ resin was added to the mixture to acidify until pH=5. The mixture was filtered, washed with MeOH, and evaporated in vacuo to generate product 3a, as a diastereomeric mixture, in >95% NMR yield.

K. Substrates Syntheses, Isolations and Characterizations

1. C-Glycosidic Aromatic Enones 2a-h

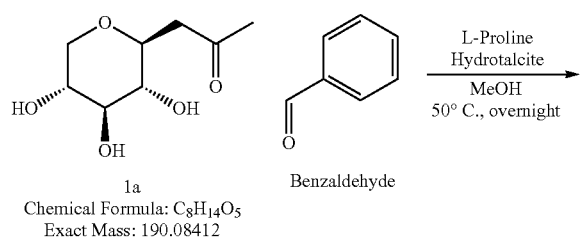

1a
Chemical Formula: C$_8$H$_{14}$O$_5$
Exact Mass: 190.08412

Benzaldehyde

L-Proline
Hydrotalcite
MeOH
50° C., overnight

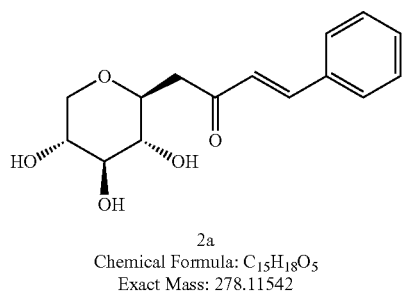

2a
Chemical Formula: C$_{15}$H$_{18}$O$_5$
Exact Mass: 278.11542

2a was synthesized following general procedure A with Octulose 1a (1125 mg, 5.918 mmol), benzaldehyde (0.85 mL, 921.1 mg, 8.68 mmol), L-Proline (908.5 mg, 7.891 mmol), biphenyl (61.4 mg, internal standard), and MgO (150 mg) in methanol (17.5 mL). Crude product was isolated from internal standard, L-proline and excess aldehyde by short path silica plug (EtOAc, then acetone) to obtain 2a as an off-white solid in 85% isolated yield.

R$_f$=0.32 (silica gel, 8:1 DCM:MeOH); $^1$H NMR (400 MHz, CD$_3$OD) δ 7.65-7.56 (m, 3H), 7.42-7.33 (m, 3H), 6.84 (d, J=16.3 Hz, 1H), 3.77 (dd, J=11.1, 5.4 Hz, 1H), 3.64 (t, J=9.4, 1H), 3.42 (dd, J=10.5, 8.9, 1H), 3.27 (t, J=3.2, 1H), 3.17-3.02 (m, 3H), 2.84 (dd, J=15.8, 9.2 Hz, 1H); $^{13}$C NMR (151 MHz, CD$_3$OD) δ 199.98, 143.97, 135.11, 130.85, 129.19, 128.67, 126.66, 78.95, 77.65, 74.31, 70.67, 70.18, 43.36. HR-MS (ESI$^+$, m/z): Calcd for C$_{14}$H$_9$O$_5$ [M+H]$^+$ 279.12325 Found 279.12345. Analytical data is identical to that reported in Anastas & Warner, *Green Chemistry: Theory and Practice*, Oxford University Press, Oxford, 1998.

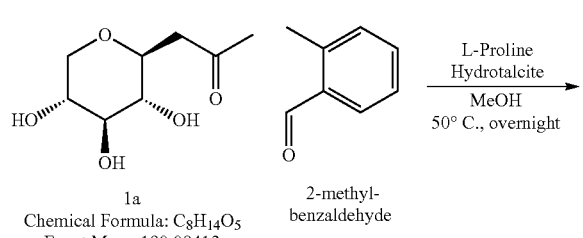

1a
Chemical Formula: C$_8$H$_{14}$O$_5$
Exact Mass: 190.08412

2-methyl-benzaldehyde

L-Proline
Hydrotalcite
MeOH
50° C., overnight

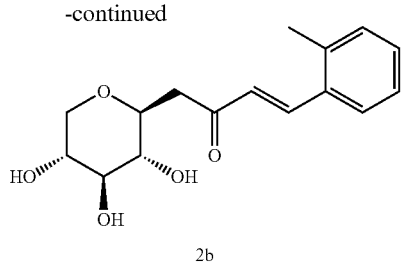

2b
Chemical Formula: C$_{16}$H$_{20}$O$_5$
Exact Mass: 292.13107

2b was synthesized following general procedure A with Octulose 1a (324.9 mg, 1.710 mmol), 2-methylbenzaldehyde (0.34 mL, 347.23 mg, 2.89 mmol), L-Proline (302.8 mg, 2.63 mmol), biphenyl (23.6 mg, 0.123 mmol) and MgO (50 mg) in methanol (5.8 mL). Crude product was isolated from internal standard, L-proline and excess aldehyde by short path silica plug (Ethyl acetate, then acetone) to obtain 2b as a yellow oil in 86% isolated yield.

R$_f$=0.36 (silica gel, 8:1 DCM:MeOH); $^1$H NMR (400 MHz, CD$_3$OD) δ 7.93 (d, J=16.0 Hz, 1H), 7.63 (d, J=7.6 Hz, 1H), 7.34-7.24 (m, 1H), 7.24-7.11 (m, 2H), 6.77 (d, J=16.0 Hz, 1H), 3.80 (dd, J=11.1, 5.4 Hz, 1H), 3.66 (td, J=9.4, 2.5 Hz, 1H), 3.49-3.40 (m, 1H), 3.33-3.24 (m, 1H), 3.19-3.05 (m, 3H), 2.84 (dd, J=15.8, 9.2 Hz, 1H), 2.42 (s, 3H). $^{13}$C NMR (101 MHz, CD$_3$OD) δ 199.43, 140.75, 137.97, 133.17, 130.43, 130.06, 126.92, 126.09, 126.01, 78.34, 77.13, 73.69, 70.07, 69.61, 43.09, 18.29. HR-MS (ESI$^+$, m/z): Calcd for C$_{16}$H$_{21}$O$_5$ [M+H]$^+$ 293.13890 Found 293.13829.

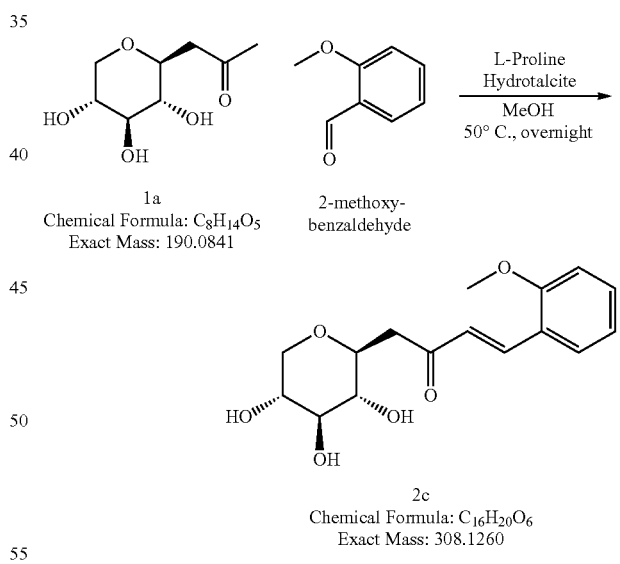

1a
Chemical Formula: C$_8$H$_{14}$O$_5$
Exact Mass: 190.0841

2-methoxy-benzaldehyde

L-Proline
Hydrotalcite
MeOH
50° C., overnight

2c
Chemical Formula: C$_{16}$H$_{20}$O$_6$
Exact Mass: 308.1260

2c was synthesized following general procedure A with Octulose 1a (349.9 mg, 1.841 mmol), 2-methoxybenzaldehyde (0.35 mL, 394 mg, 2.89 mmol), L-Proline (302.8 mg, 2.63 mmol), biphenyl (21.0 mg, 0.136 mmol, internal standard) and MgO (50 mg) in methanol (5.8 mL). Crude product was isolated from internal standard, L-proline and excess aldehyde by short path silica plug (Ethyl acetate, then acetone) to obtain 2c as a brown solid in 77% isolated yield.

R$_f$=0.60 (silica gel, 8:1 DCM:MeOH); $^1$H NMR (400 MHz, CD$_3$OD) δ 7.94 (d, J=16.4 Hz, 1H), 7.61 (dd, J=7.7, 1.7 Hz, 1H), 7.38 (ddd, J=8.8, 7.4, 1.7 Hz, 1H), 7.03 (dd, J=8.5, 1.0 Hz, 1H), 6.96 (td, J=7.5, 1.0 Hz, 1H), 6.89 (d, J=16.3 Hz, 1H), 3.89 (s, 3H), 3.83-3.75 (m, 2H), 3.66 (td, J=9.4, 2.5 Hz, 1H), 3.44 (ddd, J=10.6, 9.0, 5.4 Hz, 1H), 3.20-3.02 (m, 3H), 2.82 (dd, J=15.9, 9.3 Hz, 1H). $^{13}$C NMR (101 MHz, CD$_3$OD) δ 199.78, 158.65, 138.52, 131.86, 128.16, 126.18, 122.92, 120.43, 111.02, 78.34, 77.05, 73.70, 70.08, 69.59, 54.68, 42.76. HR-MS (ESI$^+$, m/z): Calcd for C$_{16}$H$_{21}$O$_6$ [M+H]$^+$ 309.13381 Found 309.13310.

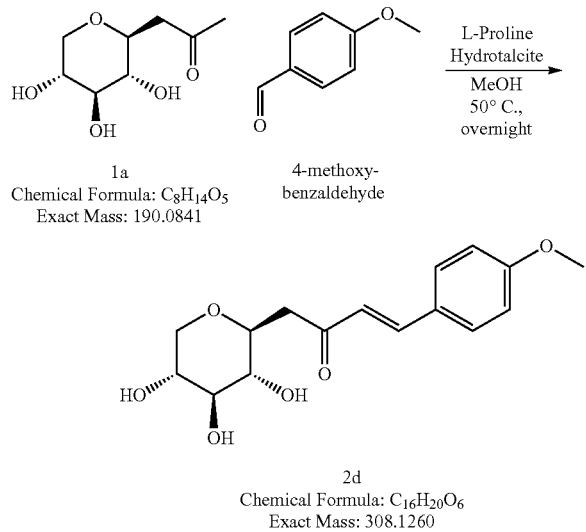

1a
Chemical Formula: C$_8$H$_{14}$O$_5$
Exact Mass: 190.0841

4-methoxy-benzaldehyde

L-Proline
Hydrotalcite
MeOH
50° C.,
overnight

2d
Chemical Formula: C$_{16}$H$_{20}$O$_6$
Exact Mass: 308.1260

2d was synthesized following general procedure A with Octulose 1a (349.9 mg, 1.841 mmol), 4-methoxybenzaldehyde (0.35 mL, 394 mg, 2.89 mmol), L-Proline (302.8 mg, 2.63 mmol), biphenyl (20.3 mg, 0.132 mmol, internal standard) and MgO (50 mg) in methanol (5.8 mL). Crude product was isolated from internal standard, L-proline and excess aldehyde by short path silica plug (Ethyl acetate, then acetone) to obtain 2d as an off-white solid in 79% isolated yield.

R$_f$=0.34 (silica gel, 8:1 DCM:MeOH); $^1$H NMR (400 MHz, CD$_3$OD) δ 7.64-7.52 (m, 3H), 6.94 (dd, J=9.1, 2.5 Hz, 2H), 6.72 (d, J=16.1, 1H), 3.83-3.71 (m, 4H), 3.64 (td, J=9.4, 2.5 Hz, 1H), 3.53-3.40 (m, 1H), 3.30-3.21 (m, 1H), 3.19-2.98 (m, 3H), 2.87-2.73 (m, 1H); $^{13}$C NMR (151 MHz, CD$_3$OD) δ 199.75, 162.17, 143.79, 130.21, 127.19, 123.98, 114.31, 78.61, 77.37, 73.97, 70.32, 69.80, 54.74, 42.89. HR-MS (ESI$^+$, m/z): Calcd for C$_{16}$H$_{21}$O$_6$ [M+H]$^+$ 309.13381 Found 309.13324. Analytical data is identical to that reported in Cipolla, et al., 2002, Biorg. Med. Chem. 10:1639-1646.

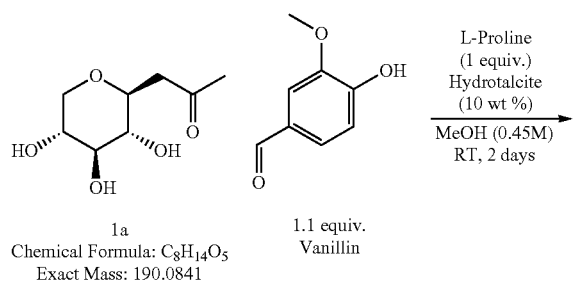

1a
Chemical Formula: C$_8$H$_{14}$O$_5$
Exact Mass: 190.0841

1.1 equiv.
Vanillin

L-Proline
(1 equiv.)
Hydrotalcite
(10 wt %)
MeOH (0.45M)
RT, 2 days

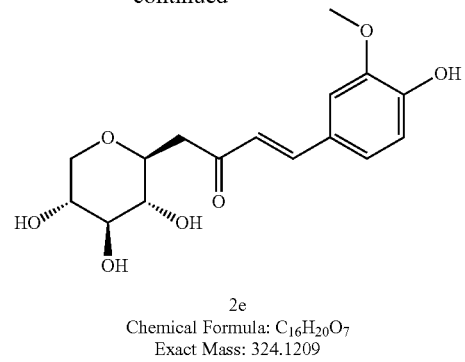

2e
Chemical Formula: C$_{16}$H$_{20}$O$_7$
Exact Mass: 324.1209

2e was synthesized following general procedure A with Octulose 1a (1500 mg, 7.891 mmol, 1 equiv.), vanillin (1320.2 mg, 8.68 mmol, 1.1 equiv.), L-Proline (908.5 mg, 7.891 mmol, 1 equiv.) and HTC (150 mg, 10 wt %) in methanol (17.5 mL). Pure product precipitated out of the reaction mixture and was filtered to obtain 2e as an off-white solid in 63% isolated yield.

R$_f$=0.24 (silica gel, 8:1 DCM:MeOH); $^1$H NMR (400 MHz, CD$_3$OD) δ 7.57 (d, J=16.1 Hz, 1H), 7.21 (d, J=1.9 Hz, 1H), 7.11 (dd, J=8.2, 2.0 Hz, 1H), 6.80 (d, J=8.2 Hz, 1H), 6.71 (d, J=16.1 Hz, 1H), 3.88 (s, 3H), 3.79 (dd, J=11.1, 5.4 Hz, 1H), 3.65 (td, J=9.4, 2.6 Hz, 1H), 3.44 (ddd, J=10.5, 8.9, 5.3 Hz, 1H), 3.29 (p, J=1.6 Hz, 1H), 3.17-3.00 (m, 3H), 2.82 (dd, J=15.7, 9.3 Hz, 1H). $^{13}$C NMR (101 MHz, CD$_3$OD) δ 199.58, 147.98, 144.38, 126.30, 123.26, 123.13, 115.11, 110.42, 78.36, 77.20, 73.76, 70.08, 69.58, 54.97, 42.58. HR-MS (ESI$^+$, m/z): Calcd for C$_{16}$H$_{21}$O$_7$ [M+H]$^+$ 325.12873 Found 325.12751. Analytical data is identical to that reported in Cipolla, et al., 2002, Biorg. Med. Chem. 10:1639-1646.

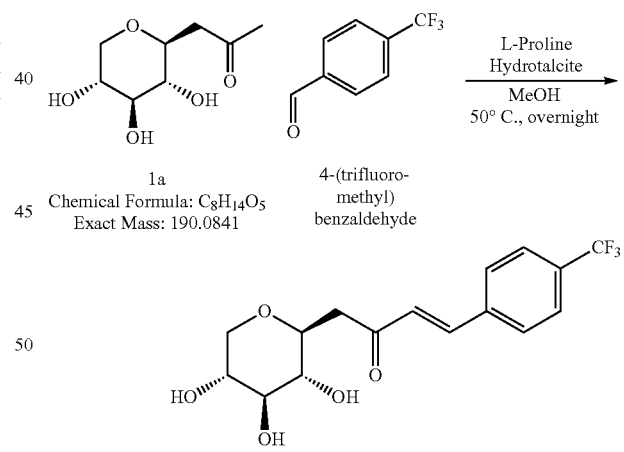

1a
Chemical Formula: C$_8$H$_{14}$O$_5$
Exact Mass: 190.0841

4-(trifluoro-methyl)benzaldehyde

L-Proline
Hydrotalcite
MeOH
50° C., overnight

2f
Chemical Formula: C$_{16}$H$_{17}$F$_3$O$_5$
Exact Mass: 346.1028

2f was synthesized following general procedure A with Octulose 1a (624.9 mg, 3.285 mmol), 4-trifluoromethylbenzaldehyde (0.67 mL, 854.3 mg, 4.906 mmol), L-Proline (506.6 mg, 4.400 mmol), biphenyl (19.8 mg, 0.128 mmol, internal standard) and MgO (50 mg) in methanol (9.8 mL). Crude product was isolated from internal standard, L-proline and excess aldehyde by short path silica plug (Ethyl acetate, then acetone) to obtain 2f as a brown solid in 71% isolated yield.

$R_f$=0.37 (silica gel, 8:1 DCM:MeOH); $^1$H NMR (400 MHz, CD$_3$OD) δ 7.81 (d, J=8.1 Hz, 2H), 7.72-7.61 (m, 3H), 6.97 (d, J=16.3 Hz, 1H), 3.79 (dd, J=11.1, 5.4 Hz, 1H), 3.67 (td, J=9.4, 2.7 Hz, 1H), 3.44 (ddd, J=10.5, 8.9, 5.4 Hz, 1H), 3.20-3.05 (m, 4H), 2.87 (dd, J=15.9, 9.2 Hz, 1H). $^{13}$C NMR (151 MHz, CD$_3$OD) δ 199.01, 141.04, 138.41, 138.40, 128.51, 131.61, 131.39, 131.18, 130.96, 128.48, 125.48, 125.44, 125.41, 125.39, 78.35, 76.98, 73.70, 70.07, 69.60, 43.01. HR-MS (ESI$^+$, m/z): Calcd for C$_{16}$H$_{18}$F$_3$O$_5$ [M+H]$^+$ 347.11063 Found 347.10976.

NMR (151 MHz, CD$_3$OD) δ 199.14, 162.30, 160.63, 135.03, 135.01, 132.07, 132.01, 128.76, 128.74, 128.21, 128.17, 124.49, 124.47, 122.31, 122.24, 115.72, 115.58, 78.33, 76.99, 73.67, 70.06, 69.59, 43.09. HR-MS (ESI$^+$, m/z): Calcd for C$_{15}$H$_{18}$FO$_5$ [M+H]$^+$ 297.11383 Found 297.11360.

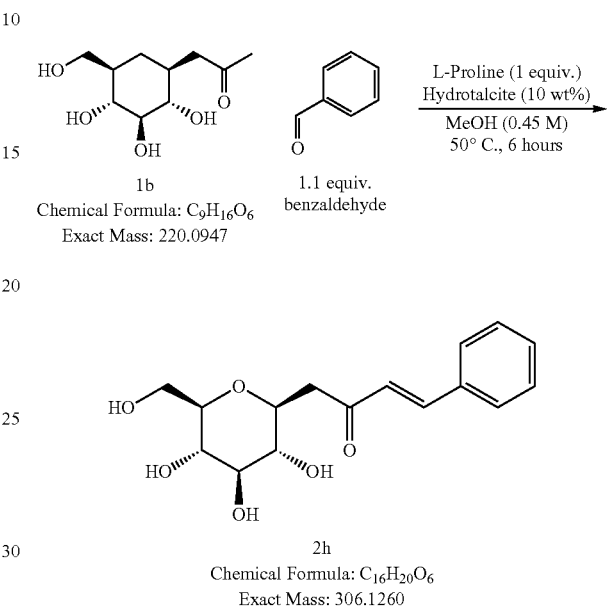

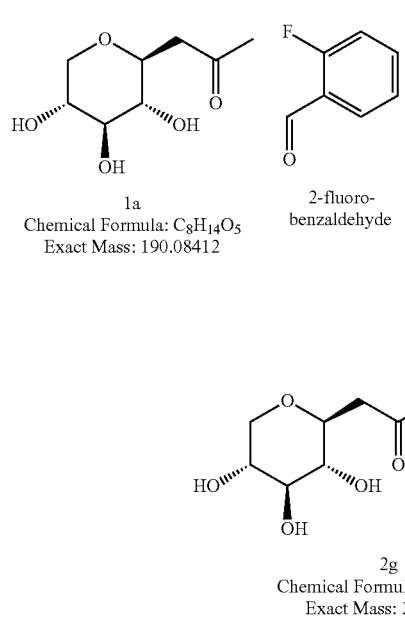

2g was synthesized following general procedure A with Octulose 1a (500 mg, 2.63 mmol), 2-fluorobenzaldehyde (0.45 mL, 530.1 mg, 4.271 mmol), L-Proline (455 mg, 3.952 mmol), biphenyl (19.9 mg, 0.128 mmol, internal standard) and MgO (75 mg) in methanol (8.8 mL). Crude product was isolated from internal standard, L-proline and excess aldehyde by short path silica plug (Ethyl acetate, then acetone) to obtain 2g as a yellow solid in 93% isolated yield.

$R_f$=0.37 (silica gel, 8:1 DCM:MeOH); $^1$H NMR (400 MHz, CD$_3$OD) δ 7.76-7.68 (m, 2H), 7.43 (dddd, J=8.5, 7.2, 5.3, 1.7 Hz, 1H), 7.25-7.11 (m, 2H), 6.94 (d, J=16.3 Hz, 1H), 3.79 (dd, J=11.1, 5.4 Hz, 1H), 3.66 (td, J=9.4, 2.6 Hz, 1H), 3.44 (ddd, J=10.5, 8.9, 5.4 Hz, 1H), 3.29 (dt, J=3.1, 1.5 Hz, 1H), 3.17-3.04 (m, 3H), 2.83 (dd, J=15.9, 9.2 Hz, 1H). $^{13}$C 2h was synthesized following general procedure A with Nonulose 1b (106.3 mg, 0.483 mmol), benzaldehyde (0.23 mL, 235 mg, 2.21 mmol), L-Proline (232 mg, 2.01 mmol), biphenyl (16.4 mg, 0.106 mmol, internal standard) and MgO (50 mg) in methanol (4.5 mL). Crude product was isolated from internal standard, L-proline and excess aldehyde by short path silica plug (Ethyl acetate, then acetone) to obtain 2h as a beige powder in 66% isolated yield.

$R_f$=0.18 (silica gel, 9:1 DCM:MeOH); $^1$H NMR (400 MHz, CD$_3$OD) δ 7.67-7.61 (m, 3H), 7.42-7.37 (m, 3H), 6.90 (d, J=16.2 Hz, 1H), 3.80-3.71 (m, 2H), 3.64-3.58 (m, 1H), 3.38-3.31 (m, 2H), 3.21 (ddd, J=9.3, 5.1, 2.3 Hz, 1H), 3.18-3.06 (m, 2H), 2.89 (dd, J=15.9, 8.9 Hz, 1H). $^{13}$C NMR (101 MHz, CD$_3$OD) δ 199.56, 143.40, 134.56, 130.24, 128.59, 128.10, 126.03, 80.19, 78.29, 76.03, 73.70, 70.24, 61.3, 42.92. Analytical data is identical to that reported in Auge & Lubin-Germain, 2014, Carbohydr. Chem. 40:11-30.

2. Aliphatic C-glycosidic Enones 21-j

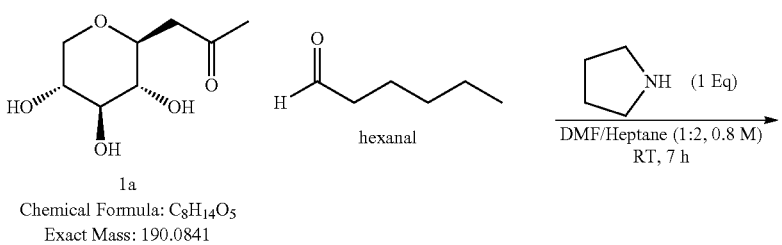

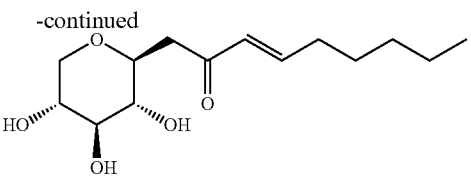

Chemical Formula: $C_{14}H_{24}O_5$
Exact Mass: 272.1624

2i was synthesized following general procedure B with Octulose 1a (1000 mg, 5.26 mmol, 1 equiv.), pyrrolidine (0.44 mL, 374.1 mg, 5.26 mmol, 1 equiv.) and hexanal (0.64 mL, 526.8 mg, 5.26 mmol, 1 equiv.) in hexanes (2.68 mL) and DMF (2.2 mL) at room temperature overnight. The crude mixture was purified by column chromatography (silica gel, DCM:MeOH, 450:50) to afford 2i as an orange oil in 36% yield.

$R_f$=0.43 (silica gel, 8:1 DCM:MeOH); $^1$H NMR (400 MHz, CD$_3$OD) δ 6.91 (dt, J=15.8, 7.0 Hz, 1H), 6.13 (dt, J=15.9, 1.5 Hz, 1H), 3.76 (dd, J=11.1, 5.4 Hz, 1H), 3.58 (td, J=9.4, 2.5 Hz, 1H), 3.42 (ddd, J=10.6, 8.9, 5.4 Hz, 1H), 3.31-3.21 (m, 1H), 3.14-3.02 (m, 2H), 2.99-2.89 (m, 1H), 2.71 (dd, J=15.9, 9.3 Hz, 1H), 2.28-2.19 (m, 2H), 1.54-1.43 (m, 2H), 1.42-1.23 (m, 4H), 0.97-0.85 (m, 3H). $^{13}$C NMR (101 MHz, CD$_3$OD) δ 201.24, 150.63, 131.87, 79.99, 78.59, 75.30, 71.71, 71.21, 43.61, 33.74, 32.74, 29.12, 23.71, 14.54. HR-MS (ESI$^+$, m/z): Calcd for $C_{14}H_{25}O_5$ [M+H]$^+$ 273.17020 Found 273.16922.

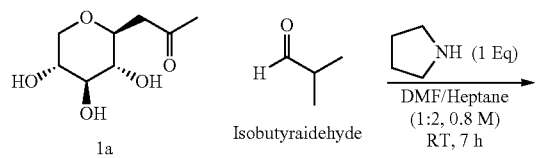

1a
Chemical Formula: $C_8H_{14}O_5$
Exact Mass: 190.0841

Isobutyraldehyde

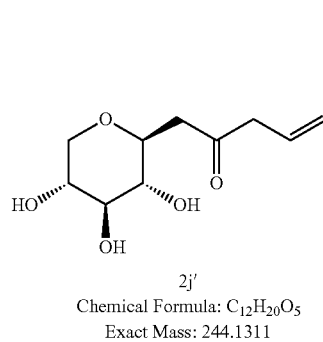

2j'
Chemical Formula: $C_{12}H_{20}O_5$
Exact Mass: 244.1311

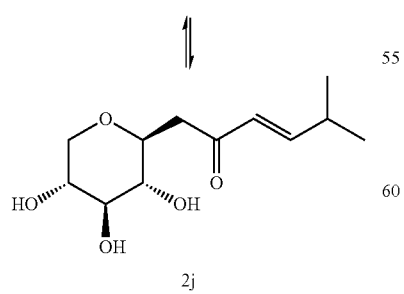

2j 2j was synthesized following general procedure B with Octulose 1a (250 mg, 1.315 mmol, 1 equiv.), pyrrolidine (0.11 mL, 93.5 mg, 1.315 mmol, 1 equiv.) and isobutyraldehyde (0.12 mL, 94.8 mg, 1.315 mmol, 1 equiv.) in heptane (0.66 mL) and DMF (0.55 mL) at room temperature overnight. The crude mixture was purified by column chromatography (silica gel, DCM:MeOH, 450:50) to afford 2j (mixture of trans isomer 2j and deconjugated isomer 2j') as an orange oil in 70% yield. HR-MS (ESI$^+$, m/z): Calcd for $C_{12}H_{21}O_5$ [M+H]$^+$ 245.13890 Found 245.13824.

2j: $R_f$=0.5 (silica gel, 8:1 DCM:MeOH); $^1$H NMR (400 MHz, CD$_3$OD) δ 6.87 (dd, J=16.0, 6.8 Hz, 1H), 6.09 (dd, J=16.0, 1.4 Hz, 1H), 3.77 (dt, J=11.1, 5.5 Hz, 1H), 3.57 (dtd, J=14.5, 9.4, 2.7 Hz, 1H), 3.41 (dddd, J=10.7, 8.9, 5.4, 1.9 Hz, 1H), 3.24 (dt, J=8.9, 4.5 Hz, 1H), 3.08 (m, 2H), 2.94 (dd, J=16.0, 2.5 Hz, 1H), 2.72 (dd, J=16.0, 9.3 Hz, 1H), 2.59-2.42 (m, 1H), 1.07 (d, J=6.8 Hz, 6H). $^{13}$C NMR (101 MHz, CD$_3$OD) δ 201.26, 156.10, 128.85, 79.77, 78.29, 75.07, 71.48, 70.99, 43.49, 32.44, 21.62.

2j': $R_f$=0.5 (silica gel, 8:1 DCM:MeOH); $^1$H NMR (400 MHz, CD$_3$OD) δ 5.26 (dddd, J=8.6, 7.2, 2.9, 1.5 Hz, 1H), 3.77 (dt, J=11.1, 5.5 Hz, 1H), 3.57 (dtd, J=14.5, 9.4, 2.7 Hz, 1H), 3.41 (dddd, J=10.7, 8.9, 5.4, 1.9 Hz, 1H), 3.17 (d, J=7.3 Hz, 2H), 3.08 (m, 2H) 2.83 (dd, J=15.9, 2.9 Hz, 1H), 2.59-2.42 (m, 1H), 1.67 (dd, J=46.4, 1.4 Hz, 6H). $^{13}$C NMR (101 MHz, CD$_3$OD) δ 210.04, 136.69, 117.02, 79.71, 78.18, 75.05, 71.46, 70.97, 45.83, 44.04, 25.83, 18.08.

3. C-Glycosidic Alcohols 3a-j and 3a'-j'

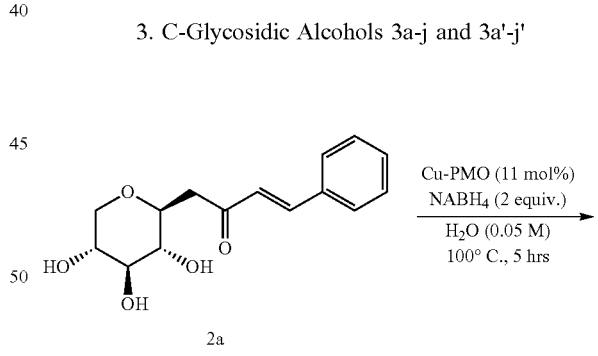

2a
Chemical Formula: $C_{15}H_{18}O_5$
Exact Mass: 278.1154

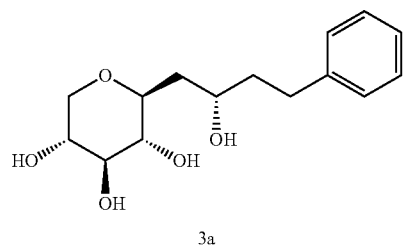

3a
Chemical Formula: $C_{15}H_{22}O_5$
Exact Mass: 282.1467

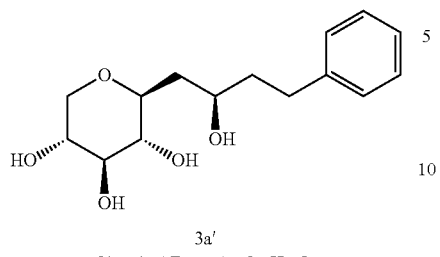

3a'
Chemical Formula: C₁₅H₂₂O₅
Exact Mass: 282.1467

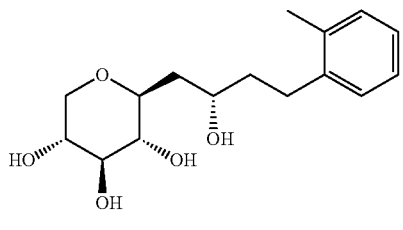

3b
Chemical Formula: C₁₆H₂₄O₅
Exact Mass: 296.1624

3a and 3a' were synthesized following general procedure C with 2a (139.2 mg, 0.5 mmol, 1 equiv.), Cu-PMO (16.5 mg, 11 mol %) and NaBH₄ (37.8 mg, 1.0 mmol, 2 equiv.) in H₂O (10 mL) at reflux for 5 hours. The mixture containing only 3a and 3a' was fully dissolved in MeOD and an internal standard (CHCl₃, 40 µL, 1 equiv.) was added to obtain the NMR yield. Boron NMR was measured to verify the absence of boron salts in the crude mixture. After evaporation in vacuo, the product was weighed to show 89% isolated yield. The diastereomers were separated by column chromatography (silica gel, DCM:MeOH, 450:50) to afford 3a and 3a' as clear oils in 10% yield for each.

Mixture HR-MS (ESI⁺, m/z): Calcd for C₁₅H₂₃O₅ [M+H]⁺ 283.15455 Found 283.15364. 3a R_f=0.6 (silica gel, 8:1 DCM:MeOH, developed with CAM); ¹H NMR (400 MHz, CD₃OD) δ 7.26-7.15 (m, 5H), 3.82 (dd, J=11.1, 5.6 Hz, 3H), 3.51-3.37 (m, 1H), 3.37-2.95 (m, 2H), 2.76 (ddd, J=15.1, 10.0, 5.3 Hz, 2H), 2.62 (ddd, J=13.6, 9.8, 6.5 Hz, 2H), 2.01 (ddd, J=14.4, 5.9, 2.8 Hz, 1H), 1.78 (dddd, J=14.1, 10.4, 6.4, 4.1 Hz, 1H), 1.59 (ddd, J=15.0, 9.0, 6.6 Hz, 1H); ¹³C NMR (101 MHz, CD₃OD) δ 142.25, 128.00, 127.89, 125.26, 78.95, 78.30, 74.37, 70.02, 69.49, 68.71, 39.19, 38.42, 31.36. HR-MS (ESI⁺, m/z): Calcd for C₁₅H₂₂O₅ [M+H]⁺ 283.15455 Found 283.15347.

3a' R_f=0.49 (silica gel, 8:1 DCM:MeOH, developed with CAM); ¹H NMR (400 MHz, CD₃OD) 7.22 (t, J=7.5 Hz, 2H), 7.17 (d, J=6.7 Hz, 2H), 7.14-7.07 (m, 1H), 3.87-3.70 (m, 2H), 3.43 (ddd, J=11.0, 9.0, 5.4 Hz, 1H), 3.38-3.20 (m, 2H), 3.12 (t, J=10.9 Hz, 1H), 3.00 (t, J=9.1 Hz, 1H), 2.80-2.54 (m, 2H), 1.92 (ddd, J=14.8, 9.9, 2.3 Hz, 1H), 1.76-1.66 (m, 2H), 1.45 (ddd, J=14.7, 9.6, 2.5 Hz, 1H); ¹³C NMR (101 MHz, CD₃OD) 142.25, 127.99, 127.87, 125.24, 78.49, 77.21, 74.33, 70.21, 69.48, 66.67, 39.73, 39.67, 31.65. HR-MS (ESI⁺, m/z): Calcd for C₁₅H₂₂O₅ [M+H]⁺ 283.15455 Found 283.15411.

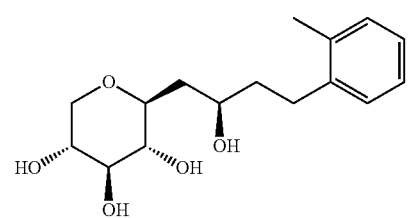

3b'
Chemical Formula: C₁₆H₂₄O₅
Exact Mass: 296.1624

3b and 3b' were synthesized following general procedure C with 2b (146.2 mg, 0.5 mmol, 1 equiv.), Cu-PMO (16.5 mg, 11 mol %) and NaBH₄ (37.8 mg, 1.0 mmol, 2 equiv.) in H₂O (10 mL) at reflux for 5 hours. The crude mixture containing only 3b and 3b' was fully dissolved in MeOD and an internal standard (CHCl₃, 40 µL, 1 equiv.) was added to obtain the NMR yield. Boron NMR was measured to verify the absence of boron salts in the crude mixture. After evaporation in vacuo, the product was weighed to show quantitative yield. The diastereomers were separated by column chromatography (silica gel, DCM:MeOH, 450:50) to afford 3b and 3b' as clear oils in 17.6% and 4.5%, respectively.

Mixture HR-MS (ESI⁺, m/z): Calcd for C₁₆H₂₅O₅ [M+H]⁺ 297.17020 Found 297.16939.

3b R_f=0.32 (silica gel, 8:1 DCM:MeOH); ¹H NMR (400 MHz, CD₃OD) δ 7.05 (dqd, J=19.4, 8.0, 7.2, 3.8 Hz, 4H), 3.84 (td, J=11.3, 5.9 Hz, 2H), 3.43 (ddd, J=10.5, 8.8, 5.3 Hz, 1H), 3.27-3.16 (m, 2H), 3.15-2.99 (m, 2H), 2.76 (ddd, J=14.0, 10.6, 5.2 Hz, 1H), 2.61 (ddd, J=13.8, 10.5, 6.0 Hz, 1H), 2.37-2.30 (m, 1H), 2.28 (s, 3H), 2.02 (ddd, J=14.4, 6.0, 2.8 Hz, 1H), 1.72 (tdd, J=14.9, 7.2, 4.1 Hz, 1H), 1.61 (ddt, J=17.9, 9.4, 6.5 Hz, 2H). ¹³C NMR (101 MHz, CD₃OD) δ 140.28, 135.40, 129.62, 128.39, 125.51, 125.41, 78.94, 78.29, 74.37, 70.02, 69.51, 69.01, 39.14, 37.09, 28.72, 17.95. HR-MS (ESI⁺, m/z): Calcd for C₁₆H₂₃O₅Na [M+Na]⁺ 319.15214 Found 319.13670.

3b' R_f=0.23 (silica gel, 8:1 DCM:MeOH); ¹H NMR (400 MHz, CD₃OD) δ 7.12-6.99 (m, 4H), 3.82 (dddd, J=14.6, 9.1, 6.6, 3.6 Hz, 2H), 3.44 (dddd, J=12.7, 7.7, 5.4, 2.3 Hz, 1H), 3.38-3.06 (m, 4H), 3.05-2.97 (m, 1H), 2.75 (dt, J=13.7, 8.2 Hz, 1H), 2.61 (dt, J=13.6, 8.0 Hz, 1H), 2.31 (d, J=2.7 Hz, 1H), 2.28 (s, 3H), 2.00-1.87 (m, 1H), 1.70-1.58 (m, 2H), 1.47 (ddd, J=14.4, 9.7, 2.6 Hz, 1H). ¹³C NMR (101 MHz, CD₃OD) δ 140.26, 135.38, 129.64, 128.43, 125.53, 125.43, 78.44, 77.17, 74.32, 70.20, 69.48, 66.98, 39.63, 38.47, 29.01, 17.97. HR-MS (ESI⁺, m/z): Calcd for C₁₆H₂₄O₅ [M+H]⁺ 297.17020 Found 297.17004.

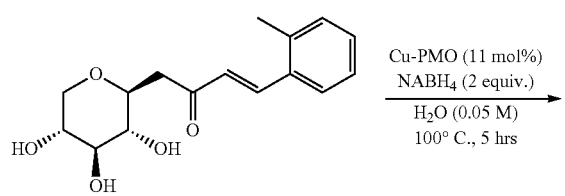

2b
Chemical Formula: C₁₆H₂₀O₅
Exact Mass: 292.1311

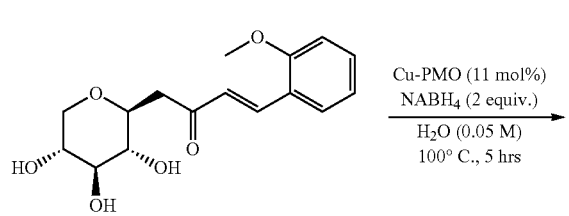

2c
Chemical Formula: C₁₆H₂₀O₆
Exact Mass: 308.1260

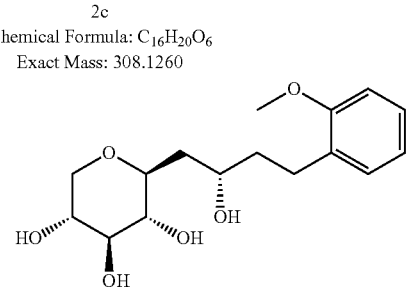

3c
Chemical Formula: C₁₆H₂₄O₆
Exact Mass: 312.1573

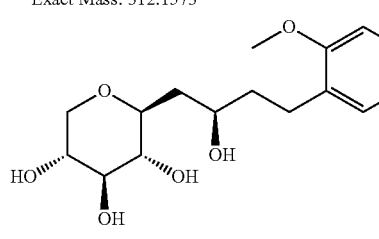

3c'
Chemical Formula: C₁₆H₂₄O₆
Exact Mass: 312.1573

3c and 3c' were synthesized following general procedure C with 2c (154.2 mg, 0.5 mmol, 1 equiv.), Cu-PMO (16.5 mg, 11 mol %) and NaBH₄ (37.8 mg, 1.0 mmol, 2 equiv.) in H₂O (10 mL) at reflux for 5 hours. The mixture containing only 3c and 3c' was fully dissolved in MeOD and an internal standard (CHCl₃, 40 µL, 1 equiv.) was added to obtain the NMR yield. Boron NMR was measured to verify the absence of boron salts in the crude mixture. After evaporation in vacuo, the product was weighed to show quantitative yield. The diastereomers were separated by column chromatography (silica gel, DCM:MeOH, 450:50) to afford 3c and 3c' as clear oils in 22% and 35% yield, respectively.

Mixture HR-MS (ESI⁺, m/z): Calcd for C₁₆H₂₅O₆ [M+H]⁺ 313.16511 Found 313.16422. 3c R$_f$=0.41 (silica gel, 8:1 DCM:MeOH); ¹H NMR (400 MHz, CD₃OD) δ 7.15-7.06 (m, 2H), 6.89-6.84 (m, 1H), 6.81 (td, J=7.4, 1.1 Hz, 1H), 3.85-3.74 (m, 5H), 3.43 (ddd, J=10.6, 8.9, 5.4 Hz, 1H), 3.27-3.14 (m, 2H), 3.06 (dt, J=17.3, 10.0 Hz, 2H), 2.75 (ddd, J=13.5, 10.1, 5.4 Hz, 1H), 2.60 (ddd, J=13.4, 9.9, 6.2 Hz, 1H), 2.01 (ddd, J=14.3, 5.8, 2.9 Hz, 1H), 1.75 (dddd, J=14.2, 10.4, 6.2, 4.4 Hz, 1H), 1.68-1.51 (m, 2H). ¹³C NMR (101 MHz, CD₃OD) δ 157.43, 130.27, 129.40, 126.68, 120.00, 109.94, 79.05, 78.30, 74.38, 70.02, 69.51, 69.14, 54.28, 39.08, 36.61, 25.98. HR-MS (ESI⁺, m/z): Calcd for C₁₆H₂₄O₆ [M+H]⁺ 313.16511 Found 313.14989.

3c' R$_f$=0.38 (silica gel, 8:1 DCM:MeOH); ¹H NMR (400 MHz, CD₃OD) δ 7.16-7.05 (m, 2H), 6.88-6.84 (m, 1H), 6.81 (td, J=7.4, 1.1 Hz, 1H), 3.86-3.73 (m, 5H), 3.44 (ddd, J=10.6, 8.9, 5.4 Hz, 1H), 3.37-3.20 (m, 2H), 3.13 (t, J=10.8 Hz, 1H), 3.06-2.96 (m, 1H), 2.78-2.66 (m, 1H), 2.60 (dt, J=13.5, 7.7 Hz, 1H), 1.91 (ddd, J=14.5, 10.0, 2.4 Hz, 1H), 1.73-1.60 (m, 2H), 1.47 (ddd, J=14.5, 9.7, 2.5 Hz, 1H). ¹³C NMR (101 MHz, CD₃OD) δ 157.40, 130.25, 129.40, 126.68, 120.00, 109.94, 78.48, 77.21, 74.36, 70.21, 69.47, 67.04, 54.28, 39.59, 37.99, 26.24. HR-MS (ESI⁺, m/z): Calcd for C₁₆H₂₄O₆ [M+H]⁺ 313.16511 Found 313.16446.

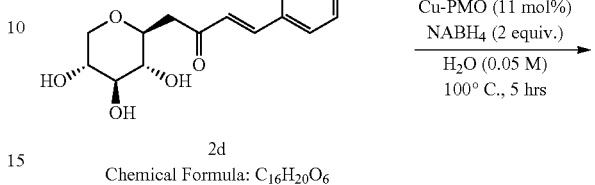

2d
Chemical Formula: C₁₆H₂₀O₆
Exact Mass: 308.1260

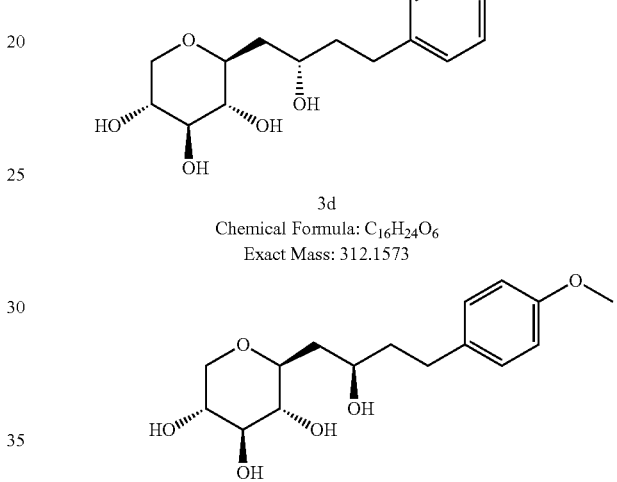

3d
Chemical Formula: C₁₆H₂₄O₆
Exact Mass: 312.1573

3d'
Chemical Formula: C₁₆H₂₄O₆
Exact Mass: 312.1573

3d and 3d' were synthesized following general procedure C with 2d (308.33 mg, 1.0 mmol, 1 equiv.), Cu-PMO (33 mg, 11 mol %) and NaBH₄ (75.6 mg, 2.0 mmol, 2 equiv.) in H₂O (20 mL) at reflux for 5 hours. The crude mixture containing only 3d and 3d' was fully dissolved in MeOD and an internal standard (CHCl₃, 80 µL, 1 equiv.) was added to obtain the NMR yield. Boron NMR was measured to verify the absence of boron salts in the crude mixture. After evaporation in vacuo, the product was weighed to show quantitative yield. The diastereomers were separated by column chromatography (silica gel, DCM:MeOH, 450:50) to afford 3d and 3d' as clear oils in 14% and 30% yield, respectively. Mixture HR-MS (ESI⁺, m/z): Calcd for C₁₆H₂₅O₆ [M+H]⁺ 313.16511 Found 313.16428.

3d R$_f$=0.55 (silica gel, 8:1 DCM:MeOH); ¹H NMR (400 MHz, CD₃OD) δ 7.11-7.06 (m, 2H), 6.82-6.76 (m, 2H), 3.80 (ddd, J=13.7, 10.3, 4.3 Hz, 2H), 3.73 (s, 3H), 3.42 (ddd, J=10.5, 9.0, 5.4 Hz, 1H), 3.25-3.15 (m, 2H), 3.10 (d, J=10.9 Hz, 1H), 3.08-2.98 (m, 1H), 2.69 (ddd, J=13.7, 10.0, 5.3 Hz, 1H), 2.56 (ddd, J=13.7, 9.8, 6.5 Hz, 1H), 1.99 (ddd, J=14.4, 5.9, 2.8 Hz, 1H), 1.81-1.53 (m, 3H). ¹³C NMR (101 MHz, CD₃OD) δ 157.80, 134.18, 128.86, 113.29, 78.94, 78.26, 74.37, 70.01, 69.49, 68.63, 54.18, 39.20, 38.58, 30.42. HR-MS (ESI⁺, m/z): Calcd for C₁₆H₂₄O₆ [M+H]⁺ 313.16511 Found 313.16445.

3d' $R_f$=0.45 (silica gel, 8:1 DCM:MeOH); $^1$H NMR (400 MHz, CD$_3$OD) δ 7.12-7.02 (m, 2H), 6.86-6.73 (m, 2H), 3.88-3.73 (m, 2H), 3.43 (ddd, J=10.5, 8.9, 5.4 Hz, 1H), 3.37-3.21 (m, 3H), 3.12 (t, J=10.8 Hz, 1H), 3.00 (t, J=9.1 Hz, 1H), 2.74-2.63 (m, 1H), 2.56 (dt, J=13.8, 8.2 Hz, 1H), 1.99-1.82 (m, 1H), 1.67 (td, J=8.1, 5.8 Hz, 2H), 1.44 (ddd, J=14.5, 9.7, 2.6 Hz, 1H). $^{13}$C NMR (101 MHz, CD$_3$OD) δ 157.78, 134.18, 128.88, 113.30, 78.45, 77.15, 74.32, 70.20, 69.47, 66.53, 54.19, 39.94, 39.69, 30.73. HR-MS (ESI$^+$, m/z): Calcd for C$_{16}$H$_{24}$O$_6$ [M+H]$^+$ 313.16511 Found 313.16386.

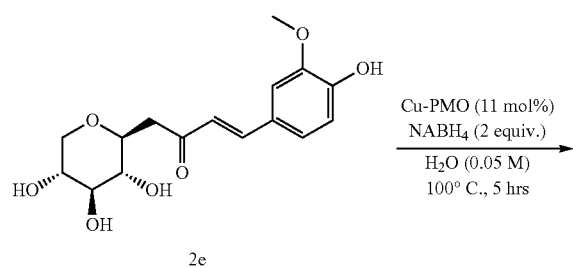

2e
Chemical Formula: C$_{16}$H$_{20}$O$_7$
Exact Mass: 324.1209

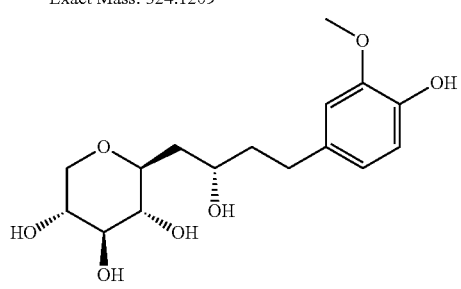

3e
Chemical Formula: C$_{16}$H$_{24}$O$_7$
Exact Mass: 328.1522

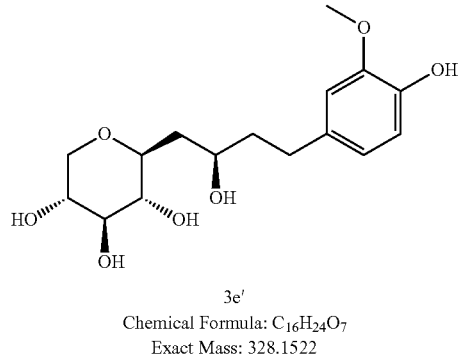

3e'
Chemical Formula: C$_{16}$H$_{24}$O$_7$
Exact Mass: 328.1522

3e and 3e' were synthesized following general procedure C with 2e (162.2 mg, 0.5 mmol, 1 equiv.), Cu-PMO (16.5 mg, 11 mol %) and NaBH$_4$ (37.8 mg, 1.0 mmol, 2 equiv.) in H$_2$O (10 mL) at reflux for 5 hours. The crude mixture containing only 3e and 3e' was fully dissolved in MeOD and an internal standard (CHCl$_3$, 40 µL, 1 equiv.) was added to obtain the NMR yield. Boron NMR was measured to verify the absence of boron salts in the crude mixture. After evaporation in vacuo, the product was weighed to show 93% isolated yield. Attempts to separate diastereomers by column chromatography (silica gel, 15:4:1 EtOAc:MeOH:H$_2$O), precipitation/recrystallization and preparatory thin layer chromatography (silica gel, 9:1 DCM:MeOH) were unsuccessful. Characterization data reported below is assessed from analysis of a mixture of 3e and 3e'. Mixture HR-MS (ESI$^+$, m/z): Calcd for C$_{16}$H$_{25}$O$_7$ [M+H]$^+$ 329.16003 Found 329.15889.

3e $R_f$=0.64 (silica gel, 15:4:1 EtOAc:MeOH:H$_2$O); $^1$H NMR (400 MHz, CD$_3$OD) δ 6.73 (dd, J=3.3, 1.9 Hz, 1H), 6.68 (dd, J=8.0, 1.4 Hz, 1H), 6.60 (dt, J=8.0, 2.0 Hz, 1H), 3.90-3.73 (m, 5H), 3.52-3.39 (m, 1H), 3.31-2.98 (m, 4H), 2.66 (ddt, J=15.2, 10.1, 5.8 Hz, 1H), 2.53 (ddd, J=13.8, 9.0, 6.9 Hz, 1H), 2.01 (ddd, J=14.4, 5.8, 2.7 Hz, 1H), 1.81-1.53 (m, 3H). $^{13}$C NMR (101 MHz, CD$_3$OD) δ 147.35, 143.93, 133.84, 120.36, 114.67, 111.74, 78.97, 77.18, 74.32, 70.01, 69.48, 68.71, 66.61, 54.93, 39.29, 38.63, 30.94.

3e' $R_f$=0.64 (silica gel, 15:4:1 EtOAc:MeOH:H$_2$O); $^1$H NMR (400 MHz, CD$_3$OD) δ 6.73 (dd, J=3.3, 1.9 Hz, 1H), 6.68 (dd, J=8.0, 1.4 Hz, 1H), 6.60 (dt, J=8.0, 2.0 Hz, 1H), 3.90-3.73 (m, 5H), 3.52-3.39 (m, 1H), 3.31-2.98 (m, 4H), 2.66 (ddt, J=15.2, 10.1, 5.8 Hz, 1H), 2.53 (ddd, J=13.8, 9.0, 6.9 Hz, 1H), 1.96-1.86 (m, 1H), 1.81-1.53 (m, 2H), 1.47 (ddd, J=14.7, 9.7, 2.5 Hz, 1H). $^{13}$C NMR (101 MHz, CD$_3$OD) δ 147.34, 143.93, 133.84, 120.36, 114.67, 111.72, 78.45, 78.26, 74.36, 70.20, 69.48, 68.71, 54.95, 39.95, 39.65, 31.25.

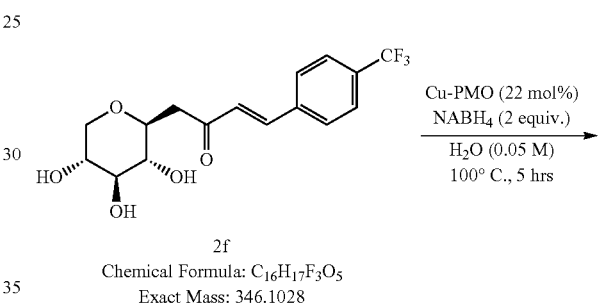

2f
Chemical Formula: C$_{16}$H$_{17}$F$_3$O$_5$
Exact Mass: 346.1028

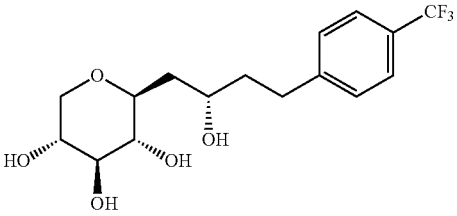

3f
Chemical Formula: C$_{16}$H$_{21}$F$_3$O$_5$
Exact Mass: 350.1341

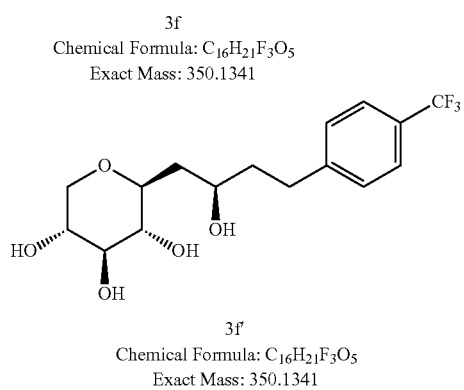

3f'
Chemical Formula: C$_{16}$H$_{21}$F$_3$O$_5$
Exact Mass: 350.1341

3f and 3f' were synthesized following general procedure C with 2f (173.15 mg, 0.5 mmol, 1 equiv.), Cu-PMO (33 mg, 22 mol %) and NaBH$_4$ (37.8 mg, 1.0 mmol, 2 equiv.) in H$_2$O (10 mL) at reflux for 5 hours. The crude mixture was fully dissolved in MeOD and an internal standard (CHCl$_3$, 40 µL, 1 equiv.) was added to obtain the NMR yield. Boron NMR was measured to verify the absence of boron salts in the crude mixture. After evaporation in vacuo, the product was weighed to show 87% isolated yield. Diastereomers were separated by column chromatography (silica gel, DCM:MeOH, 450:50) to afford 3f and 3f' as clear oils in 44% and 18% yield, respectively. Mixture HR-MS (ESI+, m/z): Calcd for $C_{16}H_{22}F_3O_5$ [M+H]+ 351.14193 Found 351.14087 3f $R_f$=0.31 (silica gel, 8:1 DCM:MeOH); $^1$H NMR (600 MHz, $CD_3OD$) δ δ 7.56-7.53 (m, 2H), 7.41-7.36 (m, 2H), 3.87-3.77 (m, 2H), 3.42 (ddd, J=10.6, 8.9, 5.4 Hz, 1H), 3.26-3.16 (m, 3H), 3.14-3.07 (m, 1H), 3.02 (dt, J=11.9, 9.4 Hz, 1H), 2.86 (ddd, J=14.7, 10.1, 5.0 Hz, 1H), 2.73 (ddd, J=13.7, 10.1, 6.7 Hz, 1H), 2.06-1.95 (m, 1H), 1.88-1.78 (m, 1H), 1.70 (dddd, J=13.6, 10.0, 8.4, 5.1 Hz, 1H), 1.60 (ddd, J=14.3, 9.1, 6.4 Hz, 1H). $^{13}$C NMR (151 MHz, $CD_3OD$) δ 147.06, 128.67, 124.78, 124.75, 124.73, 124.70, 78.76, 78.26, 74.37, 70.00, 69.48, 68.36, 39.20, 37.89, 31.15. HR-MS (ESI+, m/z): Calcd for $C_{16}H_{22}F_3O_5$ [M+H]+ 351.14193 Found 351.14106.

3f' $R_f$=0.38 (silica gel, 8:1 DCM:MeOH); $^1$H NMR (400 MHz, $CD_3OD$) δ 7.53 (d, J=8.1 Hz, 2H), 7.37 (d, J=8.0 Hz, 2H), 3.86-3.72 (m, 2H), 3.43 (ddd, J=10.6, 9.0, 5.3 Hz, 1H), 3.37-3.19 (m, 2H), 3.18-3.07 (m, 1H), 3.00 (t, J=9.1 Hz, 1H), 2.91-2.80 (m, 1H), 2.72 (dt, J=13.8, 8.1 Hz, 1H), 1.94 (ddd, J=14.5, 10.0, 2.4 Hz, 1H), 1.80-1.68 (m, 2H), 1.45 (ddd, J=14.4, 9.8, 2.7 Hz, 1H). $^{13}$C NMR (101 MHz, $CD_3OD$) δ 147.03, 128.68, 124.80, 124.77, 124.73, 124.69, 78.42, 77.09, 74.29, 70.18, 69.46, 66.40, 39.65, 39.24, 31.46. HR-MS (ESI+, m/z): Calcd for $C_{16}H_{22}F_3O_5$ [M+H]+ 351.14193 Found 351.14075.

3g and 3g' were synthesized following general procedure C with 2g (173.15 mg, 0.5 mmol, 1 equiv.), Cu-PMO (33 mg, 22 mol %) and NaBH$_4$ (37.8 mg, 1.0 mmol, 2 equiv.) in H$_2$O (10 mL) at reflux for 5 hours. The crude mixture containing 3g and 3g' was fully dissolved in MeOD and an internal standard (CHCl$_3$, 40 μL, 1 equiv.) was added to obtain the NMR yield. Boron NMR was measured to verify the absence of boron salts in the crude mixture. After evaporation in vacuo, the product was weighed to show 92% yield. The diastereomers were separated by column chromatography (silica gel, DCM:MeOH, 450:50) to afford 3g' as a clear oil in 1% yield. Unfortunately, diastereomer 3g could not be isolated separately from 3g'. Further optimization of separation of the diastereomers is required. Mixture HR-MS (ESI+, m/z): Calcd for $C_{15}H_{22}FO_5$ [M+1-1]+ 301.14513 Found 301.14436.

3g' $R_f$=0.52 (silica gel, 8:1 DCM:MeOH); $^1$H NMR (600 MHz, $CD_3OD$) δ 7.23 (td, J=7.6, 1.8 Hz, 1H), 7.16 (tdt, J=10.3, 7.0, 3.4 Hz, 1H), 7.05 (td, J=7.5, 1.3 Hz, 1H), 6.99 (ddd, J=9.8, 8.3, 1.2 Hz, 1H), 3.86-3.73 (m, 2H), 3.43 (ddd, J=10.6, 9.0, 5.3 Hz, 1H), 3.35-3.30 (m, 1H), 3.25 (t, J=8.9 Hz, 1H), 3.17-3.07 (m, 1H), 3.04-2.96 (m, 1H), 2.84-2.73 (m, 1H), 2.72-2.63 (m, 1H), 1.98-1.88 (m, 1H), 1.75-1.66 (m, 2H), 1.45 (ddd, J=14.4, 9.8, 2.6 Hz, 1H). $^{13}$C NMR (151 MHz, $CD_3OD$) δ 130.45, 130.41, 128.89, 128.79, 127.28, 127.22, 123.74, 123.71, 114.64, 114.49, 78.44, 77.10, 74.32, 70.20, 69.47, 66.65, 39.63, 38.18, 24.93, 24.91. HR-MS (ESI+, m/z): Calcd for $C_{15}H_{22}FO_5$ [M+1-1]+301.14513 Found 301.14439.

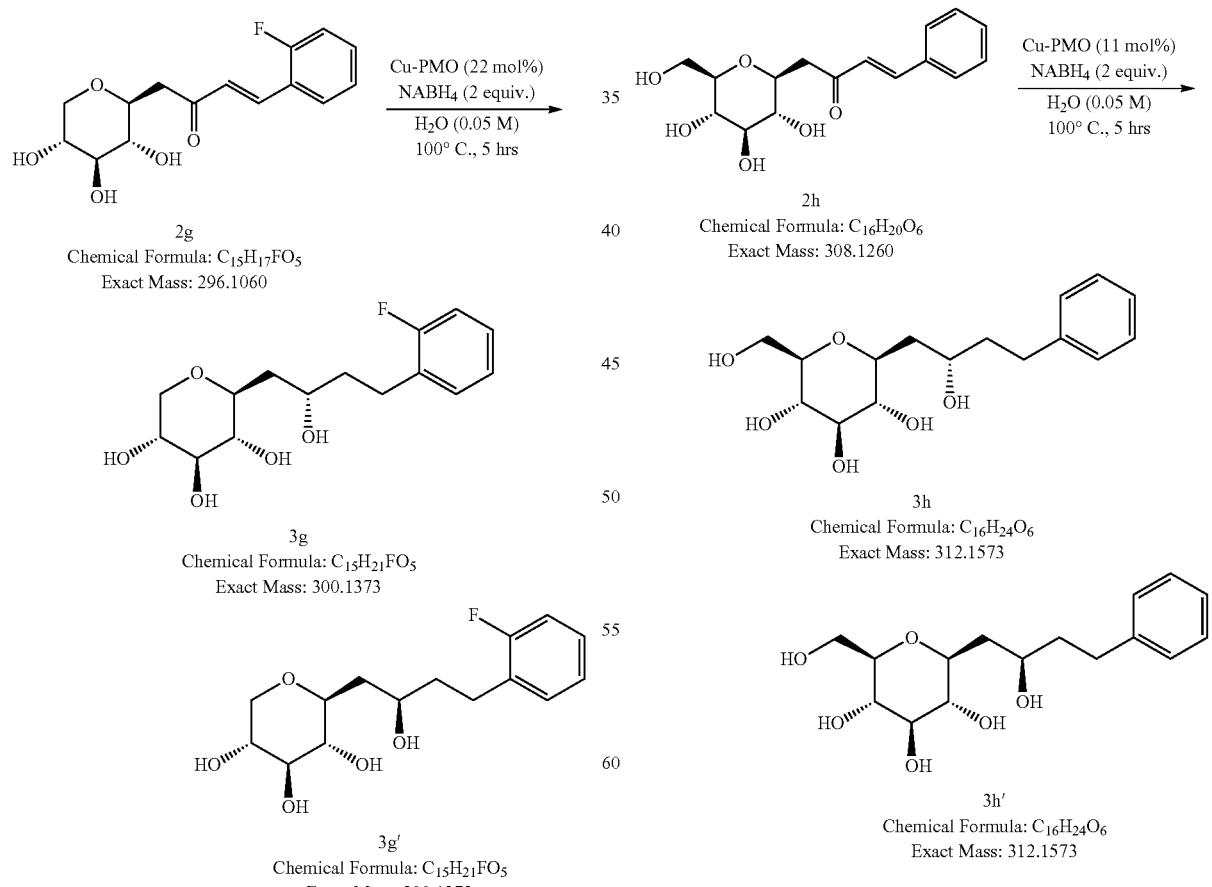

3h and 3h' were synthesized following general procedure C with 2h (154.2 mg, 0.5 mmol, 1 equiv.), Cu-PMO (16.5 mg, 11 wt %) and NaBH$_4$ (37.8 mg, 1.0 mmol, 2 equiv.) in H$_2$O (10 mL) at reflux for 5 hours. The crude mixture was fully dissolved in MeOD and an internal standard (CHCl$_3$, 40 µL, 1 equiv.) was added to obtain the NMR yield. Boron NMR was measured to verify the absence of boron salts in the crude mixture. After evaporation in vacuo, the product was weighed to show 92% yield. The diastereomers were separated by column chromatography (silica gel, DCM:MeOH, 450:50) to afford 3h and 3h' as clear oils in 11.7% and 36% yield, respectively. Mixture HR-MS (ESI$^+$, m/z): Calcd for C$_{15}$H$_{25}$O$_6$ [M+H]$^+$ 313.16511 Found 313.16428.

3h R$_f$=0.22 (silica gel, 8:1 DCM:MeOH); $^1$H NMR (400 MHz, CD$_3$OD) δ 7.25-7.14 (m, 4H), 7.12 (d, J=7.1 Hz, 1H), 3.90-3.71 (m, 2H), 3.57 (dd, J=11.8, 5.4 Hz, 1H), 3.31-3.15 (m, 4H), 3.06 (t, J=9.0 Hz, 1H), 2.76 (ddd, J=13.6, 10.1, 5.4 Hz, 1H), 2.63 (ddd, J=13.6, 9.8, 6.5 Hz, 1H), 2.09-1.96 (m, 1H), 1.85-1.64 (m, 2H), 1.60 (ddd, J=14.5, 9.2, 7.3 Hz, 1H). $^{13}$C NMR (101 MHz, CD$_3$OD) δ 142.26, 128.01, 127.89, 125.25, 80.20, 78.51, 78.21, 74.33, 70.48, 69.17, 61.61, 38.93, 38.67, 31.34. HR-MS (ESI$^+$, m/z): Calcd for C$_{15}$H$_{25}$O$_6$ [M+H]$^+$ 313.16511 Found 313.16406.

3h' R$_f$=0.18 (silica gel, 8:1 DCM:MeOH); $^1$H NMR (400 MHz, CD$_3$OD) δ 7.25-7.15 (m, 4H), 7.15-7.07 (m, 1H), 3.93-3.74 (m, 2H), 3.61 (dd, J=11.7, 5.2 Hz, 1H), 3.40 (td, J=9.5, 2.5 Hz, 1H), 3.36-3.18 (m, 3H), 3.04 (t, J=9.1 Hz, 1H), 2.77 (dt, J=13.5, 7.9 Hz, 1H), 2.62 (dt, J=13.6, 8.1 Hz, 1H), 1.93 (ddd, J=14.4, 9.9, 2.5 Hz, 1H), 1.72 (td, J=8.3, 6.4 Hz, 2H), 1.53 (ddd, J=14.4, 9.6, 2.6 Hz, 1H). $^{13}$C NMR (101 MHz, CD$_3$OD) δ 142.35, 128.00, 127.89, 125.25, 80.05, 78.39, 76.26, 74.30, 70.58, 66.65, 61.68, 39.73, 39.53, 31.78. HR-MS (ESI$^+$, m/z): Calcd for C$_{15}$H$_{25}$O$_6$ [M+H]$^+$ 313.16511 Found 313.16411.

material 2i present in a stock solution was verified by NMR using CHCl$_3$ (0.04 mL, 0.5 mmol) as internal standard. After reaction, the crude mixture fully dissolved in MeOD and an internal standard (CHCl$_3$, 40 µL, 1 equiv.) was added to obtain the NMR yield. Boron NMR was measured to verify the absence of boron salts in the crude mixture. After evaporation in vacuo, the product was weighed to show quantitative yield. The diastereomers were separated by column chromatography (silica gel, DCM:MeOH, 450:50) to afford 3i' as a clear oil in 8.2% yield. Unfortunately, diastereomer 3i could not be isolated separately from 3i'. Further optimization of separation of the diastereomers is required. Mixture HR-MS (ESI$^+$, m/z): Calcd for C$_{14}$H$_{28}$O$_5$Na [M+Na]$^+$ 299.18344 Found 299.14731.

3i' R$_f$=0.42 (silica gel, 8:1 DCM:MeOH); $^1$H NMR (400 MHz, CD$_3$OD) 3.84 (dd, J=11.1, 5.4 Hz, 1H), 3.78 (dd, J=7.1, 4.2 Hz, 1H), 3.43 (ddd, J=10.3, 9.0, 5.4 Hz, 1H), 3.27-3.15 (m, 2H), 3.11 (t, J=10.8 Hz, 1H), 3.03 (t, J=9.1 Hz, 1H), 1.96 (ddd, J=14.4, 5.8, 2.8 Hz, 1H), 1.54 (ddd, J=15.1, 9.0, 6.7 Hz, 1H), 1.50-1.23 (m, 12H), 0.89 (t, J=6.9 Hz, 3H). $^{13}$C NMR (151 MHz, CD$_3$OD) δ 79.08, 78.28, 74.41, 70.01, 69.52, 69.34, 39.25, 36.35, 31.60, 29.34, 29.00, 25.09, 22.30, 13.01. HR-MS (ESI$^+$, m/z): Calcd for C$_{14}$H$_{28}$O$_5$Na [M+Na]$^+$ 299.18344 Found 299.16790.

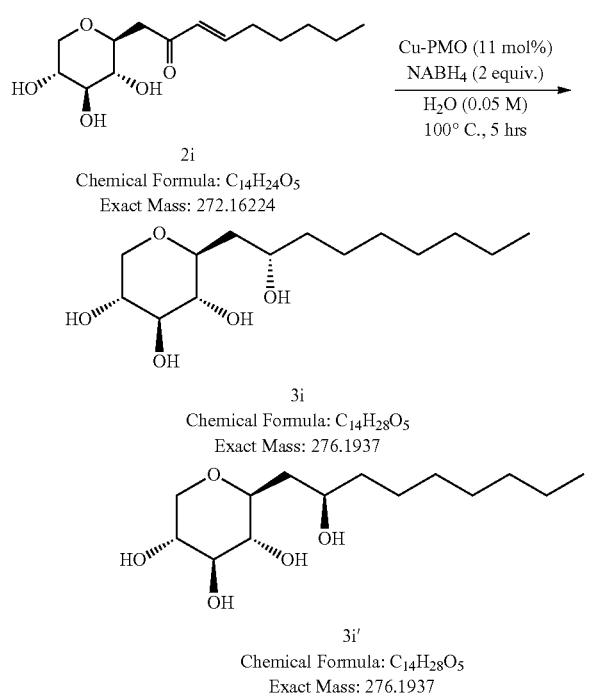

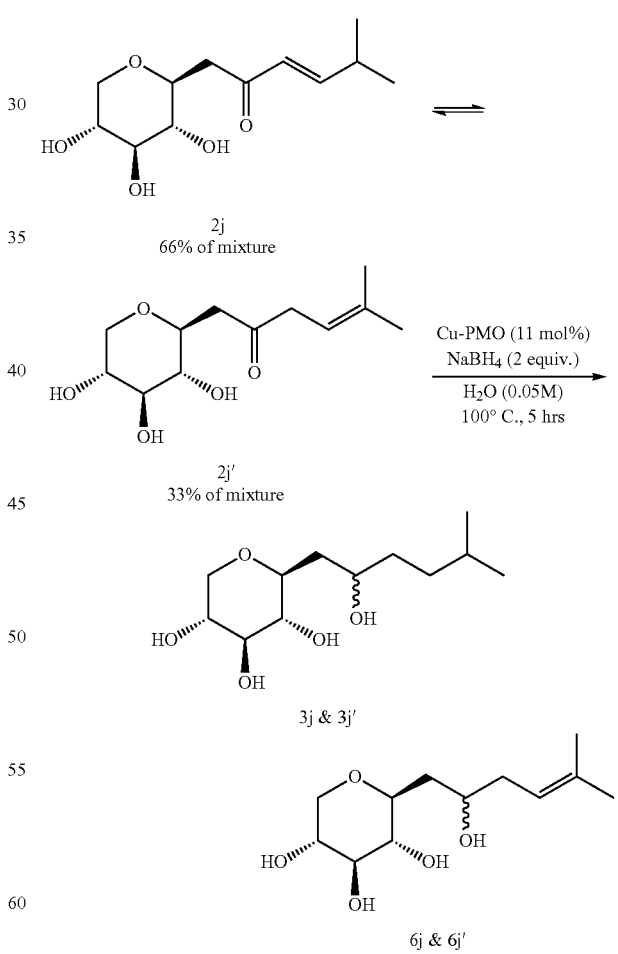

3i and 3i' were synthesized following general procedure C with 2i (136.1 mg, 0.5 mmol), Cu-PMO (16.5 mg, 11 mol %) and NaBH$_4$ (37.8 mg, 1.0 mmol, 2 equiv.) in H$_2$O (10 mL, 0.05 M) at reflux for 5 hours. Because the starting material is very hygroscopic, the true added amount of starting 3j and 3j' were synthesized following general procedure C with 2j (122.2 mg, 0.5 mmol, 1 equiv.), Cu-PMO (16.5 mg, 11 mol %) and NaBH$_4$ (37.8 mg, 1.0 mmol, 2 equiv.) in H$_2$O (10 mL, 0.05 M) at reflux for 5 hours. Because the starting material is very hygroscopic, the true added amount of starting material 2j present in a stock solution was verified by NMR using CHCl₃ (0.04 mL, 0.5 mmol) as internal standard. After reaction, the crude mixture fully dissolved in MeOD and an internal standard (CHCl₃, 40 µL, 1 equiv.) was added to obtain the NMR yield. Boron NMR was measured to verify the absence of boron salts in the crude mixture. The diastereomers were separated by column chromatography (silica gel, DCM:MeOH, 450:50) to afford 3j' as a clear oil in 10.2% yield. Unfortunately, diastereomer 3j could not be isolated separately from 3j'. Further optimization of separation of the diastereomers is required. Mixture HR-MS (ESI⁺, m/z): Calcd for $C_{12}H_{25}O_5$ [M+H]⁺ 249.17020 Found 249.16894.

3j' $R_f$=0.25 (silica gel, 8:1 DCM:MeOH); ¹H NMR (400 MHz, CD₃OD) δ 3.82 (dd, J=11.0, 5.4 Hz, 2H), 3.75-3.65 (m, 1H), 3.43 (ddd, J=10.5, 8.9, 5.4 Hz, 2H), 3.35-3.20 (m, 13H), 3.18-3.07 (m, 1H), 3.00 (q, J=9.2, 8.8 Hz, 1H), 1.91-1.78 (m, 1H), 1.57-1.46 (m, 1H), 1.46-1.37 (m, 2H), 1.36-1.22 (m, 2H), 1.23-1.10 (m, 2H), 1.01-0.93 (m, 2H), 0.88 (dd, J=6.6, 2.5 Hz, 7H). ¹³C NMR (151 MHz, CD₃OD) δ 78.46, 77.19, 74.38, 70.21, 69.48, 67.46, 39.63, 35.55, 34.66, 27.84, 21.68, 21.53. HR-MS (ESI⁺, m/z): Calcd for $C_{12}H_{24}O_5$ [M+Na]⁺271.15214 Found 271.12140.

4. C-Glycosidic Ketones 5a and 5d

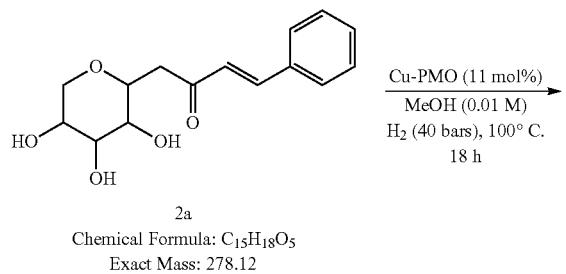

2a
Chemical Formula: $C_{15}H_{18}O_5$
Exact Mass: 278.12

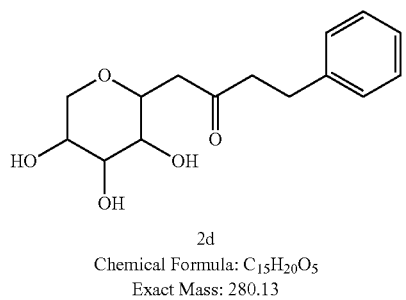

2d
Chemical Formula: $C_{15}H_{20}O_5$
Exact Mass: 280.13

$R_f$=0.39 (silica gel, 9:1 DCM:MeOH, develop with CAM); Substrate 2a (83.49 mg, 0.30 mmol, 1 equiv.) was added to a 100 mL Parr reactor. Cu-PMO catalyst (10 mg, 0.03 mmol, 0.11 equiv.) was added to the reactor. MeOH (30 mL, 0.01 M) was added to the reactor by syringe. The vessel was closed and pressurized with H₂ (40 bars at room temperature). The vessel was placed on a stand and heated to 100° C. with stirring for a total of 18 hours. Upon completion, the vessel was cooled using tap water and depressurized inside a fumehood. The vessel was opened and the contents were filtered over a glass filter. The filtrate was washed with methanol. The organic fraction was recovered and concentrated in vacuo to provide crude 5a.

¹H NMR (400 MHz, CD₃OD) δ 7.17 (ddt, J=24.6, 16.3, 7.3 Hz, 5H), 3.79 (ddd, J=21.8, 11.3, 5.6 Hz, 1H), 3.54 (td, J=9.4, 2.8 Hz, 1H), 3.41 (td, J=9.7, 5.3 Hz, 1H), 3.33-3.18 (m, 2H), 3.16-2.99 (m, 2H), 2.97 (m, 4H), 2.53 (dd, J=15.8, 9.3 Hz, 1H). ¹³C NMR (101 MHz, CD₃OD) δ 209.28, 141.09, 127.97, 127.91, 125.56, 78.28, 76.81, 73.67, 70.03, 69.55, 45.07, 44.52, 29.02.

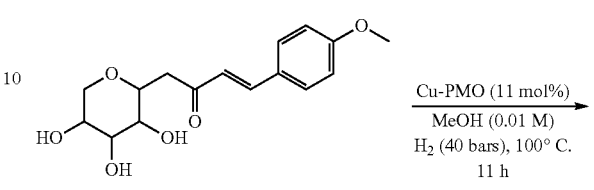

2d
Chemical Formula: $C_{16}H_{20}O_6$
Exact Mass: 308.33

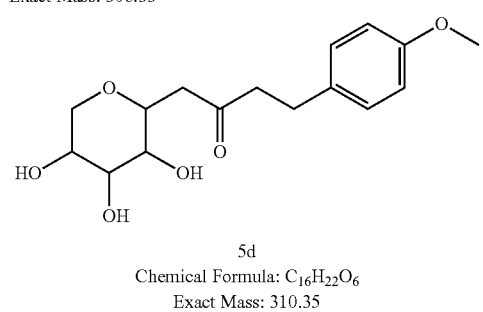

5d
Chemical Formula: $C_{16}H_{22}O_6$
Exact Mass: 310.35

Substrate 2d (100 mg, 0.324 mmol, 1 equiv.) was added to a 100 mL Parr reactor. Cu-PMO catalyst (10 mg, 0.03 mmol, 0.11 equiv.) was added to the reactor. MeOH (30 mL, 0.01 M) was added to the reactor by syringe. The vessel was closed and pressurized with H₂ (40 bars at room temperature). The vessel was placed on a stand and heated to 100° C. with stirring for a total of 11 hours. Upon completion, the vessel was cooled using tap water and depressurized inside a fumehood. The vessel was opened and the contents were filtered over a glass filter. he filtrate was washed with methanol. The organic fraction was recovered and concentrated in vacuo to provide crude 5d. Column chromatography (silica gel, 45:5 DCM:MeOH) was performed to yield pure 5d in 20% isolated yield as a white powder (20 mg).

$R_f$=0.37 (silica gel, 8:1 DCM:MeOH, develop with CAM); ¹H NMR (400 MHz, CD₃OD) δ 7.09-7.03 (m, 2H), 6.82-6.75 (m, 2H), 3.78 (s, 3H), 3.76 (dd, J=11.1, 5.4 Hz, 1H), 3.54 (td, J=9.4, 2.8 Hz, 1H), 3.40 (ddd, J=10.5, 9.0, 5.4 Hz, 1H), 3.29 (p, J=1.7 Hz, 1H), 3.23 (t, J=8.9 Hz, 1H), 3.10 (d, J=10.9 Hz, 1H), 3.07-2.97 (m, 1H), 2.85-2.72 (m, 4H), 2.51 (dd, J=15.8, 9.3 Hz, 1H); ¹³C NMR (101 MHz, CD₃OD) δ 209.48, 158.00, 133.00, 128.82, 113.36, 78.26, 76.80, 73.65, 70.03, 69.55, 54.18, 45.09, 44.80, 28.19.

L. Procedures and Tables for Calculated Geometries

The proton and carbon NMR shifts were calculated computationally in methanol and compared with experimental data of the separated isomers in methanol using Smith and Goodman's CP3 parameter and related probability factor (Bokor, et al., 2017, Chem. Rev. 117:1687-1764). The full procedure for the calculations of the NMR chemical shifts can be found elsewhere herein. Several conformers of each diastereomer were generated using the Tinker 8.2 program (Bisht, et al, 2011, Carbohydr. Res. 346:1191-1201), and the most stable geometries of all conformers were calculated using Gaussian 16. Ground state geometries were optimized in methanol by using the self-consistent reaction field (SCRF) method combined with the polarized continuum (PCM) solvation model (Cavezza & M. Dalko, WO2010063948A2, 2010) with ωB97XD (Cavezza, et al., 2009, Bioorg. Med. Chem. Lett. 19:845-849) and the def2TZVP (Foley, et al, 2011, Green Chem. 13:321-325; Kirschning, et al., 2000, Biorg. Med. Chem. 8:2347-2354) basis set. NMR shielding constants for proton and carbon nuclei were calculated using GIRO method as implemented in Gaussian 16.

Figure 7:
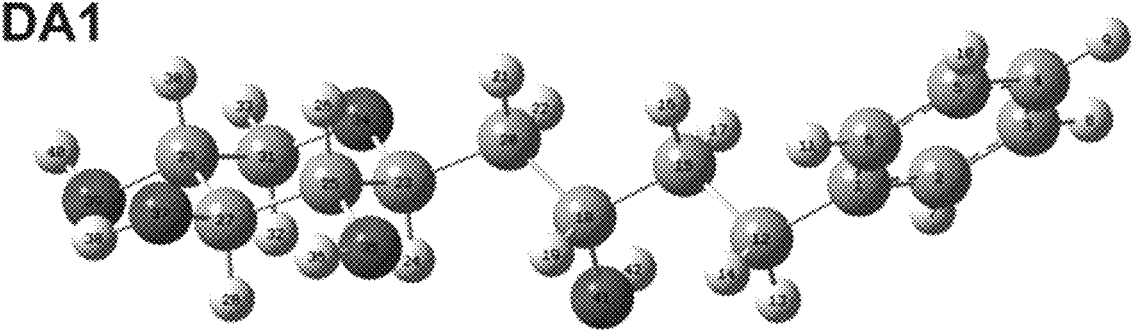
FIG. 7 illustrates initial structures of the two diastereomers used for the conformational search with the numbering of the atoms; white—hydrogen, red—oxygen, gray—carbon.
Figure 7:
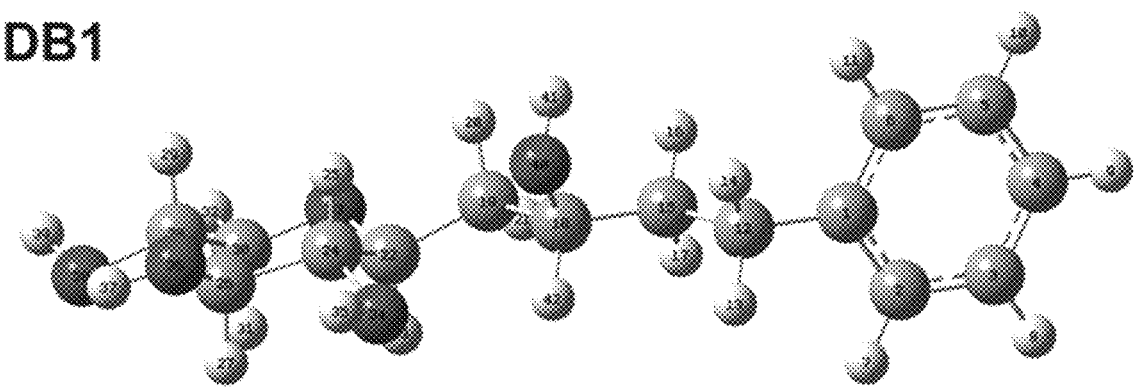

To obtain the conformers for the two diastereomers of the compound, 3a and 3a', for the NMR shift calculations, conformational search was performed using Tinker 8.2 program. Initial structures for the conformational search, DA1 and DB1, were obtained from the gas phase optimization of the two diastereomers (FIG. 7). MMFF force field in gas phase with rms gradient cutoff of 1 kcal/mol was used to obtain ten structures for each diastereomer with sufficiently different conformations. For each of the conformers ground state geometries were optimized using ωB97XD/def2TZVP method in methanol, and then energies and GIAO shielding constants were calculated.

1. Coordinates for the Optimized Geometries

The following geometries were optimized by Gaussian 16 using ωB971M)/def2TZVP method in methanol:

| # | Atom | X | Y | Z |
|---|------|---|---|---|
| DA1 | | | | |
| 1 | C | 4.28515 | 0.178973 | 0.357223 |
| 2 | C | 5.075972 | −0.96701 | 0.375162 |
| 3 | C | 6.325913 | −0.98155 | −0.22697 |
| 4 | C | 6.807443 | 0.155907 | −0.85984 |
| 5 | C | 6.029495 | 1.304995 | −0.88435 |
| 6 | C | 4.78007 | 1.313288 | −0.28102 |
| 7 | H | 4.707272 | −1.85889 | 0.869883 |
| 8 | H | 6.926703 | −1.88232 | −0.19903 |
| 9 | H | 7.783727 | 0.147884 | −1.32792 |
| 10 | H | 6.397657 | 2.199041 | −1.37248 |
| 11 | H | 4.178574 | 2.21542 | −0.30294 |
| 12 | C | 2.910011 | 0.17536 | 0.968693 |
| 13 | H | 2.885884 | −0.50415 | 1.82223 |
| 14 | H | 2.67107 | 1.173379 | 1.345701 |
| 15 | C | 1.837998 | −0.24542 | −0.03736 |
| 16 | H | 1.851129 | 0.441547 | −0.88811 |
| 17 | H | 2.076814 | −1.2394 | −0.43409 |
| 18 | C | 0.432428 | −0.26907 | 0.550497 |
| 19 | H | 0.200556 | 0.712943 | 0.96417 |
| 20 | C | −0.59898 | −0.6253 | −0.51761 |
| 21 | H | −0.46238 | 0.023065 | −1.38708 |
| 22 | H | −0.4052 | −1.64953 | −0.85173 |
| 23 | C | −2.04641 | −0.56527 | −0.0541 |
| 24 | H | −2.10677 | −0.89674 | 0.991608 |
| 25 | C | −2.67094 | 0.826803 | −0.16433 |
| 26 | H | −2.59508 | 1.150928 | −1.21185 |
| 27 | C | −4.14111 | 0.780132 | 0.215644 |
| 28 | H | −4.21453 | 0.504466 | 1.277258 |
| 29 | C | −4.86978 | −0.26956 | −0.59887 |
| 30 | H | −4.87545 | 0.043211 | −1.64897 |
| 31 | C | −4.13 | −1.59735 | −0.47035 |
| 32 | H | −4.19369 | −1.94645 | 0.569585 |
| 33 | H | −4.58147 | −2.35152 | −1.11526 |
| 34 | O | −2.78523 | −1.46313 | −0.87085 |
| 35 | O | −1.97225 | 1.723495 | 0.673467 |
| 36 | O | −2.48268 | 2.537791 | 0.70415 |
| 37 | O | −4.66667 | 2.078435 | 0.018185 |
| 38 | H | −5.58933 | 2.068215 | 0.284651 |
| 39 | O | −6.19071 | −0.35308 | −0.09734 |
| 40 | H | −6.75142 | −0.7695 | −0.75452 |
| 41 | O | 0.345962 | −1.15666 | 1.660781 |
| 42 | H | 0.566246 | −2.04145 | 1.356249 |
| DA2 | | | | |
| 1 | C | 4.368153 | −0.312942 | 0.298696 |
| 2 | C | 5.019186 | −0.790124 | −0.83608 |
| 3 | C | 6.268212 | −0.307235 | −1.198915 |
| 4 | C | 6.889416 | 0.666055 | −0.428707 |
| 5 | C | 6.251614 | 1.150075 | 0.704874 |
| 6 | C | 5.002172 | 0.663665 | 1.062297 |
| 7 | H | 4.540729 | −1.552386 | −1.441159 |
| 8 | H | 6.759035 | −0.694158 | −2.08352 |
| 9 | H | 7.865441 | 1.042334 | −0.708229 |
| 10 | H | 6.729463 | 1.906978 | 1.314719 |
| 11 | H | 4.510837 | 1.04535 | 1.950598 |
| 12 | C | 2.993453 | −0.806392 | 0.661417 |
| 13 | H | 2.882455 | −1.848479 | 0.358387 |
| 14 | H | 2.863475 | −0.770195 | 1.74656 |
| 15 | C | 1.894011 | 0.027255 | 0.00072 |
| 16 | H | 2.00016 | 1.071234 | 0.307813 |
| 17 | H | 2.014222 | −0.002908 | −1.08703 |
| 18 | C | 0.492851 | −0.442305 | 0.352308 |
| 19 | H | 0.376083 | −0.394306 | 1.446079 |
| 20 | C | −0.571848 | 0.448698 | −0.280574 |
| 21 | H | −0.346982 | 1.491156 | −0.050095 |
| 22 | H | −0.537539 | 0.33598 | −1.368978 |
| 23 | C | −1.978684 | 0.165821 | 0.209948 |
| 24 | H | −2.006552 | 0.252425 | 1.306298 |
| 25 | C | −3.012114 | 1.128349 | −0.372218 |
| 26 | H | −2.969515 | 1.060722 | −1.468104 |
| 27 | C | −4.40917 | 0.738439 | 0.080366 |
| 28 | H | −4.466407 | 0.871187 | 1.170159 |
| 29 | C | −4.690795 | −0.71856 | −0.233402 |
| 30 | H | −4.716624 | −0.844926 | −1.321303 |
| 31 | C | −3.575672 | −1.580572 | 0.349 |
| 32 | H | −3.593746 | −1.511958 | 1.444289 |
| 33 | H | −3.704857 | −2.623936 | 0.063588 |
| 34 | O | −2.322031 | −1.167065 | −0.155237 |
| 35 | O | −2.694547 | 2.436124 | 0.052198 |
| 36 | H | −3.434236 | 3.001993 | −0.186213 |
| 37 | O | −5.317583 | 1.611661 | −0.55987 |
| 38 | H | −6.20261 | 1.390875 | −0.258686 |
| 39 | O | −5.945802 | −1.036675 | 0.336077 |
| 40 | H | −6.295502 | −1.822057 | −0.088908 |
| 41 | O | 0.363592 | −1.793427 | −0.071302 |
| 42 | H | −0.581096 | −1.99122 | −0.07958 |
| DA3 | | | | |
| 1 | C | −4.07347 | 0.302679 | −0.22945 |
| 2 | C | −4.43612 | −0.39215 | −1.37993 |
| 3 | C | −5.74147 | −0.82184 | −1.57179 |
| 4 | C | −6.70841 | −0.56205 | −0.61093 |
| 5 | C | −6.35934 | 0.130067 | 0.540475 |
| 6 | C | −5.05264 | 0.557001 | 0.727214 |
| 7 | H | −3.686 | −0.59694 | −2.13586 |
| 8 | H | −6.00446 | −1.35825 | −2.47517 |
| 9 | H | −7.72816 | −0.89413 | −0.75958 |
| 10 | H | −7.10755 | 0.340653 | 1.294716 |
| 11 | H | −4.78723 | 1.098282 | 1.628689 |
| 12 | C | −2.64613 | 0.724505 | −0.00344 |
| 13 | H | −2.17189 | 0.919527 | −0.96739 |
| 14 | H | −2.63559 | 1.662984 | 0.557504 |
| 15 | C | −1.8574 | −0.34397 | 0.759616 |
| 16 | H | −2.37079 | −0.56274 | 1.699565 |
| 17 | H | −1.85413 | −1.27012 | 0.177417 |
| 18 | C | −0.41153 | 0.024575 | 1.086858 |
| 19 | H | 0.035293 | −0.82204 | 1.607258 |
| 20 | C | 0.417484 | 0.327461 | −0.15942 |
| 21 | H | 0.225215 | −0.43291 | −0.92125 |
| 22 | H | 0.092143 | 1.283949 | −0.57822 |
| 23 | C | 1.912908 | 0.437668 | 0.098639 |
| 24 | H | 2.077137 | 0.862979 | 1.098662 |
| 25 | C | 2.650019 | −0.89943 | 0.00642 |
| 26 | H | 2.472084 | −1.31559 | −0.9952 |
| 27 | C | 4.145098 | −0.69355 | 0.178892 |
| 28 | H | 4.327567 | −0.32139 | 1.197037 |

| # | Atom | X | Y | Z |
|---|---|---|---|---|
| 29 | C | 4.656307 | 0.340798 | −0.80367 |
| 30 | H | 4.556682 | −0.0607 | −1.81825 |
| 31 | C | 3.813771 | 1.605863 | −0.67469 |
| 32 | H | 3.977094 | 2.047951 | 0.317861 |
| 33 | H | 4.102581 | 2.337377 | −1.42948 |
| 34 | O | 2.447543 | 1.321903 | −0.87599 |
| 35 | O | 2.152779 | −1.77873 | 0.992969 |
| 36 | H | 2.736048 | −2.54294 | 1.011176 |
| 37 | O | 4.764753 | −1.9534 | 0.008254 |
| 38 | H | 5.708871 | −1.83993 | 0.143253 |
| 39 | O | 6.01644 | 0.581737 | −0.49513 |
| 40 | H | 6.444373 | 0.985694 | −1.25235 |
| 41 | O | −0.33816 | 1.096625 | 2.022955 |
| 42 | H | −0.61061 | 1.907508 | 1.586305 |
| DA4 | | | | |
| 1 | C | 3.726994 | 0.189311 | 0.084951 |
| 2 | C | 3.840012 | −0.809781 | 1.04865 |
| 3 | C | 4.682777 | −1.894881 | 0.856603 |
| 4 | C | 5.429378 | −1.999387 | −0.308911 |
| 5 | C | 5.325953 | −1.010821 | −1.277346 |
| 6 | C | 4.481057 | 0.072102 | −1.07959 |
| 7 | H | 3.260729 | −0.733589 | 1.962323 |
| 8 | H | 4.759181 | −2.659336 | 1.620086 |
| 9 | H | 6.089859 | −2.843983 | −0.459765 |
| 10 | H | 5.906848 | −1.081304 | −2.188786 |
| 11 | H | 4.40676 | 0.841764 | −1.839984 |
| 12 | C | 2.775802 | 1.339155 | 0.277828 |
| 13 | H | 2.710095 | 1.592104 | 1.337603 |
| 14 | H | 3.155473 | 2.222994 | −0.241947 |
| 15 | C | 1.373682 | 1.017186 | −0.2401 |
| 16 | H | 1.422894 | 0.799329 | −1.311612 |
| 17 | H | 1.007892 | 0.111579 | 0.252084 |
| 18 | C | 0.380974 | 2.153923 | −0.006329 |
| 19 | H | 0.823443 | 3.073768 | −0.400071 |
| 20 | C | −0.938788 | 1.966033 | −0.761552 |
| 21 | H | −1.624506 | 2.762396 | −0.459782 |
| 22 | H | −0.731731 | 2.111046 | −1.824627 |
| 23 | C | −1.6697 | 0.630667 | −0.663827 |
| 24 | H | −0.987812 | −0.194205 | −0.913602 |
| 25 | C | −2.312074 | 0.325617 | 0.692432 |
| 26 | H | −2.9515 | 1.172421 | 0.972905 |
| 27 | C | −3.16423 | −0.929344 | 0.618107 |
| 28 | H | −2.499682 | −1.781856 | 0.41835 |
| 29 | C | −4.166771 | −0.84142 | −0.513228 |
| 30 | H | −4.886216 | −0.046205 | −0.28891 |
| 31 | C | −3.41839 | −0.501183 | −1.796827 |
| 32 | H | −2.748689 | −1.332115 | −2.057313 |
| 33 | H | −4.116154 | −0.349083 | −2.620202 |
| 34 | O | −2.694673 | 0.698556 | −1.644944 |
| 35 | O | −1.298919 | 0.139736 | 1.668187 |
| 36 | H | −1.721688 | −0.203482 | 2.461692 |
| 37 | O | −3.778208 | −1.083281 | 1.88238 |
| 38 | H | −4.275426 | −1.905452 | 1.873698 |
| 39 | O | −4.816604 | −2.095019 | −0.596894 |
| 40 | H | −5.633537 | −1.994379 | −1.089057 |
| 41 | O | 0.191676 | 2.409887 | 1.375419 |
| 42 | H | −0.272455 | 1.639624 | 1.738557 |
| DA5 | | | | |
| 1 | C | −3.737352 | −0.050669 | 0.305211 |
| 2 | C | −4.613741 | 0.370725 | −0.691266 |
| 3 | C | −5.481804 | −0.522408 | −1.302917 |
| 4 | C | −5.487144 | −1.857909 | −0.925514 |
| 5 | C | −4.618878 | −2.290846 | 0.067022 |
| 6 | C | −3.752612 | −1.393323 | 0.674357 |
| 7 | H | −4.616921 | 1.413378 | −0.989497 |
| 8 | H | −6.157972 | −0.173819 | −2.073882 |
| 9 | H | −6.16573 | −2.556056 | −1.399202 |
| 10 | H | −4.617915 | −3.330297 | 0.371422 |
| 11 | H | −3.077993 | −1.738452 | 1.450242 |
| 12 | C | −2.763582 | 0.910316 | 0.932133 |
| 13 | H | −3.192805 | 1.913028 | 0.953511 |
| 14 | H | −2.575154 | 0.619792 | 1.969261 |
| 15 | C | −1.432981 | 0.945993 | 0.178654 |
| 16 | H | −1.019142 | −0.06513 | 0.151206 |
| 17 | H | −1.605042 | 1.243501 | −0.862627 |
| 18 | C | −0.410626 | 1.884494 | 0.807081 |
| 19 | H | −0.234408 | 1.569514 | 1.837484 |
| 20 | C | 0.922126 | 1.909558 | 0.061192 |
| 21 | H | 0.758343 | 2.281249 | −0.953937 |
| 22 | H | 1.581239 | 2.620971 | 0.566203 |
| 23 | C | 1.628196 | 0.571646 | −0.035798 |
| 24 | H | 1.015911 | −0.137801 | −0.610929 |
| 25 | C | 2.982818 | 0.683212 | −0.736171 |
| 26 | H | 3.599427 | 1.40682 | −0.185162 |
| 27 | C | 3.691137 | −0.6604 | −0.723064 |
| 28 | H | 3.104172 | −1.364383 | −1.330171 |
| 29 | C | 3.773023 | −1.208715 | 0.688109 |
| 30 | H | 4.42468 | −0.55718 | 1.280858 |
| 31 | C | 2.376122 | −1.219175 | 1.301413 |
| 32 | H | 1.744362 | −1.929835 | 0.751023 |
| 33 | H | 2.417667 | −1.530794 | 2.345024 |
| 34 | O | 1.811323 | 0.072542 | 1.277562 |
| 35 | O | 2.771452 | 1.126026 | −2.059902 |
| 36 | H | 3.605085 | 1.032127 | −2.529387 |
| 37 | O | 4.966578 | −0.471592 | −1.303502 |
| 38 | H | 5.413946 | −1.321539 | −1.316543 |
| 39 | O | 4.317454 | −2.512142 | 0.601536 |
| 40 | H | 4.657006 | −2.769588 | 1.460651 |
| 41 | O | −0.917473 | 3.210426 | 0.919003 |
| 42 | H | −1.101648 | 3.537406 | 0.034214 |
| DA6 | | | | |
| 1 | C | 4.077917 | 0.254556 | 0.337274 |
| 2 | C | 5.015965 | −0.567662 | 0.955943 |
| 3 | C | 6.363849 | −0.474209 | 0.641256 |
| 4 | C | 6.79653 | 0.446957 | −0.302596 |
| 5 | C | 5.871469 | 1.272183 | −0.926261 |
| 6 | C | 4.524544 | 1.174476 | −0.60721 |
| 7 | H | 4.685103 | −1.288457 | 1.695574 |
| 8 | H | 7.078464 | −1.120244 | 1.136231 |
| 9 | H | 7.8483 | 0.523229 | −0.548031 |
| 10 | H | 6.199456 | 1.996501 | −1.661658 |
| 11 | H | 3.80744 | 1.824063 | −1.096888 |
| 12 | C | 2.610956 | 0.119133 | 0.647976 |
| 13 | H | 2.482241 | −0.161984 | 1.696633 |
| 14 | H | 2.126681 | 1.088854 | 0.516086 |
| 15 | C | 1.938482 | −0.93101 | −0.238188 |
| 16 | H | 2.034366 | −0.64631 | −1.290747 |
| 17 | H | 2.46181 | −1.883243 | −0.118075 |
| 18 | C | 0.470712 | −1.170149 | 0.0819 |
| 19 | H | 0.375399 | −1.333024 | 1.166328 |
| 20 | C | −0.418863 | 0.007641 | −0.304816 |
| 21 | H | −0.011989 | 0.926814 | 0.117562 |
| 22 | H | −0.416032 | 0.116141 | −1.394308 |
| 23 | C | −1.848239 | −0.114627 | 0.186435 |
| 24 | H | −1.847704 | −0.252182 | 1.277887 |
| 25 | C | −2.690676 | 1.117167 | −0.140093 |
| 26 | H | −2.672246 | 1.270504 | −1.227973 |
| 27 | C | −4.131265 | 0.900145 | 0.291184 |
| 28 | H | −4.15208 | 0.812648 | 1.386891 |
| 29 | C | −4.681786 | −0.385527 | −0.295914 |
| 30 | H | −4.740245 | −0.277906 | −1.384532 |
| 31 | C | −3.741047 | −1.535546 | 0.048095 |
| 32 | H | −3.735653 | −1.692003 | 1.13443 |
| 33 | H | −4.064296 | −2.457259 | −0.434291 |
| 34 | O | −2.437244 | −1.25943 | −0.42187 |
| 35 | O | −2.131228 | 2.230472 | 0.522507 |
| 36 | H | −2.754135 | 2.957615 | 0.436378 |
| 37 | O | −4.867611 | 2.035688 | −0.115921 |
| 38 | H | −5.776291 | 1.918212 | 0.17262 |
| 39 | O | −5.969073 | −0.582715 | 0.256083 |
| 40 | H | −6.465597 | −1.181132 | −0.305236 |
| 41 | O | 0.088024 | −2.355404 | −0.604474 |
| 42 | H | −0.877226 | −2.370875 | −0.615389 |
| DA7 | | | | |
| 1 | C | −4.038816 | −0.059869 | −0.369022 |
| 2 | C | −4.538426 | −1.340479 | −0.147702 |
| 3 | C | −5.90142 | −1.561278 | −0.009362 |
| 4 | C | −6.790733 | −0.498992 | −0.090065 |
| 5 | C | −6.305699 | 0.782736 | −0.310616 |
| 6 | C | −4.941926 | 0.997327 | −0.447767 |

| # | Atom | X | Y | Z |
|---|---|---|---|---|
| 7 | H | −3.849589 | −2.175853 | −0.08579 |
| 8 | H | −6.269916 | −2.565777 | 0.158923 |
| 9 | H | −7.854863 | −0.669072 | 0.01488 |
| 10 | H | −6.991784 | 1.618061 | −0.378872 |
| 11 | H | −4.570108 | 2.001205 | −0.621165 |
| 12 | C | −2.557124 | 0.182743 | −0.471826 |
| 13 | H | −2.077732 | −0.699107 | −0.901998 |
| 14 | H | −2.363243 | 1.018334 | −1.146694 |
| 15 | C | −1.939639 | 0.492454 | 0.894873 |
| 16 | H | −2.483484 | 1.323489 | 1.352555 |
| 17 | H | −2.065571 | −0.369426 | 1.556006 |
| 18 | C | −0.463782 | 0.863705 | 0.858084 |
| 19 | H | −0.135519 | 0.995584 | 1.899345 |
| 20 | C | 0.412323 | −0.215979 | 0.226804 |
| 21 | H | 0.148994 | −1.185362 | 0.653586 |
| 22 | H | 0.222501 | −0.265686 | −0.849147 |
| 23 | C | 1.895485 | 0.001882 | 0.45439 |
| 24 | H | 2.092558 | 0.077097 | 1.534071 |
| 25 | C | 2.752137 | −1.129447 | −0.110924 |
| 26 | H | 2.536453 | −1.224122 | −1.184168 |
| 27 | C | 4.227659 | −0.808072 | 0.056282 |
| 28 | H | 4.453567 | −0.77939 | 1.131819 |
| 29 | C | 4.552055 | 0.552259 | −0.530917 |
| 30 | H | 4.406049 | 0.510484 | −1.615852 |
| 31 | C | 3.610055 | 1.592469 | 0.065951 |
| 32 | H | 3.80378 | 1.686999 | 1.14221 |
| 33 | H | 3.762194 | 2.564795 | −0.401191 |
| 34 | O | 2.265189 | 1.22773 | −0.168319 |
| 35 | O | 2.418342 | −2.322589 | 0.564664 |
| 36 | H | 3.066208 | −2.986113 | 0.311446 |
| 37 | O | 4.957935 | −1.848267 | −0.561995 |
| 38 | H | 5.893205 | −1.665267 | −0.441185 |
| 39 | O | 5.902839 | 0.833477 | −0.21923 |
| 40 | H | 6.232392 | 1.505019 | −0.819301 |
| 41 | O | −0.342219 | 2.104504 | 0.173786 |
| 42 | H | 0.594331 | 2.216504 | −0.02983 |
| DA8 | | | | |
| 1 | C | 4.014283 | −0.502404 | −0.331745 |
| 2 | C | 4.313913 | 0.567672 | −1.167505 |
| 3 | C | 5.115965 | 1.613841 | −0.731923 |
| 4 | C | 5.635818 | 1.604591 | 0.55385 |
| 5 | C | 5.350759 | 0.537873 | 1.396357 |
| 6 | C | 4.550893 | −0.504289 | 0.954009 |
| 7 | H | 3.907087 | 0.586667 | −2.172231 |
| 8 | H | 5.333482 | 2.438826 | −1.399351 |
| 9 | H | 6.260954 | 2.419472 | 0.896785 |
| 10 | H | 5.756212 | 0.516673 | 2.400598 |
| 11 | H | 4.338852 | −1.33397 | 1.619459 |
| 12 | C | 3.156295 | −1.648668 | −0.805056 |
| 13 | H | 2.940494 | −1.523908 | −1.869382 |
| 14 | H | 3.739346 | −2.569587 | −0.715783 |
| 15 | C | 1.837814 | −1.858449 | −0.051535 |
| 16 | H | 1.459271 | −2.849713 | −0.311981 |
| 17 | H | 2.013944 | −1.860938 | 1.028369 |
| 18 | C | 0.741163 | −0.853091 | −0.366471 |
| 19 | H | 0.618882 | −0.811982 | −1.46026 |
| 20 | C | −0.593202 | −1.279142 | 0.242878 |
| 21 | H | −0.796106 | −2.316433 | −0.027266 |
| 22 | H | −0.524755 | −1.228873 | 1.334406 |
| 23 | C | −1.77435 | −0.450957 | −0.225672 |
| 24 | H | −1.82549 | −0.479827 | −1.324336 |
| 25 | C | −3.105366 | −0.956085 | 0.328686 |
| 26 | H | −3.047825 | −0.949435 | 1.425969 |
| 27 | C | −4.23745 | −0.037721 | −0.099456 |
| 28 | H | −4.334067 | −0.098633 | −1.192819 |
| 29 | C | −3.932646 | 1.401765 | 0.26812 |
| 30 | H | −3.91523 | 1.489385 | 1.359947 |
| 31 | C | −2.565815 | 1.782663 | −0.290799 |
| 32 | H | −2.600733 | 1.765213 | −1.387699 |
| 33 | H | −2.281274 | 2.783496 | 0.032464 |
| 34 | O | −1.575688 | 0.896468 | 0.190062 |
| 35 | O | −3.318759 | −2.268276 | −0.144496 |
| 36 | H | −4.221954 | −2.509891 | 0.079223 |
| 37 | O | −5.418597 | −0.510851 | 0.515872 |
| 38 | H | −6.144888 | 0.050396 | 0.23254 |
| 39 | O | −4.961368 | 2.202552 | −0.280724 |

| # | Atom | X | Y | Z |
|---|---|---|---|---|
| 40 | H | −4.984491 | 3.044737 | 0.177297 |
| 41 | O | 1.138829 | 0.425038 | 0.108008 |
| 42 | H | 0.34451 | 0.973273 | 0.121838 |
| DA9 | | | | |
| 1 | C | −4.038655 | −0.059964 | −0.368915 |
| 2 | C | −4.538256 | −1.340407 | −0.146557 |
| 3 | C | −5.901267 | −1.561176 | −0.008444 |
| 4 | C | −6.790632 | −0.499015 | −0.090391 |
| 5 | C | −6.305609 | 0.782541 | −0.311896 |
| 6 | C | −4.941796 | 0.9971 | −0.448831 |
| 7 | H | −3.849376 | −2.175673 | −0.083635 |
| 8 | H | −6.269751 | −2.565548 | 0.160626 |
| 9 | H | −7.854783 | −0.669091 | 0.014353 |
| 10 | H | −6.991708 | 1.617777 | −0.381081 |
| 11 | H | −4.570013 | 2.000862 | −0.622967 |
| 12 | C | −2.556935 | 0.182542 | −0.471542 |
| 13 | H | −2.07754 | −0.699589 | −0.901158 |
| 14 | H | −2.362919 | 1.017746 | −1.146859 |
| 15 | C | −1.939635 | 0.492907 | 0.895034 |
| 16 | H | −2.483442 | 1.324196 | 1.352307 |
| 17 | H | −2.065684 | −0.368656 | 1.556554 |
| 18 | C | −0.463726 | 0.864006 | 0.858281 |
| 19 | H | −0.135493 | 0.995921 | 1.899541 |
| 20 | C | 0.412248 | −0.215731 | 0.226928 |
| 21 | H | 0.148806 | −1.18516 | 0.653524 |
| 22 | H | 0.222395 | −0.265187 | −0.849042 |
| 23 | C | 1.895431 | 0.00191 | 0.454547 |
| 24 | H | 2.092512 | 0.076875 | 1.534243 |
| 25 | C | 2.751915 | −1.129416 | −0.111012 |
| 26 | H | 2.536063 | −1.223974 | −1.184228 |
| 27 | C | 4.227521 | −0.808268 | 0.055969 |
| 28 | H | 4.45368 | −0.779976 | 1.131452 |
| 29 | C | 4.551992 | 0.55219 | −0.530887 |
| 30 | H | 4.405836 | 0.510716 | −1.615817 |
| 31 | C | 3.610177 | 1.592339 | 0.066369 |
| 32 | H | 3.803994 | 1.686543 | 1.142643 |
| 33 | H | 3.762397 | 2.564791 | −0.40049 |
| 34 | O | 2.265244 | 1.227847 | −0.16789 |
| 35 | O | 2.4181 | −2.32259 | 0.564535 |
| 36 | H | 3.065281 | −2.986423 | 0.310384 |
| 37 | O | 4.957478 | −1.848408 | −0.562831 |
| 38 | H | 5.892807 | −1.66605 | −0.441552 |
| 39 | O | 5.902838 | 0.833191 | −0.219299 |
| 40 | H | 6.232122 | 1.505498 | −0.818662 |
| 41 | O | −0.341959 | 2.104792 | 0.173975 |
| 42 | H | 0.594555 | 2.216409 | −0.02997 |
| DA10 | | | | |
| 1 | C | −3.233047 | 0.071892 | 0.440079 |
| 2 | C | −4.554639 | 0.485668 | 0.305698 |
| 3 | C | −5.545422 | −0.407221 | −0.079926 |
| 4 | C | −5.226193 | −1.732343 | −0.339135 |
| 5 | C | −3.910967 | −2.157328 | −0.209087 |
| 6 | C | −2.925734 | −1.261149 | 0.176622 |
| 7 | H | −4.811512 | 1.519621 | 0.507912 |
| 8 | H | −6.569168 | −0.066815 | −0.175909 |
| 9 | H | −5.998261 | −2.430608 | −0.63797 |
| 10 | H | −3.652729 | −3.190539 | −0.406562 |
| 11 | H | −1.898682 | −1.593889 | 0.277594 |
| 12 | C | −2.143215 | 1.039791 | 0.814053 |
| 13 | H | −2.564513 | 1.869828 | 1.387171 |
| 14 | H | −1.420309 | 0.532246 | 1.454142 |
| 15 | C | −1.42799 | 1.584278 | −0.422336 |
| 16 | H | −1.036053 | 0.751461 | −1.011482 |
| 17 | H | −2.148614 | 2.112609 | −1.052162 |
| 18 | C | −0.296903 | 2.547587 | −0.100746 |
| 19 | H | −0.702966 | 3.365658 | 0.508831 |
| 20 | C | 0.874974 | 1.94161 | 0.673384 |
| 21 | H | 1.635196 | 2.717794 | 0.787063 |
| 22 | H | 0.559326 | 1.667556 | 1.68291 |
| 23 | C | 1.516533 | 0.73007 | 0.021373 |
| 24 | H | 1.483277 | 0.842178 | −1.072081 |
| 25 | C | 2.978672 | 0.550493 | 0.43046 |
| 26 | H | 3.027006 | 0.466818 | 1.525169 |
| 27 | C | 3.540757 | −0.722845 | −0.177822 |
| 28 | H | 3.555808 | −0.600325 | −1.270281 |

| # | Atom | X | Y | Z |
|---|---|---|---|---|
| 29 | C | 2.661521 | −1.913681 | 0.149893 |
| 30 | H | 2.70648 | −2.097201 | 1.229187 |
| 31 | C | 1.223499 | −1.594908 | −0.247015 |
| 32 | H | 1.16194 | −1.485472 | −1.338471 |
| 33 | H | 0.554941 | −2.401032 | 0.056315 |
| 34 | O | 0.781824 | −0.42405 | 0.400005 |
| 35 | O | 3.710433 | 1.676103 | −0.008283 |
| 36 | H | 4.642609 | 1.479418 | 0.119316 |
| 37 | O | 4.860222 | −0.878412 | 0.307067 |
| 38 | H | 5.228952 | −1.671158 | −0.090875 |
| 39 | O | 3.172885 | −3.022732 | −0.565568 |
| 40 | H | 2.847114 | −3.832052 | −0.167439 |
| 41 | O | 0.143886 | 3.071617 | −1.350631 |
| 42 | H | 0.857418 | 3.692221 | −1.186082 |

DB1

| # | Atom | X | Y | Z |
|---|---|---|---|---|
| 1 | C | 4.294699 | −0.36284 | −0.15292 |
| 2 | C | 4.895617 | 0.186247 | −1.28254 |
| 3 | C | 6.170219 | 0.731219 | −1.21973 |
| 4 | C | 6.866828 | 0.737117 | −0.01947 |
| 5 | C | 6.279069 | 0.193242 | 1.114264 |
| 6 | C | 5.004821 | −0.351 | 1.045036 |
| 7 | H | 4.358037 | 0.183531 | −2.2244 |
| 8 | H | 6.621399 | 1.149075 | −2.11097 |
| 9 | H | 7.86244 | 1.159566 | 0.031509 |
| 10 | H | 6.815985 | 0.189543 | 2.054927 |
| 11 | H | 4.553033 | −0.7769 | 1.934215 |
| 12 | C | 2.894947 | −0.91246 | −0.21165 |
| 13 | H | 2.696493 | −1.31106 | −1.21025 |
| 14 | H | 2.793227 | −1.74207 | 0.489655 |
| 15 | C | 1.847461 | 0.152383 | 0.114523 |
| 16 | H | 2.039343 | 0.564039 | 1.113004 |
| 17 | H | 1.946975 | 0.983016 | −0.58956 |
| 18 | C | 0.414146 | −0.36855 | 0.054313 |
| 19 | C | −0.58096 | 0.746167 | 0.379061 |
| 20 | H | −0.68523 | 0.803236 | 1.467382 |
| 21 | H | −0.16639 | 1.704603 | 0.059199 |
| 22 | C | −1.98187 | 0.664797 | −0.21746 |
| 23 | H | −1.93359 | 0.855648 | −1.30005 |
| 24 | C | −2.714 | −0.66813 | −0.0283 |
| 25 | H | −2.60845 | −0.98729 | 1.016356 |
| 26 | C | −4.19665 | −0.54304 | −0.35343 |
| 27 | H | −4.28749 | −0.39189 | −1.4387 |
| 28 | C | −4.83391 | 0.647534 | 0.32772 |
| 29 | H | −4.81741 | 0.496178 | 1.412821 |
| 30 | C | −4.01715 | 1.883459 | −0.02157 |
| 31 | H | −4.05831 | 2.056014 | −1.10595 |
| 32 | H | −4.41273 | 2.765261 | 0.482869 |
| 33 | O | −2.68941 | 1.720822 | 0.416305 |
| 34 | O | −2.13228 | −1.617 | −0.89935 |
| 35 | H | −2.60922 | −2.44249 | −0.78352 |
| 36 | O | −4.80569 | −1.7667 | 0.012099 |
| 37 | H | −5.7375 | −1.70814 | −0.21411 |
| 38 | O | −6.16566 | 0.737194 | −0.14432 |
| 39 | H | −6.6742 | 1.289941 | 0.451998 |
| 40 | O | 0.239224 | −1.48604 | 0.918934 |
| 41 | H | 0.451804 | −1.20314 | 1.812449 |
| 42 | H | 0.2227 | −0.76042 | −0.94553 |

DB2

| # | Atom | X | Y | Z |
|---|---|---|---|---|
| 1 | C | 3.487878 | −0.314061 | −0.331546 |
| 2 | C | 3.056219 | 0.482323 | −1.388424 |
| 3 | C | 3.316421 | 1.845668 | −1.408015 |
| 4 | C | 4.016799 | 2.43622 | −0.366193 |
| 5 | C | 4.454811 | 1.652924 | 0.693253 |
| 6 | C | 4.190981 | 0.291427 | 0.707614 |
| 7 | H | 2.50095 | 0.026522 | −2.200066 |
| 8 | H | 2.971456 | 2.44761 | −2.239758 |
| 9 | H | 4.222658 | 3.499127 | −0.380098 |
| 10 | H | 5.006306 | 2.103612 | 1.509277 |
| 11 | H | 4.537547 | −0.313903 | 1.538225 |
| 12 | C | 3.162985 | −1.784222 | −0.282235 |
| 13 | H | 2.96219 | −2.150484 | −1.289765 |
| 14 | H | 4.026804 | −2.335446 | 0.095688 |
| 15 | C | 1.9599 | −2.096425 | 0.615221 |
| 16 | H | 1.81756 | −3.179844 | 0.663047 |
| 17 | H | 2.168949 | −1.751007 | 1.631443 |

| # | Atom | X | Y | Z |
|---|---|---|---|---|
| 18 | C | 0.664191 | −1.456036 | 0.146907 |
| 19 | C | −0.481923 | −1.757482 | 1.108172 |
| 20 | H | −0.664952 | −2.835286 | 1.11682 |
| 21 | H | −0.179575 | −1.479637 | 2.120319 |
| 22 | C | −1.794812 | −1.050545 | 0.805633 |
| 23 | H | −2.533469 | −1.352301 | 1.561107 |
| 24 | C | −1.706751 | 0.48103 | 0.825726 |
| 25 | H | −0.978236 | 0.817155 | 0.080175 |
| 26 | C | −3.056568 | 1.080109 | 0.46758 |
| 27 | H | −3.778026 | 0.798766 | 1.248064 |
| 28 | C | −3.544352 | 0.52665 | −0.85784 |
| 29 | H | −2.857659 | 0.86323 | −1.645449 |
| 30 | C | −3.53156 | −0.992937 | −0.808976 |
| 31 | H | −4.269535 | −1.341847 | −0.075381 |
| 32 | H | −3.786668 | −1.40683 | −1.782997 |
| 33 | O | −2.247495 | −1.47606 | −0.475853 |
| 34 | O | −1.364669 | 0.969504 | 2.109564 |
| 35 | H | −0.410458 | 1.00638 | 2.195523 |
| 36 | O | −2.993585 | 2.486222 | 0.352028 |
| 37 | H | −2.660831 | 2.832802 | 1.184347 |
| 38 | O | −4.862788 | 0.93775 | −1.144824 |
| 39 | H | −4.892974 | 1.894973 | −1.066067 |
| 40 | O | 0.388102 | −1.928475 | −1.165158 |
| 41 | H | −0.544715 | −1.753799 | −1.339787 |
| 42 | H | 0.82105 | −0.369169 | 0.108021 |

DB3

| # | Atom | X | Y | Z |
|---|---|---|---|---|
| 1 | C | −3.767125 | −0.316259 | 0.186337 |
| 2 | C | −3.514108 | 0.90246 | 0.809928 |
| 3 | C | −3.90832 | 2.098297 | 0.226311 |
| 4 | C | −4.56568 | 2.094038 | −0.995554 |
| 5 | C | −4.824887 | 0.885497 | −1.627766 |
| 6 | C | −4.42745 | −0.306389 | −1.040134 |
| 7 | H | −2.992705 | 0.910248 | 1.759988 |
| 8 | H | −3.70138 | 3.035771 | 0.727793 |
| 9 | H | −4.876072 | 3.025694 | −1.451767 |
| 10 | H | −5.340852 | 0.871083 | −2.579997 |
| 11 | H | −4.635221 | −1.246642 | −1.539326 |
| 12 | C | −3.300696 | −1.61277 | 0.795178 |
| 13 | H | −3.200925 | −1.495079 | 1.875198 |
| 14 | H | −4.05218 | −2.386327 | 0.623061 |
| 15 | C | −1.966921 | −2.095335 | 0.215657 |
| 16 | H | −1.729092 | −3.08086 | 0.632224 |
| 17 | H | −2.069508 | −2.227516 | −0.864988 |
| 18 | C | −0.796806 | −1.151148 | 0.478243 |
| 19 | C | 0.495551 | −1.705895 | −0.120547 |
| 20 | H | 0.940658 | −2.395918 | 0.603555 |
| 21 | H | 0.258611 | −2.299308 | −1.006363 |
| 22 | C | 1.574129 | −0.714042 | −0.542233 |
| 23 | H | 1.24606 | −0.173858 | −1.44295 |
| 24 | C | 1.954979 | 0.342398 | 0.500963 |
| 25 | H | 2.097636 | −0.150084 | 1.471127 |
| 26 | C | 3.243838 | 1.06123 | 0.124667 |
| 27 | H | 3.031989 | 1.685077 | −0.755535 |
| 28 | C | 4.346739 | 0.097842 | −0.253624 |
| 29 | H | 4.625551 | −0.49664 | 0.623645 |
| 30 | C | 3.813641 | −0.825705 | −1.339761 |
| 31 | H | 3.561228 | −0.235675 | −2.231697 |
| 32 | H | 4.561008 | −1.568857 | −1.618501 |
| 33 | O | 2.691929 | −1.529651 | −0.862988 |
| 34 | O | 0.906845 | 1.288186 | 0.572427 |
| 35 | H | 1.162129 | 1.950827 | 1.218925 |
| 36 | O | 3.594951 | 1.883638 | 1.221218 |
| 37 | H | 4.393489 | 2.361933 | 0.983652 |
| 38 | O | 5.443892 | 0.871926 | −0.702557 |
| 39 | H | 6.236979 | 0.333 | −0.685915 |
| 40 | O | −0.652267 | −0.892746 | 1.871352 |
| 41 | H | −0.523081 | −1.734776 | 2.316028 |
| 42 | H | −1.018433 | −0.178236 | 0.040171 |

DB4

| # | Atom | X | Y | Z |
|---|---|---|---|---|
| 1 | C | −2.42523 | −0.00765 | −0.52919 |
| 2 | C | −2.18392 | −1.29937 | −0.07009 |
| 3 | C | −3.2263 | −2.11468 | 0.349953 |
| 4 | C | −4.53208 | −1.64889 | 0.315864 |
| 5 | C | −4.78701 | −0.36325 | −0.14313 |
| 6 | C | −3.7421 | 0.446822 | −0.56035 |

-continued

| # | Atom | X | Y | Z |
|---|---|---|---|---|
| 7 | H | −1.1684 | −1.679 | −0.03933 |
| 8 | H | −3.01592 | −3.11698 | 0.702286 |
| 9 | H | −5.34684 | −2.28349 | 0.640942 |
| 10 | H | −5.80378 | 0.008145 | −0.17886 |
| 11 | H | −3.94992 | 1.448388 | −0.92065 |
| 12 | C | −1.29524 | 0.894746 | −0.94685 |
| 13 | H | −0.41026 | 0.300226 | −1.17677 |
| 14 | H | −1.56118 | 1.416217 | −1.87027 |
| 15 | C | −0.96274 | 1.944944 | 0.119949 |
| 16 | H | −1.8041 | 2.63605 | 0.197489 |
| 17 | H | −0.86154 | 1.474812 | 1.10154 |
| 18 | C | 0.281606 | 2.771235 | −0.20827 |
| 19 | C | 1.569195 | 2.359984 | 0.514257 |
| 20 | H | 2.336398 | 3.088643 | 0.236353 |
| 21 | H | 1.411553 | 2.459117 | 1.590208 |
| 22 | C | 2.150052 | 0.977345 | 0.244989 |
| 23 | H | 3.199281 | 0.99282 | 0.576212 |
| 24 | C | 1.478233 | −0.16701 | 1.010819 |
| 25 | H | 0.416105 | −0.21308 | 0.758201 |
| 26 | C | 2.101411 | −1.49672 | 0.623495 |
| 27 | H | 3.143777 | −1.5072 | 0.97271 |
| 28 | C | 2.106006 | −1.6688 | −0.88297 |
| 29 | H | 1.069402 | −1.73762 | −1.23352 |
| 30 | C | 2.773906 | −0.45596 | −1.52225 |
| 31 | H | 3.829987 | −0.42348 | −1.22133 |
| 32 | H | 2.725908 | −0.51966 | −2.60922 |
| 33 | O | 2.110723 | 0.730559 | −1.14898 |
| 34 | O | 1.633138 | 0.081609 | 2.392069 |
| 35 | H | 1.31463 | −0.69365 | 2.862341 |
| 36 | O | 1.362493 | −2.51085 | 1.275453 |
| 37 | H | 1.746106 | −3.3578 | 1.033553 |
| 38 | O | 2.804662 | −2.8655 | −1.16616 |
| 39 | H | 2.579572 | −3.16153 | −2.0502 |
| 40 | O | −0.0213 | 4.119188 | 0.155249 |
| 41 | H | 0.742887 | 4.666191 | −0.04096 |
| 42 | H | 0.453933 | 2.726332 | −1.28912 |
| DB5 | | | | |
| 1 | C | −3.86344 | −0.40234 | 0.060083 |
| 2 | C | −3.78529 | 0.590768 | 1.03221 |
| 3 | C | −4.20972 | 1.885571 | 0.767018 |
| 4 | C | −4.7217 | 2.208472 | −0.48115 |
| 5 | C | −4.80664 | 1.226959 | −1.45962 |
| 6 | C | −4.38028 | −0.06457 | −1.1888 |
| 7 | H | −3.38056 | 0.344923 | 2.007446 |
| 8 | H | −4.14012 | 2.643394 | 1.537712 |
| 9 | H | −5.05496 | 3.217219 | −0.69021 |
| 10 | H | −5.20876 | 1.467998 | −2.43601 |
| 11 | H | −4.45129 | −0.82578 | −1.95815 |
| 12 | C | −3.36139 | −1.79631 | 0.331113 |
| 13 | H | −3.33684 | −1.97353 | 1.407044 |
| 14 | H | −4.05372 | −2.5228 | −0.10012 |
| 15 | C | −1.96674 | −2.0537 | −0.24954 |
| 16 | H | −1.68852 | −3.0957 | −0.0649 |
| 17 | H | −1.99244 | −1.91775 | −1.33408 |
| 18 | C | −0.88302 | −1.15347 | 0.319292 |
| 19 | C | 0.454202 | −1.40109 | −0.37176 |
| 20 | H | 0.729114 | −2.4522 | −0.25931 |
| 21 | H | 0.341755 | −1.20225 | −1.44162 |
| 22 | C | 1.5879 | −0.55028 | 0.161967 |
| 23 | H | 1.720945 | −0.74697 | 1.238503 |
| 24 | C | 2.919963 | −0.84119 | −0.53879 |
| 25 | H | 2.78763 | −0.70358 | −1.61529 |
| 26 | C | 3.996247 | 0.120909 | −0.05083 |
| 27 | H | 4.186493 | −0.08136 | 1.014733 |
| 28 | C | 3.528044 | 1.557947 | −0.17451 |
| 29 | H | 3.402862 | 1.790604 | −1.23992 |
| 30 | C | 2.18456 | 1.707494 | 0.521903 |
| 31 | H | 2.310337 | 1.535456 | 1.599597 |
| 32 | H | 1.79291 | 2.713235 | 0.376259 |
| 33 | O | 1.240772 | 0.811764 | −0.01954 |
| 34 | O | 3.343093 | −2.18188 | −0.37539 |
| 35 | H | 3.413537 | −2.37402 | 0.564584 |
| 36 | O | 5.194865 | −0.01314 | −0.78646 |
| 37 | H | 5.45802 | −0.93699 | −0.75543 |
| 38 | O | 4.433943 | 2.459693 | 0.424092 |
| 39 | H | 5.303979 | 2.288131 | 0.054226 |
| 40 | O | −0.79608 | −1.40727 | 1.720273 |
| 41 | H | −0.45871 | −0.62302 | 2.155878 |
| 42 | H | −1.17054 | −0.10936 | 0.16365 |
| DB6 | | | | |
| 1 | C | 3.701258 | 0.180996 | 0.357074 |
| 2 | C | 3.727133 | −0.94712 | 1.173277 |
| 3 | C | 4.595704 | −1.99702 | 0.912944 |
| 4 | C | 5.455876 | −1.93601 | −0.1747 |
| 5 | C | 5.439828 | −0.81775 | −0.9964 |
| 6 | C | 4.569368 | 0.229704 | −0.73036 |
| 7 | H | 3.058858 | −1.00118 | 2.025735 |
| 8 | H | 4.602919 | −2.86384 | 1.562305 |
| 9 | H | 6.136187 | −2.75323 | −0.3787 |
| 10 | H | 6.109294 | −0.75906 | −1.8458 |
| 11 | H | 4.564136 | 1.101416 | −1.37543 |
| 12 | C | 2.723785 | 1.295755 | 0.615454 |
| 13 | H | 2.549012 | 1.38909 | 1.690919 |
| 14 | H | 3.143874 | 2.243807 | 0.276099 |
| 15 | C | 1.386565 | 1.052375 | −0.08549 |
| 16 | H | 1.543915 | 0.973541 | −1.16757 |
| 17 | H | 0.978156 | 0.091337 | 0.233307 |
| 18 | C | 0.35671 | 2.139787 | 0.188619 |
| 19 | C | −1.00579 | 1.873299 | −0.4486 |
| 20 | H | −1.64394 | 2.729017 | −0.22419 |
| 21 | H | −0.90397 | 1.816167 | −1.53733 |
| 22 | C | −1.70667 | 0.61303 | 0.027252 |
| 23 | H | −1.47092 | 0.437441 | 1.090885 |
| 24 | C | −3.23219 | 0.705661 | −0.10871 |
| 25 | H | −3.47774 | 0.928789 | −1.15044 |
| 26 | C | −3.87909 | −0.61838 | 0.2801 |
| 27 | H | −3.69951 | −0.78792 | 1.353367 |
| 28 | C | −3.25514 | −1.77173 | −0.48128 |
| 29 | H | −3.49163 | −1.65157 | −1.54639 |
| 30 | C | −1.7456 | −1.72612 | −0.30623 |
| 31 | H | −1.49212 | −1.90797 | 0.74709 |
| 32 | H | −1.27027 | −2.4954 | −0.91316 |
| 33 | O | −1.23626 | −0.48478 | −0.73658 |
| 34 | O | −3.78615 | 1.76436 | 0.649212 |
| 35 | H | −3.54828 | 1.64377 | 1.573515 |
| 36 | O | −5.26738 | −0.62367 | 0.01889 |
| 37 | H | −5.65398 | 0.137394 | 0.460367 |
| 38 | O | −3.71483 | −3.02085 | −0.01174 |
| 39 | H | −4.67537 | −3.00311 | −0.02752 |
| 40 | O | 0.831964 | 3.421719 | −0.20791 |
| 41 | H | 1.014034 | 3.395013 | −1.15119 |
| 42 | H | 0.218065 | 2.223347 | 1.27135 |
| DB7 | | | | |
| 1 | C | 2.973505 | −0.13611 | 0.449475 |
| 2 | C | 2.817109 | −1.21587 | −0.417 |
| 3 | C | 3.89987 | −2.00262 | −0.77834 |
| 4 | C | 5.164133 | −1.71962 | −0.27799 |
| 5 | C | 5.333301 | −0.64605 | 0.583984 |
| 6 | C | 4.245027 | 0.138274 | 0.942671 |
| 7 | H | 1.831657 | −1.43672 | −0.81156 |
| 8 | H | 3.757272 | −2.84018 | −1.45011 |
| 9 | H | 6.010993 | −2.33395 | −0.55683 |
| 10 | H | 6.314935 | −0.41851 | 0.98111 |
| 11 | H | 4.384538 | 0.974456 | 1.61882 |
| 12 | C | 1.794006 | 0.728893 | 0.803031 |
| 13 | H | 0.924406 | 0.09224 | 0.964872 |
| 14 | H | 1.989022 | 1.254508 | 1.740935 |
| 15 | C | 1.493752 | 1.757946 | −0.29079 |
| 16 | H | 2.355035 | 2.42537 | −0.37552 |
| 17 | H | 1.380543 | 1.250717 | −1.25283 |
| 18 | C | 0.265121 | 2.629323 | −0.01507 |
| 19 | C | −1.06286 | 2.072606 | −0.52984 |
| 20 | H | −1.83299 | 2.808147 | −0.29365 |
| 21 | H | −1.01983 | 1.984089 | −1.62081 |
| 22 | C | −1.50782 | 0.732682 | 0.02529 |
| 23 | H | −1.24118 | 0.661889 | 1.093207 |
| 24 | C | −3.02536 | 0.533744 | −0.09236 |
| 25 | H | −3.31379 | 0.653297 | −1.14011 |
| 26 | C | −3.41273 | −0.86516 | 0.372145 |
| 27 | H | −3.19827 | −0.94217 | 1.449636 |
| 28 | C | −2.59061 | −1.92055 | −0.34145 |

| # | Atom | X | Y | Z |
|---|---|---|---|---|
| 29 | H | −2.85296 | −1.90104 | −1.40705 |
| 30 | C | −1.1147 | −1.58801 | −0.19517 |
| 31 | H | −0.82137 | −1.66991 | 0.860875 |
| 32 | H | −0.51156 | −2.28652 | −0.77384 |
| 33 | O | −0.84555 | −0.29665 | −0.69079 |
| 34 | O | −3.76197 | 1.509191 | 0.61986 |
| 35 | H | −3.5131 | 1.472225 | 1.548421 |
| 36 | O | −4.77703 | −1.14175 | 0.133027 |
| 37 | H | −5.29684 | −0.44584 | 0.544253 |
| 38 | O | −2.8053 | −3.20729 | 0.196418 |
| 39 | H | −3.75228 | −3.37009 | 0.195266 |
| 40 | O | 0.445632 | 3.939175 | −0.54745 |
| 41 | H | 0.546362 | 3.86433 | −1.50006 |
| 42 | H | 0.182669 | 2.785328 | 1.064839 |
| DB8 | | | | |
| 1 | C | −3.59617 | −0.26452 | −0.86901 |
| 2 | C | −4.55498 | −1.11986 | −0.32692 |
| 3 | C | −5.70699 | −0.61913 | 0.257662 |
| 4 | C | −5.92286 | 0.752225 | 0.312911 |
| 5 | C | −4.98043 | 1.614372 | −0.2252 |
| 6 | C | −3.8278 | 1.107654 | −0.81308 |
| 7 | H | −4.39199 | −2.19115 | −0.36275 |
| 8 | H | −6.43978 | −1.30007 | 0.67233 |
| 9 | H | −6.82203 | 1.144099 | 0.770933 |
| 10 | H | −5.14005 | 2.684777 | −0.19053 |
| 11 | H | −3.09468 | 1.787923 | −1.23154 |
| 12 | C | −2.32226 | −0.81591 | −1.45664 |
| 13 | H | −2.56318 | −1.65686 | −2.11075 |
| 14 | H | −1.85313 | −0.05248 | −2.08192 |
| 15 | C | −1.30497 | −1.29262 | −0.41254 |
| 16 | H | −1.72611 | −2.10533 | 0.186695 |
| 17 | H | −0.449 | −1.70921 | −0.9488 |
| 18 | C | −0.81305 | −0.20926 | 0.547667 |
| 19 | C | 0.486619 | −0.6109 | 1.236639 |
| 20 | H | 0.60943 | 0.003101 | 2.13234 |
| 21 | H | 0.401924 | −1.64751 | 1.571142 |
| 22 | C | 1.722196 | −0.49989 | 0.352129 |
| 23 | H | 1.44004 | −0.61588 | −0.70517 |
| 24 | C | 2.45636 | 0.839342 | 0.496492 |
| 25 | H | 2.751493 | 0.96132 | 1.545173 |
| 26 | C | 3.707681 | 0.843004 | −0.3651 |
| 27 | H | 3.400529 | 0.775416 | −1.41877 |
| 28 | C | 4.573871 | −0.35918 | −0.04298 |
| 29 | H | 4.943825 | −0.25168 | 0.984886 |
| 30 | C | 3.736271 | −1.62554 | −0.13523 |
| 31 | H | 3.429726 | −1.78215 | −1.17853 |
| 32 | H | 4.319421 | −2.48731 | 0.186443 |
| 33 | O | 2.608389 | −1.54952 | 0.707214 |
| 34 | O | 1.667877 | 1.938536 | 0.075311 |
| 35 | H | 1.126424 | 2.242814 | 0.805722 |
| 36 | O | 4.483857 | 2.006226 | −0.16284 |
| 37 | H | 3.919677 | 2.765154 | −0.33443 |
| 38 | O | 5.653305 | −0.48497 | −0.94366 |
| 39 | H | 6.11843 | 0.355607 | −0.96032 |
| 40 | O | −1.74691 | 0.043957 | 1.592777 |
| 41 | H | −2.58715 | 0.290815 | 1.195541 |
| 42 | H | −0.64695 | 0.715959 | −0.01897 |
| DB9 | | | | |
| 1 | C | 3.673742 | −0.21094 | 0.147739 |
| 2 | C | 4.604789 | −0.45109 | −0.85843 |
| 3 | C | 5.499575 | 0.534184 | −1.25256 |
| 4 | C | 5.474692 | 1.780965 | −0.6445 |
| 5 | C | 4.549931 | 2.033482 | 0.359813 |
| 6 | C | 3.659052 | 1.044894 | 0.750244 |
| 7 | H | 4.630904 | −1.42358 | −1.33747 |
| 8 | H | 6.219068 | 0.326271 | −2.03498 |
| 9 | H | 6.172914 | 2.550448 | −0.94893 |
| 10 | H | 4.524237 | 3.002731 | 0.842451 |
| 11 | H | 2.939289 | 1.248566 | 1.535553 |
| 12 | C | 2.671933 | −1.26125 | 0.545698 |
| 13 | H | 3.07156 | −2.25556 | 0.329021 |
| 14 | H | 2.495045 | −1.21336 | 1.621228 |
| 15 | C | 1.343233 | −1.08054 | −0.19 |
| 16 | H | 0.946181 | −0.08529 | 0.020901 |
| 17 | H | 1.517584 | −1.13145 | −1.2675 |

| # | Atom | X | Y | Z |
|---|---|---|---|---|
| 18 | C | 0.313973 | −2.14601 | 0.15849 |
| 19 | C | −0.99634 | −2.01673 | −0.62822 |
| 20 | H | −0.75946 | −1.65945 | −1.63312 |
| 21 | H | −1.43319 | −3.0103 | −0.74881 |
| 22 | C | −2.12538 | −1.13669 | −0.0815 |
| 23 | H | −2.54297 | −1.58718 | 0.831522 |
| 24 | C | −1.75403 | 0.318738 | 0.262977 |
| 25 | H | −1.17224 | 0.736734 | −0.57081 |
| 26 | C | −2.99848 | 1.178434 | 0.445033 |
| 27 | H | −3.48044 | 0.863691 | 1.382105 |
| 28 | C | −4.00008 | 0.980093 | −0.67424 |
| 29 | H | −3.56777 | 1.348864 | −1.61121 |
| 30 | C | −4.29378 | −0.50415 | −0.8116 |
| 31 | H | −4.74727 | −0.88112 | 0.115362 |
| 32 | H | −4.98309 | −0.69173 | −1.63503 |
| 33 | O | −3.10171 | −1.19109 | −1.10943 |
| 34 | O | −1.01507 | 0.406875 | 1.463825 |
| 35 | H | −0.61783 | −0.45581 | 1.665673 |
| 36 | O | −2.60074 | 2.531176 | 0.539138 |
| 37 | H | −3.40644 | 3.056119 | 0.550349 |
| 38 | O | −5.15334 | 1.727488 | −0.33061 |
| 39 | H | −5.67295 | 1.886755 | −1.12064 |
| 40 | O | 0.099341 | −2.10444 | 1.574182 |
| 41 | H | −0.44986 | −2.84765 | 1.834518 |
| 42 | H | 0.75194 | −3.11828 | −0.09074 |
| DB10 | | | | |
| 1 | C | −2.01762 | −1.56247 | −0.02527 |
| 2 | C | −1.48471 | −2.04159 | −1.21624 |
| 3 | C | −0.42146 | −2.93514 | −1.2169 |
| 4 | C | 0.119498 | −3.37461 | −0.01902 |
| 5 | C | −0.42123 | −2.92597 | 1.179164 |
| 6 | C | −1.47996 | −2.03285 | 1.17222 |
| 7 | H | −1.89653 | −1.7031 | −2.16025 |
| 8 | H | −0.01339 | −3.28318 | −2.15765 |
| 9 | H | 0.953464 | −4.06491 | −0.01689 |
| 10 | H | −0.01264 | −3.26916 | 2.121427 |
| 11 | H | −1.88638 | −1.68008 | 2.113625 |
| 12 | C | −3.13032 | −0.54201 | −0.00105 |
| 13 | H | −3.51857 | −0.39243 | −1.01161 |
| 14 | H | −3.95587 | −0.95163 | 0.58457 |
| 15 | C | −2.73715 | 0.810597 | 0.618854 |
| 16 | H | −3.61036 | 1.243955 | 1.109731 |
| 17 | H | −1.99431 | 0.655272 | 1.402278 |
| 18 | C | −2.25014 | 1.866658 | −0.37277 |
| 19 | C | −1.09244 | 1.497488 | −1.30099 |
| 20 | H | −1.28008 | 0.499299 | −1.69461 |
| 21 | H | −1.12593 | 2.169849 | −2.16168 |
| 22 | C | 0.359373 | 1.512077 | −0.80323 |
| 23 | H | 0.743238 | 2.543326 | −0.79657 |
| 24 | C | 0.618277 | 0.929348 | 0.592984 |
| 25 | H | 0.106509 | −0.03627 | 0.675663 |
| 26 | C | 2.104264 | 0.693333 | 0.822161 |
| 27 | H | 2.600527 | 1.672733 | 0.869546 |
| 28 | C | 2.723587 | −0.08978 | −0.31264 |
| 29 | H | 2.254963 | −1.08191 | −0.36128 |
| 30 | C | 2.436378 | 0.654412 | −1.60417 |
| 31 | H | 2.912995 | 1.643801 | −1.57261 |
| 32 | H | 2.832418 | 0.106882 | −2.45869 |
| 33 | O | 1.047336 | 0.767345 | −1.79886 |
| 34 | O | 0.206608 | 1.8003 | 1.630666 |
| 35 | H | −0.54395 | 2.339264 | 1.331463 |
| 36 | O | 2.335806 | −0.01739 | 2.024601 |
| 37 | H | 1.972125 | 0.500052 | 2.74756 |
| 38 | O | 4.122664 | −0.20793 | −0.16387 |
| 39 | H | 4.291323 | −0.51004 | 0.732869 |
| 40 | O | −1.95456 | 3.030528 | 0.410765 |
| 41 | H | −1.75088 | 3.762859 | −0.17652 |
| 42 | H | −3.09968 | 2.095686 | −1.02549 |

2. Procedure for Calculating NMRs

To calculate NMR shifts for each of the diastereomers, following the procedure by Smith and Goodman (Bokor, et al., 2017, Chem. Rev. 117:1687-1764), the shielding constants in each conformer were averaged using Boltzmann averaging over the conformers i using the equation:

$$\sigma^x = \frac{\sum_i \sigma_i^x \exp(-E_i/RT)}{\sum_i \exp(-E_i/RT)}$$

where $\sigma^x$ is the Boltzmann averaged shielding constant for nucleus x, $\sigma_i^x$ is the shielding constant for nucleus x in conformer i, and E is the potential energy of conformer i (relative to the global minimum), obtained from the calculation. The temperature T was taken as 298 K.

Averaged shielding constants for each nuclei of the two diastereomers were then scaled using following equation:

$$\delta_{scaled} = \frac{\sigma_{calc} - \text{intercept}}{\text{slope}}$$

where the slope and intercept (Table 5) were obtained from a plot of the calculated vs experimental data for a test set of molecules used by Pierens (Mandal, et al., 2016, Synth. Commun. 46:1327-1342).

TABLE 5

Intercept and slope values calculated for the test set of molecules[14] using ωB97XD/def2TZVP method in methanol.

| | intercept | slope | R |
|---|---|---|---|
| $^1$H | 32.041 | −1.081 | 0.9947 |
| $^{13}$C | 188.78 | −1.048 | 0.9987 |

TABLE 6

NMR shielding constants calculated using GIAO method with ωB97XD/def2TZVP in methanol for the conformers of DA with scaled values

| | | DA1 | DA2 | DA3 | DA4 | DA5 | DA6 | DA7 | DA8 | DA9 | DA10 | $\overline{DA}$ | Scale d |
|---|---|---|---|---|---|---|---|---|---|---|---|---|---|
| 1 | C | 35.418 | 35.213 | 35.710 | 35.068 | 35.296 | 35.880 | 34.978 | 34.336 | 34.980 | 35.019 | 35.210 | 146.550 |
| 2 | C | 53.531 | 53.380 | 53.265 | 53.419 | 53.510 | 53.200 | 53.242 | 52.479 | 53.239 | 53.696 | 53.323 | 129.265 |
| 3 | C | 53.269 | 53.310 | 53.227 | 53.274 | 53.276 | 53.174 | 53.344 | 54.067 | 53.344 | 53.364 | 53.352 | 129.237 |
| 4 | C | 56.806 | 56.866 | 56.696 | 56.912 | 56.773 | 56.658 | 56.920 | 57.624 | 56.920 | 56.874 | 56.893 | 125.858 |
| 5 | C | 53.234 | 53.253 | 53.152 | 53.291 | 53.169 | 53.312 | 53.190 | 54.041 | 53.190 | 53.452 | 53.314 | 129.274 |
| 6 | C | 53.132 | 53.224 | 53.372 | 53.205 | 53.067 | 53.392 | 53.299 | 54.199 | 53.301 | 53.083 | 53.302 | 129.285 |
| 7 | H | 24.218 | 24.207 | 24.210 | 24.212 | 24.206 | 24.164 | 24.209 | 24.219 | 24.209 | 24.215 | 24.208 | 7.249 |
| 8 | H | 24.118 | 24.117 | 24.117 | 24.112 | 24.111 | 24.100 | 24.126 | 24.224 | 24.126 | 24.131 | 24.126 | 7.324 |
| 9 | H | 24.254 | 24.256 | 24.245 | 24.254 | 24.240 | 24.242 | 24.259 | 24.331 | 24.259 | 24.258 | 24.259 | 7.202 |
| 10 | H | 24.117 | 24.118 | 24.104 | 24.118 | 24.095 | 24.118 | 24.111 | 24.143 | 24.111 | 24.107 | 24.115 | 7.335 |
| 11 | H | 24.181 | 24.183 | 24.200 | 24.184 | 24.153 | 24.206 | 24.203 | 24.140 | 24.203 | 24.122 | 24.178 | 7.276 |
| 12 | C | 151.360 | 151.625 | 157.817 | 150.687 | 151.524 | 151.978 | 156.559 | 149.623 | 156.559 | 152.913 | 152.801 | 34.334 |
| 13 | H | 28.812 | 28.857 | 29.309 | 28.772 | 28.772 | 29.368 | 29.281 | 29.281 | 29.280 | 29.525 | 29.077 | 2.743 |
| 14 | H | 29.341 | 29.391 | 29.328 | 29.410 | 29.367 | 29.302 | 29.011 | 28.797 | 29.011 | 28.949 | 29.220 | 2.611 |
| 15 | C | 140.036 | 141.652 | 142.654 | 143.498 | 143.913 | 142.647 | 143.517 | 146.063 | 143.522 | 146.041 | 142.937 | 43.748 |
| 16 | H | 30.241 | 30.407 | 30.095 | 30.335 | 30.017 | 30.483 | 30.163 | 30.133 | 30.163 | 30.204 | 30.241 | 1.666 |
| 17 | H | 30.645 | 30.418 | 30.298 | 30.251 | 30.775 | 30.212 | 30.313 | 29.999 | 30.313 | 30.229 | 30.376 | 1.541 |
| 18 | C | 114.962 | 111.499 | 116.847 | 115.453 | 115.309 | 110.637 | 112.987 | 108.473 | 112.988 | 114.429 | 113.334 | 71.998 |
| 19 | H | 27.837 | 27.956 | 27.677 | 28.240 | 28.139 | 27.984 | 27.802 | 27.907 | 27.802 | 27.866 | 27.917 | 3.816 |
| 20 | C | 139.021 | 146.634 | 141.975 | 141.124 | 144.145 | 149.039 | 149.373 | 146.294 | 149.371 | 149.873 | 145.215 | 41.574 |
| 21 | H | 30.062 | 29.972 | 29.943 | 30.044 | 30.242 | 29.466 | 29.852 | 29.986 | 29.851 | 29.804 | 29.938 | 1.946 |
| 22 | H | 30.479 | 30.556 | 30.175 | 29.918 | 30.068 | 30.654 | 30.234 | 30.588 | 30.234 | 30.002 | 30.329 | 1.585 |
| 23 | C | 109.999 | 102.739 | 109.250 | 109.816 | 108.624 | 102.576 | 102.628 | 102.749 | 102.633 | 110.445 | 106.177 | 78.827 |
| 24 | H | 28.259 | 28.394 | 28.356 | 28.525 | 28.776 | 28.398 | 28.427 | 28.467 | 28.427 | 28.249 | 28.411 | 3.359 |
| 25 | C | 107.099 | 110.986 | 107.017 | 109.583 | 110.141 | 110.869 | 110.822 | 111.002 | 110.822 | 111.855 | 109.859 | 75.313 |
| 26 | H | 28.532 | 28.653 | 28.509 | 28.573 | 28.702 | 28.570 | 28.567 | 28.707 | 28.567 | 28.597 | 28.597 | 3.187 |
| 27 | C | 106.158 | 106.512 | 106.201 | 106.661 | 106.215 | 106.495 | 106.490 | 106.578 | 106.487 | 105.784 | 106.355 | 78.658 |
| 28 | H | 28.426 | 28.474 | 28.430 | 28.478 | 28.565 | 28.448 | 28.458 | 28.522 | 28.458 | 28.425 | 28.465 | 3.309 |
| 29 | C | 112.925 | 113.609 | 112.911 | 113.319 | 113.175 | 113.605 | 113.570 | 113.712 | 113.568 | 112.977 | 113.326 | 72.005 |
| 30 | H | 28.328 | 28.291 | 28.297 | 28.325 | 28.324 | 28.276 | 28.273 | 28.380 | 28.273 | 28.215 | 28.300 | 3.462 |
| 31 | C | 114.715 | 115.319 | 114.671 | 115.141 | 114.912 | 115.341 | 115.300 | 115.446 | 115.300 | 115.403 | 115.132 | 70.281 |
| 32 | H | 28.661 | 28.606 | 28.643 | 28.801 | 28.766 | 28.613 | 28.715 | 28.613 | 28.578 | 28.656 | 3.133 | |
| 33 | H | 28.097 | 27.983 | 28.060 | 28.131 | 28.038 | 27.990 | 27.980 | 28.140 | 27.980 | 27.805 | 28.024 | 3.718 |
| 34 | O | 276.811 | 278.871 | 276.281 | 277.675 | 283.299 | 278.289 | 279.229 | 279.458 | 279.237 | 276.586 | 278.453 | |
| 35 | O | 301.618 | 301.084 | 301.983 | 291.476 | 301.318 | 300.815 | 301.059 | 301.024 | 301.050 | 300.357 | 300.372 | |
| 36 | H | 29.729 | 29.858 | 29.777 | 29.046 | 29.909 | 29.776 | 29.799 | 29.865 | 29.799 | 29.808 | 29.746 | 2.124 |
| 37 | O | 300.850 | 300.417 | 300.873 | 300.742 | 300.338 | 300.365 | 300.366 | 300.389 | 300.358 | 299.661 | 300.468 | |
| 38 | H | 29.601 | 29.571 | 29.604 | 29.576 | 29.616 | 29.541 | 29.544 | 29.595 | 29.545 | 29.538 | 29.575 | 2.282 |
| 39 | O | 304.728 | 305.014 | 304.747 | 304.758 | 304.725 | 305.172 | 305.120 | 305.157 | 305.102 | 304.579 | 304.904 | |
| 40 | H | 30.635 | 30.571 | 30.618 | 30.644 | 30.627 | 30.557 | 30.558 | 30.632 | 30.559 | 30.529 | 30.595 | 1.339 |
| 41 | O | 282.471 | 279.035 | 286.101 | 279.502 | 276.535 | 274.885 | 281.411 | 273.449 | 281.411 | 276.442 | 279.392 | |
| 42 | H | 32.235 | 28.324 | 31.349 | 27.673 | 31.870 | 28.450 | 28.669 | 28.895 | 28.668 | 31.472 | 29.844 | 2.033 |

TABLE 7

NMR shielding constants calculated using GIAO method with ωB97XD/def2TZVP in methanol for the conformers of DB with scaled values

| | | DB1 | DB2 | DB3 | DB4 | DB5 | DB6 | DB7 | DB8 | DB9 | DB10 | $\overline{\text{DB}}$ | Scale d |
|---|---|---|---|---|---|---|---|---|---|---|---|---|---|
| 1 | C | 35.378 | 37.066 | 37.182 | 36.493 | 37.026 | 35.188 | 35.626 | 37.046 | 35.872 | 35.128 | 36.201 | 145.604 |
| 2 | C | 53.148 | 51.512 | 51.328 | 53.741 | 51.678 | 53.093 | 53.216 | 52.440 | 53.377 | 50.930 | 52.445 | 130.103 |
| 3 | C | 53.226 | 53.971 | 54.066 | 53.142 | 53.949 | 53.193 | 53.405 | 53.142 | 53.203 | 53.312 | 53.361 | 129.229 |
| 4 | C | 56.839 | 56.663 | 56.721 | 56.463 | 56.662 | 56.841 | 56.722 | 55.411 | 56.681 | 55.964 | 56.497 | 126.237 |
| 5 | C | 53.300 | 53.152 | 53.235 | 53.087 | 53.096 | 53.296 | 53.284 | 52.267 | 53.243 | 52.120 | 53.008 | 129.566 |
| 6 | C | 53.497 | 53.307 | 53.356 | 53.065 | 53.360 | 53.605 | 53.711 | 53.672 | 53.184 | 51.642 | 53.240 | 129.345 |
| 7 | H | 24.183 | 24.059 | 24.082 | 23.967 | 24.137 | 24.157 | 24.091 | 24.040 | 24.195 | 24.223 | 24.113 | 7.336 |
| 8 | H | 24.118 | 24.116 | 24.150 | 24.121 | 24.138 | 24.100 | 24.102 | 24.015 | 24.116 | 24.144 | 24.112 | 7.338 |
| 9 | H | 24.256 | 24.231 | 24.246 | 24.232 | 24.241 | 24.248 | 24.252 | 24.165 | 24.240 | 24.208 | 24.232 | 7.227 |
| 10 | H | 24.117 | 24.087 | 24.093 | 24.082 | 24.089 | 24.118 | 24.127 | 24.072 | 24.092 | 24.019 | 24.090 | 7.358 |
| 11 | H | 24.218 | 24.191 | 24.197 | 24.147 | 24.190 | 24.220 | 24.196 | 24.129 | 24.161 | 24.010 | 24.166 | 7.288 |
| 12 | C | 151.244 | 154.774 | 154.385 | 151.544 | 154.244 | 151.070 | 151.570 | 149.957 | 151.447 | 155.040 | 152.530 | 34.593 |
| 13 | H | 29.366 | 28.967 | 28.926 | 28.913 | 28.878 | 29.368 | 29.156 | 28.782 | 29.420 | 29.555 | 29.133 | 2.691 |
| 14 | H | 28.862 | 29.138 | 29.169 | 29.123 | 29.104 | 28.823 | 29.352 | 29.289 | 28.797 | 28.744 | 29.040 | 2.777 |
| 15 | C | 138.919 | 145.718 | 143.272 | 144.909 | 147.124 | 141.593 | 139.987 | 147.007 | 143.772 | 150.505 | 144.286 | 42.461 |
| 16 | H | 30.475 | 30.164 | 30.214 | 29.958 | 30.163 | 30.734 | 30.114 | 30.371 | 29.580 | 29.580 | 30.135 | 1.763 |
| 17 | H | 30.327 | 30.552 | 30.419 | 30.221 | 30.451 | 29.889 | 30.118 | 29.731 | 30.424 | 29.818 | 30.195 | 1.708 |
| 18 | C | 116.779 | 121.735 | 121.637 | 116.042 | 122.481 | 110.833 | 112.337 | 113.397 | 114.781 | 112.965 | 116.302 | 69.165 |
| 19 | C | 138.613 | 150.169 | 139.272 | 147.005 | 145.128 | 145.416 | 144.005 | 142.856 | 144.150 | 149.632 | 144.633 | 42.129 |
| 20 | H | 30.632 | 30.159 | 30.662 | 29.954 | 30.056 | 29.418 | 29.323 | 30.263 | 30.460 | 30.013 | 30.093 | 1.802 |
| 21 | H | 29.940 | 30.421 | 30.087 | 29.850 | 30.851 | 30.735 | 30.589 | 30.391 | 29.429 | 29.742 | 30.204 | 1.700 |
| 22 | C | 107.873 | 104.470 | 108.024 | 107.530 | 108.929 | 106.129 | 107.086 | 108.304 | 108.536 | 109.096 | 107.595 | 77.474 |
| 23 | H | 28.550 | 28.555 | 28.869 | 28.412 | 28.735 | 28.993 | 28.745 | 28.991 | 28.414 | 28.757 | 28.702 | 3.090 |
| 24 | C | 110.682 | 113.472 | 110.884 | 114.787 | 108.429 | 109.517 | 109.309 | 105.870 | 111.256 | 113.993 | 110.820 | 74.397 |
| 25 | H | 28.253 | 28.626 | 28.329 | 27.774 | 29.090 | 29.056 | 28.949 | 28.654 | 28.581 | 30.173 | 28.749 | 3.046 |
| 26 | C | 104.871 | 106.394 | 104.967 | 105.426 | 103.714 | 103.615 | 103.618 | 106.144 | 104.940 | 103.431 | 104.712 | 80.225 |
| 27 | H | 28.450 | 28.588 | 28.596 | 28.427 | 28.678 | 28.663 | 28.598 | 28.484 | 28.449 | 28.884 | 28.582 | 3.201 |
| 28 | C | 113.595 | 114.365 | 113.632 | 113.052 | 114.066 | 114.146 | 114.153 | 113.971 | 113.336 | 115.879 | 114.021 | 71.342 |
| 29 | H | 28.353 | 28.259 | 28.406 | 27.858 | 28.362 | 28.315 | 28.103 | 28.247 | 28.427 | 29.156 | 28.349 | 3.417 |
| 30 | C | 116.126 | 116.255 | 116.190 | 114.735 | 116.707 | 117.078 | 116.786 | 116.052 | 116.120 | 117.398 | 116.345 | 69.124 |
| 31 | H | 28.749 | 28.717 | 28.862 | 28.627 | 28.744 | 28.770 | 28.569 | 28.627 | 28.745 | 28.997 | 28.741 | 3.054 |
| 32 | H | 28.165 | 27.914 | 28.221 | 27.938 | 28.109 | 28.181 | 27.676 | 27.972 | 28.167 | 28.303 | 28.064 | 3.680 |
| 33 | O | 277.171 | 280.739 | 277.358 | 280.987 | 283.220 | 276.278 | 278.248 | 276.673 | 276.848 | 279.114 | 278.667 | |
| 34 | O | 294.824 | 304.884 | 294.746 | 300.218 | 299.916 | 297.959 | 297.636 | 305.825 | 285.610 | 292.277 | 297.399 | |
| 35 | H | 29.877 | 30.981 | 30.015 | 29.816 | 31.930 | 31.823 | 31.781 | 30.291 | 26.828 | 27.175 | 30.054 | 1.839 |
| 36 | O | 299.772 | 300.740 | 299.797 | 299.262 | 300.016 | 299.231 | 299.204 | 301.272 | 296.751 | 302.594 | 299.866 | |
| 37 | H | 29.592 | 29.696 | 29.653 | 29.393 | 29.609 | 29.591 | 29.544 | 29.513 | 29.600 | 30.062 | 29.625 | 2.236 |
| 38 | O | 304.195 | 303.840 | 304.278 | 303.703 | 303.586 | 303.334 | 303.135 | 303.304 | 304.996 | 306.911 | 304.128 | |
| 39 | H | 30.626 | 29.994 | 30.674 | 30.479 | 30.069 | 30.054 | 29.958 | 29.998 | 30.603 | 30.209 | 30.266 | 1.643 |
| 40 | O | 269.833 | 282.227 | 271.289 | 270.523 | 298.437 | 272.454 | 257.246 | 269.539 | 278.286 | 270.583 | 274.059 | |
| 41 | H | 32.160 | 28.700 | 32.205 | 31.558 | 30.741 | 31.797 | 31.325 | 32.164 | 30.295 | 30.491 | 31.141 | 0.833 |
| 42 | H | 27.882 | 28.324 | 28.323 | 27.945 | 28.435 | 28.398 | 28.450 | 27.975 | 27.673 | 27.736 | 28.114 | 3.634 |

3. Calculation of the CP3 and the Probability Parameters

Using the applet available at www-jmgdotchdotcamdotacdotuk/tools/nmr/, the values of the CP3 parameter and corresponding probability for the assignment of the pair of diastereoisomers developed by Smith and Goodman were calculated (Bokor, et al., 2017, Chem. Rev. 117:1687-1764). The CP3 parameter is based on comparing differences in experimental and calculated NMR shifts and combined with Bayes' theorem to obtain quantifiable confidence of diastereomer assignment. Values for the CP3 parameter obtained from the applet are shown in Table 8.

TABLE 8

CP3 parameter and the probability factor obtained from the Smith and Goodman calculations.

| | C data | H data | All data |
|---|---|---|---|
| CP3 | | | |
| 3a-DA & 3a'-DB | 0.36 | 0.29 | 0.33 |
| 3a-DB & 3a'-DA | −0.57 | −0.45 | −0.51 |
| probability | | | |
| 3a-DA & 3a'-DB | 100.0% | 98.3% | 100.0% |
| 3a-DB & 3a'-DA | 0.0% | 1.7% | 0.0% |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing an α,β-unsaturated ketone to its corresponding saturated ketone, the method comprising contacting the α,β-unsaturated ketone, a solvent, a copper-doped porous metal oxide, and hydrogen gas to form a reaction mixture, wherein the reaction mixture is quenched by acidification.

2. The method of claim 1, wherein at least one applies:
(i) the reaction mixture further comprises a Lewis acid;
(ii) the solvent comprises methanol or water;
(iii) the reaction mixture is kept at a temperature ranging from 0° C. to about 100° C.;
(iv) the metal oxide comprises copper(II), magnesium(II), and aluminum (III);
(v) the pressure of hydrogen gas used ranges from about 1 to 10 MPa;
(vi) the reaction is run for about 1 hour to about 24 hours;
(vii) the concentration of the α,β-unsaturated ketone in the reaction mixture is about 0.01-0.1 M;
(viii) the metal oxide used corresponds to about 1 to about 100 mol % in terms of the α,β-unsaturated ketone;
(ix) the reaction mixture is passed through a flow through reactor; or
(x) the reaction mixture is formed within a flow through reactor.

3. The method of claim 2, wherein
(i) the ratio of [copper(II)+magnesium(II)] to aluminum (III) is about 1.5:1 to about 6:1; or
(ii) the ratio of copper(II) to magnesium (II) is about 1:9 to about 4:6.

4. The method of claim 1, wherein the quenched reaction mixture is purified by a separation method that separates solid material from the product-containing solution.

5. The method of claim 4, wherein the solid material is extracted at least once with an alcohol.

6. The method of claim 5, wherein the at least one alcohol extract is combined with the product-containing solution.

7. The method of claim 4, wherein the saturated ketone is isolated from the product-containing solution.

8. The method of claim 1, wherein
(i) the 3-position of the α,β-unsaturated ketone is substituted with an optionally substituted aliphatic or an optionally substituted aromatic; or
(ii) the 1-position of the α,β-unsaturated ketone is substituted with an optionally substituted (glycosyl)methyl group.

9. The method of claim 1, wherein the α,β-unsaturated ketone is an optionally substituted 2-propen-1-one and its corresponding saturated ketone is an optionally substituted propan-1-one.

* * * * *